(12) United States Patent
Shitagaki et al.

(10) Patent No.: US 9,419,237 B2
(45) Date of Patent: Aug. 16, 2016

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Satoko Shitagaki, Kanagawa (JP); Takao Hamada, Kanagawa (JP); Kanta Abe, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 412 days.

(21) Appl. No.: 13/957,023

(22) Filed: Aug. 1, 2013

(65) Prior Publication Data
US 2014/0034928 A1 Feb. 6, 2014

(30) Foreign Application Priority Data

Aug. 3, 2012 (JP) ................................. 2012-172952

(51) Int. Cl.
| | |
|---|---|
| *H01L 51/50* | (2006.01) |
| *H01L 51/00* | (2006.01) |
| *C07D 409/10* | (2006.01) |
| *C07D 209/86* | (2006.01) |

(52) U.S. Cl.
CPC .......... *H01L 51/5056* (2013.01); *C07D 209/86* (2013.01); *C07D 409/10* (2013.01); *H01L 51/006* (2013.01); *H01L 51/0072* (2013.01); *H01L 51/0067* (2013.01); *H01L 51/0074* (2013.01); *H01L 51/0085* (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| | | | |
|---|---|---|---|
| 7,572,522 | B2 | 8/2009 | Seo et al. |
| 7,943,925 | B2 | 5/2011 | Yamazaki |
| 8,247,086 | B2 | 8/2012 | Inoue et al. |
| 2005/0048310 | A1 | 3/2005 | Cocchi et al. |
| 2005/0196775 | A1 | 9/2005 | Swager et al. |
| 2005/0221124 | A1 | 10/2005 | Hwang et al. |
| 2006/0228577 | A1 | 10/2006 | Nagara |
| 2007/0222374 | A1 | 9/2007 | Egawa et al. |
| 2007/0244320 | A1 | 10/2007 | Inoue et al. |
| 2008/0124572 | A1 | 5/2008 | Mizuki et al. |
| 2008/0160345 | A1 | 7/2008 | Inoue et al. |
| 2008/0286604 | A1 | 11/2008 | Inoue et al. |
| 2009/0160323 | A1 | 6/2009 | Nomura et al. |
| 2010/0052527 | A1 | 3/2010 | Ikeda et al. |
| 2010/0145044 | A1 | 6/2010 | Inoue et al. |
| 2011/0001146 | A1 | 1/2011 | Yamazaki et al. |
| 2011/0210316 | A1 | 9/2011 | Kadoma et al. |
| 2011/0215714 | A1 | 9/2011 | Seo et al. |
| 2012/0098417 | A1 | 4/2012 | Inoue et al. |
| 2012/0205632 | A1 | 8/2012 | Shitagaki et al. |
| 2012/0205687 | A1 | 8/2012 | Yamazaki et al. |
| 2012/0206035 | A1 | 8/2012 | Shitagaki et al. |
| 2012/0217486 | A1 | 8/2012 | Takemura et al. |
| 2012/0217487 | A1 | 8/2012 | Yamazaki et al. |
| 2012/0242219 | A1 | 9/2012 | Seo et al. |
| 2012/0248421 | A1 | 10/2012 | Yamazaki et al. |
| 2012/0256535 | A1 | 10/2012 | Seo et al. |
| 2013/0048964 | A1 | 2/2013 | Takeda et al. |
| 2014/0034929 | A1 | 2/2014 | Hamada et al. |

FOREIGN PATENT DOCUMENTS

| | | | |
|---|---|---|---|
| EP | 1862524 | * 12/2007 | .............. H01L 51/50 |
| JP | 2009-298767 | 12/2009 | |
| JP | 2012-4526 | 1/2012 | |
| WO | WO 00/70655 A2 | 11/2000 | |

OTHER PUBLICATIONS

Gu, G. et al., "Transparent Organic Light Emitting Devices," Applied Physics Letters, vol. 68, No. 19, May 6, 1996, pp. 2606-2608.

Itano, K. et al, "Exciplex Formation at the Organic Solid-State Interface: Yellow Emission in Organic Light-Emitting Diodes Using Green-Fluorescent tris(8-quinolinolato)aluminum and Hole-Transporting Molecular Materials with Low Ionization Potentials," Applied Physics Letters, vol. 72, No. 6, Feb. 9, 1998, pp. 636-638.

Baldo, M.A. et al., "Highly Efficient Phosphorescent Emission from Organic Electroluminescent Devices," Nature, vol. 395, Sep. 10, 1998, pp. 151-154.

Baldo, M.A. et al, "Very High-Efficiency Green Organic Light-Emitting Devices Based on Electrophosphorescence," Applied Physics Letters, vol. 75, No. 1, Jul. 5, 1999, pp. 4-6.

Choong, V.-E. et al, "Organic Light-Emitting Diodes With a Bipolar Transport Layer," Applied Physics Letters, vol. 75, No. 2, Jul. 12, 1999, pp. 172-174.

Adachi, C. et al., "Nearly 100% Internal Phosphorescence Efficiency in an Organic Light Emitting Device," Journal of Applied Physics, vol. 90, No. 10, Nov. 15, 2001, pp. 5048-5051.

(Continued)

*Primary Examiner* — Gregory Clark

(74) *Attorney, Agent, or Firm* — Husch Blackwell LLP

(57) ABSTRACT

A novel organic compound having a high hole-transport property is provided. A long-lifetime light-emitting element is provided. An organic compound represented by General Formula (G0) is provided. In General Formula (G0), $Ar^1$ represents a substituted or unsubstituted naphthyl group, $Ar^2$ represents a substituted or unsubstituted carbazolyl group, $Ar^3$ represents a substituted or unsubstituted fluorenyl group or a substituted or unsubstituted spirofluorenyl group, and $\alpha^1$ and $\alpha^2$ each independently represent a substituted or unsubstituted phenylene group or a substituted or unsubstituted biphenyldiyl group.

12 Claims, 21 Drawing Sheets

(56) References Cited

OTHER PUBLICATIONS

Baldo, M.A. et al., "Prospects for Electrically Pumped Organic Lasers," Physical Review B, vol. 66, Jul. 1, 2002, pp. 035321-1-035321-16.

Markham, J.P.J. et al., "High-Efficiency Green Phosphorescence from Spin-Coated Single-Layer Dendrimer Light-Emitting Diodes," Applied Physics Letters, vol. 80, No. 15, Apr. 15, 2002, pp. 2645-2647.

Fujita, M. et al., Reduction of Operating Voltage in Organic Light-Emitting Diode by Corrugated Photonic Crystal Structure, Applied Physics Letters, vol. 85, No. 23, Dec. 6, 2004, pp. 5769-5771.

Kondakova, M.E. et al., "High-Efficiency, Low-Voltage Phosphorescent Organic Light-Emitting Diode Devices with Mixed Host," Journal of Applied Physics, vol. 104, 2008, pp. 094501-1-094501-17.

Seo, J.H., et al., "Efficient Blue-Green Organic Light-Emitting Diodes Based on Heteroleptic tris-Cyclometalated Iridium(III) Complexes," Thin Solid Films, vol. 517, No. 5, 2009, pp. 1807-1810.

\* cited by examiner

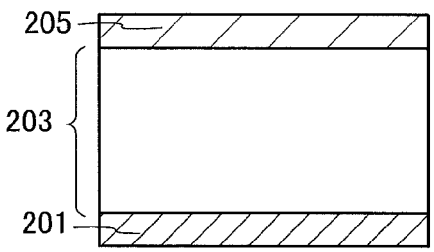
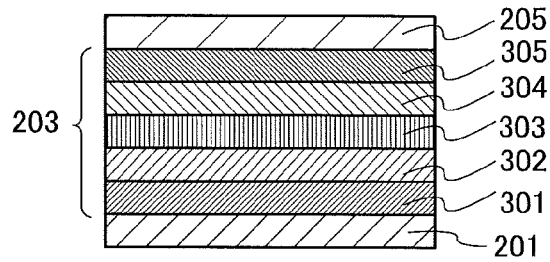
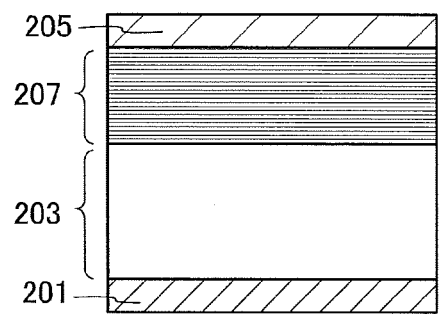
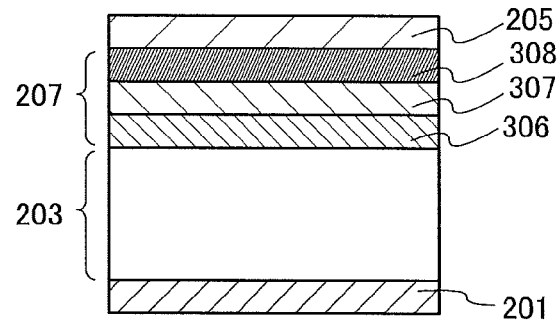
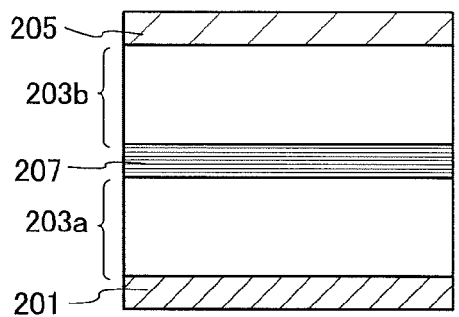
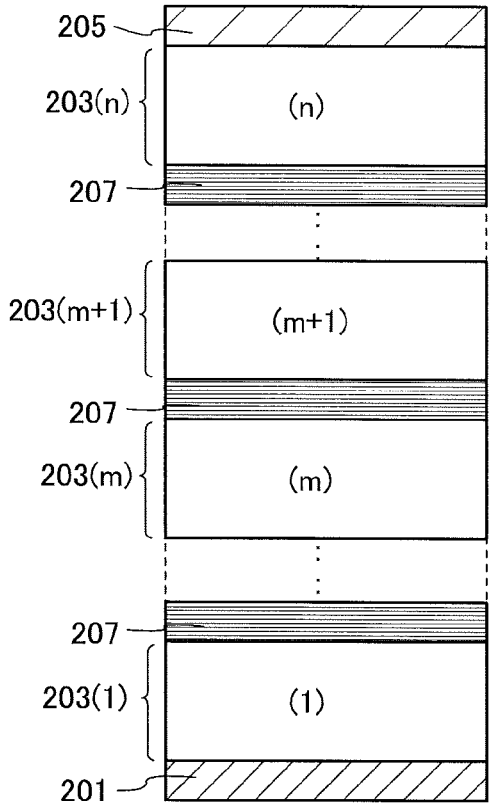

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to an organic compound, a light-emitting element, a light-emitting device, an electronic device, and a lighting device.

2. Description of the Related Art

In recent years, research and development have been extensively conducted on light-emitting elements using electroluminescence (EL) (also referred to as EL element). In a basic structure of an EL element, a layer containing a light-emitting substance is provided between a pair of electrodes. By applying voltage to this element, light emission from the light-emitting substance can be obtained.

An EL element is a self-luminous element and thus has advantages over a liquid crystal display element, such as high visibility of the pixels and no need of backlight, and is considered to be suitable as a flat panel display element. Another major advantage of such an EL element is that it can be manufactured to be thin and lightweight. Besides, the EL element has an advantage of quite fast response speed.

Since an EL element can be formed in a film form, planar light emission can be obtained; thus, a large-area element can be easily formed. This feature is difficult to obtain with point light sources typified by incandescent lamps and LEDs or linear light sources typified by fluorescent lamps. Thus, the light-emitting element also has great potential as a planar light source applicable to a lighting device and the like.

EL elements can be broadly classified according to whether a light-emitting substance is an organic compound or an inorganic compound. In the case of an organic EL element in which a layer containing an organic compound used as a light-emitting substance is provided between a pair of electrodes, by applying a voltage to the light-emitting element, electrons from a cathode and holes from an anode are injected into the layer containing the organic compound and thus a current flows. The injected electrons and holes then lead the organic compound to its excited state, so that light emission is obtained from the excited organic compound.

The excited state formed by an organic compound can be a singlet excited state or a triplet excited state. Light emission from the singlet excited state (S*) is called fluorescence, and emission from the triplet excited state (T*) is called phosphorescence.

In improving element characteristics of the light-emitting element, there are many problems which depend on substances used for the light-emitting element. Therefore, improvement in an element structure, development of a substance, and the like have been carried out in order to solve the problems. For example, Patent Document 1 discloses a carbazole derivative having a high hole-transport property as a material that can be used for forming a light-emitting element with high emission efficiency.

REFERENCE

[Patent Document 1] Japanese Published Patent Application No. 2009-298767

SUMMARY OF THE INVENTION

The development of organic EL elements has room for improvement in emission efficiency, reliability, cost, and the like. More excellent substances are desired to be developed.

An object of one embodiment of the present invention is to provide a novel organic compound having a high hole-transport property.

Another object of one embodiment of the present invention is to provide a light-emitting element having a long lifetime.

Another object of one embodiment of the present invention is to provide a light-emitting device, an electronic device, and a lighting device each having high reliability by using the above light-emitting element.

The organic compound of one embodiment of the present invention is a tertiary amine in which a substituent including a fluorene skeleton or a spirofluorene skeleton, a substituent including a naphthalene skeleton, and a substituent including a carbazole skeleton are directly bonded to a nitrogen atom. The organic compound of one embodiment of the present invention has a high hole-transport property.

Specifically, one embodiment of the present invention is an organic compound represented by General Formula (G0).

[Chemical formula 1]

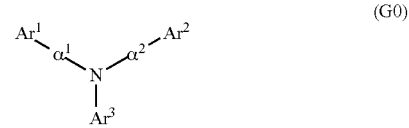

(G0)

In General Formula (G0), $Ar^1$ represents a naphthyl group; $Ar^2$ represents a carbazolyl group; $Ar^3$ represents a fluorenyl group or a spirofluorenyl group; and $\alpha^1$ and $\alpha^2$ each independently represent a phenylene group or a biphenyldiyl group. The naphthyl group, the carbazolyl group, the fluorenyl group, the spirofluorenyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.

Another embodiment of the present invention is an organic compound represented by General Formula (G1).

[Chemical formula 2]

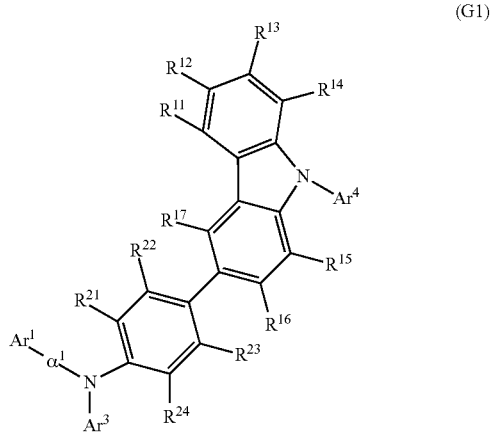

(G1)

In General Formula (G1), $Ar^1$ represents a naphthyl group; $Ar^3$ represents a fluorenyl group or a spirofluorenyl group; $Ar^4$ represents an aryl group having 6 to 25 carbon atoms; $\alpha^1$ represents a phenylene group or a biphenyldiyl group; and $R^{11}$ to $R^{17}$ and $R^{21}$ to $R^{24}$ each independently represent hydrogen, an alkyl group having 1 to 10 carbon atoms, or an aryl group having 6 to 25 carbon atoms. The naphthyl group, the fluorenyl group, the spirofluorenyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.

Another embodiment of the present invention is an organic compound represented by General Formula (G3).

[Chemical formula 4]

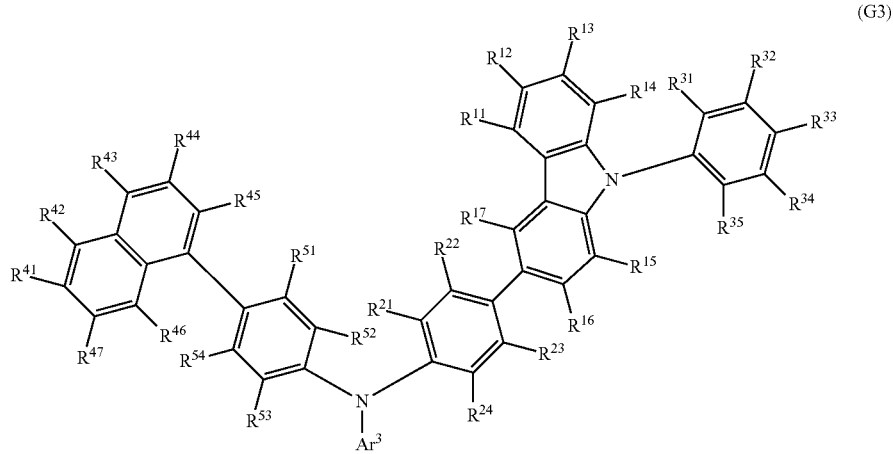

(G3)

Another embodiment of the present invention is an organic compound represented by General Formula (G2).

[Chemical formula 3]

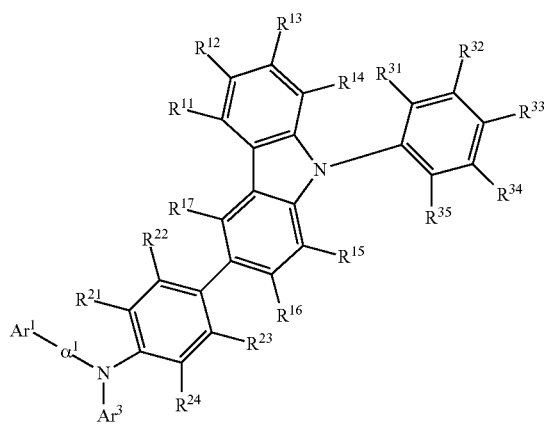

(G2)

In General Formula (G2), $Ar^1$ represents a naphthyl group; $Ar^a$ represents a fluorenyl group or a spirofluorenyl group; $\alpha^1$ represents a phenylene group or a biphenyldiyl group; $R^{11}$ to $R^{17}$ and $R^{21}$ to $R^{24}$ each independently represent hydrogen, an alkyl group having 1 to 10 carbon atoms, or an aryl group having 6 to 25 carbon atoms; and $R^{31}$ to $R^{35}$ each independently represent hydrogen or an alkyl group having 1 to 10 carbon atoms. The naphthyl group, the fluorenyl group, the spirofluorenyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.

In General Formula (G3), $Ar^3$ represents a fluorenyl group or a spirofluorenyl group; $R^{11}$ to $R^{17}$, $R^{21}$ to $R^{24}$, $R^{41}$ to $R^{47}$, and $R^{51}$ to $R^{54}$ each independently represent hydrogen, an alkyl group having 1 to 10 carbon atoms, or an aryl group having 6 to 25 carbon atoms; and $R^{31}$ to $R^{35}$ each independently represent hydrogen or an alkyl group having 1 to 10 carbon atoms. The fluorenyl group or the spirofluorenyl group is unsubstituted or substituted. In the case where the fluorenyl group or the spirofluorenyl group has a substituent, the substituent is an alkyl group having 1 to 10 carbon atoms or an aryl group having 6 to 25 carbon atoms.

Another embodiment of the present invention is a light-emitting element including any of the above-described organic compounds between a pair of electrodes.

Another embodiment of the present invention is a light-emitting element including a light-emitting layer between a pair of electrodes, and the light-emitting layer contains any of the above-described organic compounds and a light-emitting substance. Another embodiment of the present invention is a light-emitting element including a light-emitting layer between a pair of electrodes, and the light-emitting layer contains a first organic compound, a second organic compound, and a light-emitting substance. The first organic compound is any of the above-described organic compounds, and the second organic compound is an organic compound having an electron-transport property. In particular, the combination of the first organic compound and the second organic compound preferably forms an exciplex, in which case emission efficiency of the light-emitting element can be enhanced.

Another embodiment of the present invention is a light-emitting element including, between a pair of electrodes, a light-emitting layer containing a light-emitting substance and a hole-transport layer that is in contact with the light-emitting layer. The hole-transport layer contains any of the above-described organic compounds.

Another embodiment of the present invention is a light-emitting element including, between a pair of electrodes, a light-emitting layer and a hole-transport layer that is in contact with the light-emitting layer. The light-emitting layer contains a light-emitting substance and any of the above-described organic compounds. The hole-transport layer contains the organic compound of one embodiment of the present invention.

Another embodiment of the present invention is a light-emitting device including any of the above-described light-emitting elements in a light-emitting portion. Another embodiment of the present invention is an electronic device including the light-emitting device in a display portion. Another embodiment of the present invention is a lighting device including the light-emitting device in a light-emitting portion.

The light-emitting element including the organic compound of one embodiment of the present invention has a long lifetime; thus, a highly reliable light-emitting device can be achieved. Similarly, a highly reliable electronic device and a highly reliable lighting device can be achieved by application of one embodiment of the present invention.

The light-emitting device in this specification includes an image display device that uses a light-emitting element. The category of the light-emitting device in this specification includes a module in which a light-emitting element is provided with a connector such as an anisotropic conductive film or a TCP (tape carrier package); a module in which a printed wiring board is provided at the end of a TCP; and a module in which an IC (integrated circuit) is directly mounted on a light-emitting element by a COG (chip on glass) method. In addition, a light-emitting device that is used in lighting equipment and the like are also included.

The above-described organic compounds of one embodiment of the present invention has a high hole-transport property. With the use of the organic compound of one embodiment of the present invention, a light-emitting element having a long lifetime can be achieved. Furthermore, by application of one embodiment of the present invention, a highly reliable light-emitting device, a highly reliable electronic device, and a highly reliable lighting device can be provided.

BRIEF DESCRIPTION OF THE DRAWINGS

FIGS. 1A to 1F each illustrate an example of a light-emitting element of one embodiment of the present invention.

DETAILED DESCRIPTION OF THE INVENTION

Figure 2:
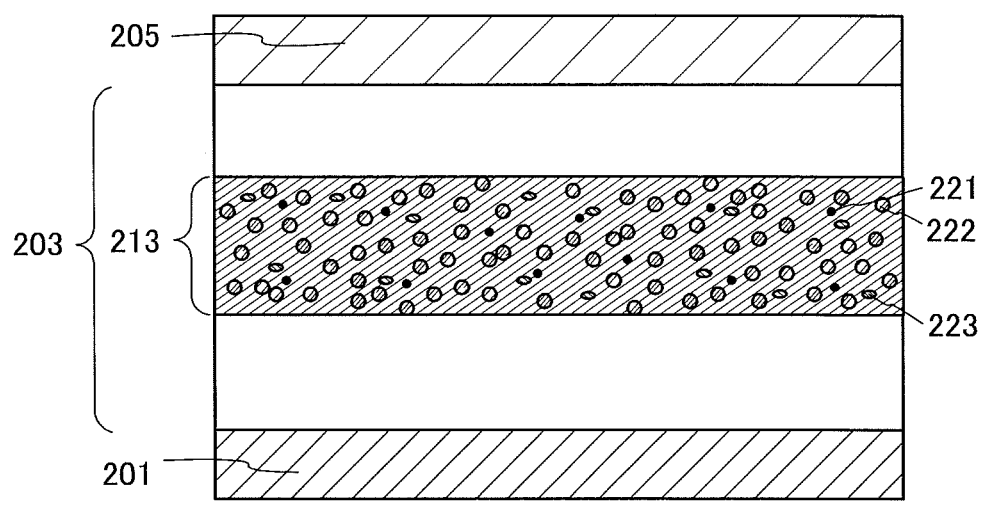
FIG. 2 illustrates an example of a light-emitting element of one embodiment of the present invention.

Embodiments of the present invention will be described with reference to the drawings. Note that the present invention is not limited to the following description, and it is easily understood by those skilled in the art that various changes for embodiments and details can be made without departing from the spirit and scope of the invention. Therefore, the present invention should not be construed as being limited to the description in the following embodiments. Note that in the structures of the invention described below, the same portions or portions having similar functions are denoted by the same reference numerals in different drawings, and description of such portions is not repeated.

Embodiment 1

In this embodiment, an organic compound of one embodiment of the present invention will be described.

One embodiment of the present invention is a tertiary amine in which a substituent including a fluorene skeleton or a spirofluorene skeleton, a substituent including a naphthalene skeleton, and a substituent including a carbazole skeleton are directly bonded to a nitrogen atom. The organic compound of one embodiment of the present invention has a high hole-transport property. With the use of the organic compound, a light-emitting element with a long lifetime can be achieved.

Specifically, one embodiment of the present invention is an organic compound represented by General Formula (G0).

[Chemical formula 5]

$$Ar^1\!-\!\alpha^1\!-\!\underset{\underset{Ar^3}{|}}{N}\!-\!\alpha^2\!-\!Ar^2 \quad (G0)$$

In General Formula (G0), $Ar^1$ represents a naphthyl group; $Ar^2$ represents a carbazolyl group; $Ar^3$ represents a fluorenyl group or a spirofluorenyl group; and $\alpha^1$ and $\alpha^2$ each independently represent a phenylene group or a biphenyldiyl group. The naphthyl group, the carbazolyl group, the fluorenyl group, the spirofluorenyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.
Specific examples of Ar² in General Formula (G0) include substituents represented by Structural Formulae (1-1) to (1-27).
[Chemical formula 6]
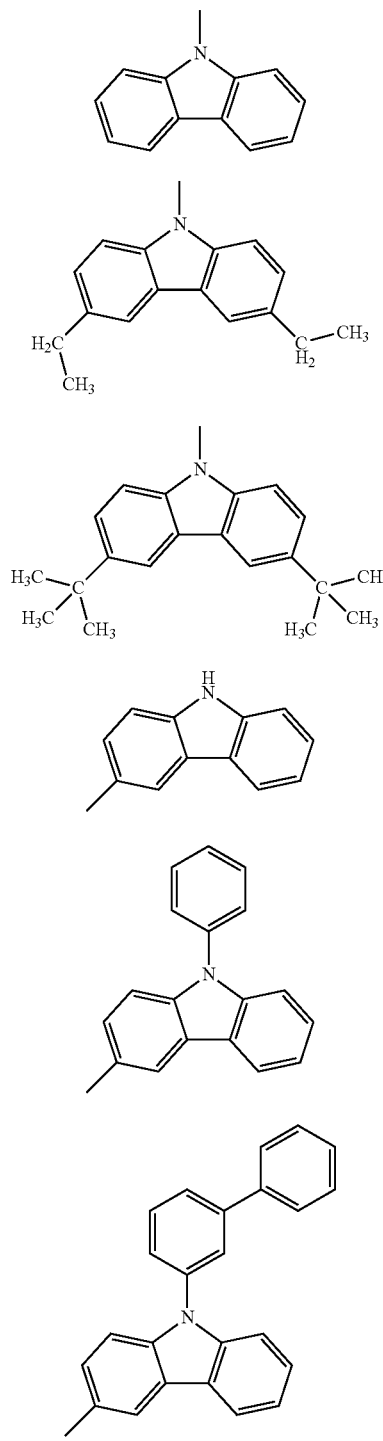
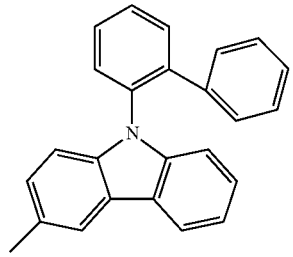
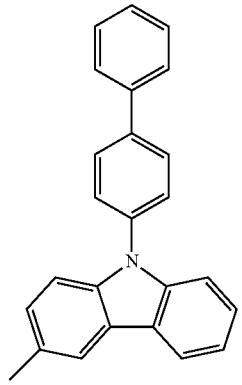
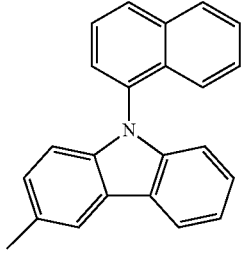
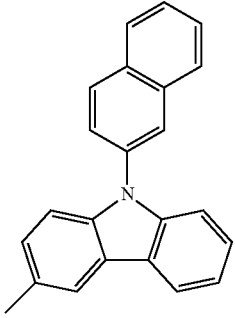
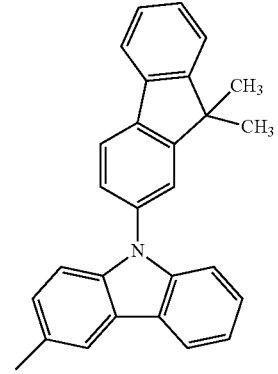

(1-12)
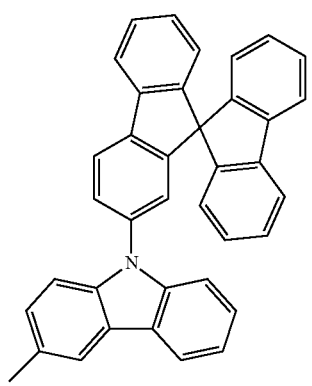
(1-13)
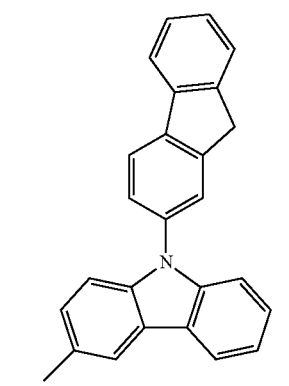
(1-14)
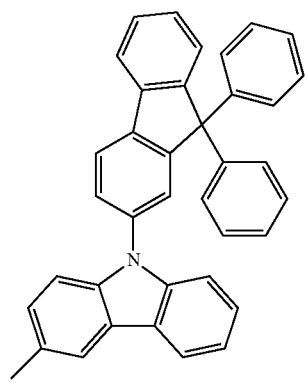
(1-15)
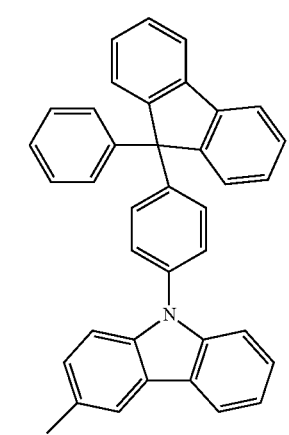
[Chemical formula 7]
(1-16)
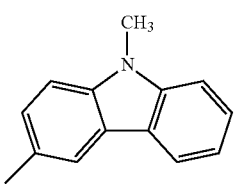
(1-17)
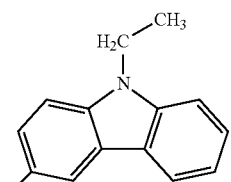
(1-18)
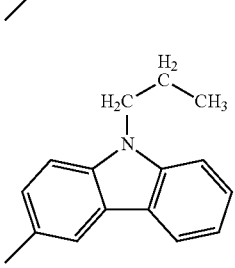
(1-19)
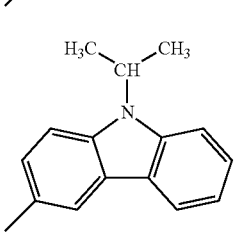
(1-20)
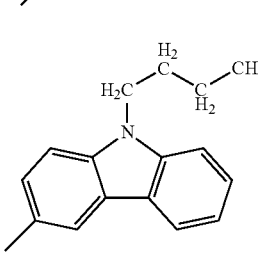
(1-21)
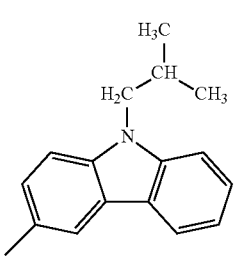
(1-22)
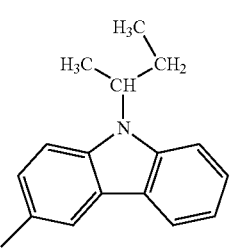

-continued (1-23) 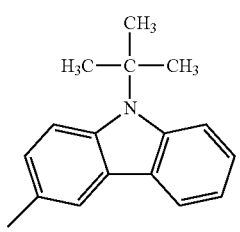

(1-24) 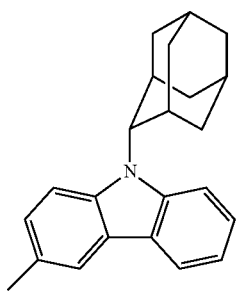

(1-25) 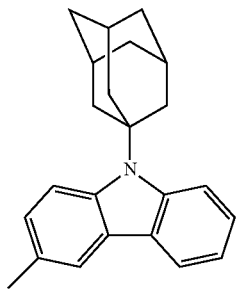

(1-26) 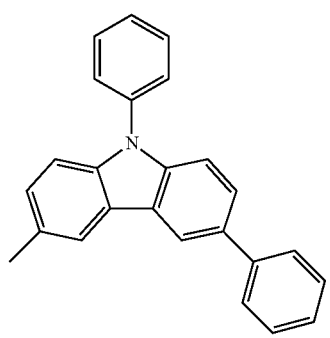

(1-27) 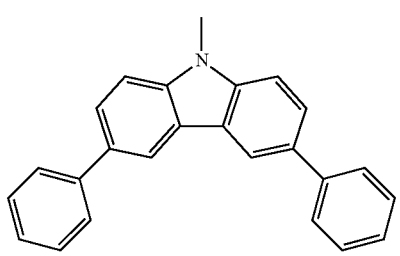

Another embodiment of the present invention is an organic compound represented by General Formula (G1). The range of choices for a synthesis method of the organic compound represented by General Formula (G1) is wide, which is preferable because purification of a material and a reduction in cost of the organic compound can be easily achieved.

[Chemical formula 8]

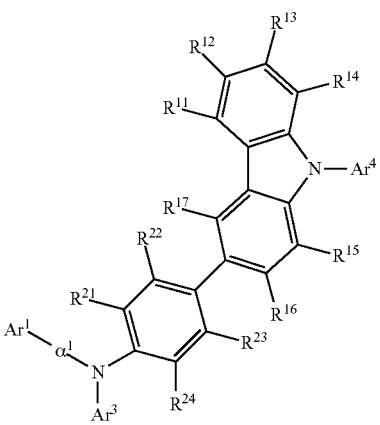

(G1)

In General Formula (G1), $Ar^1$ represents a naphthyl group; $Ar^a$ represents a fluorenyl group or a spirofluorenyl group; $Ar^4$ represents an aryl group having 6 to 25 carbon atoms; $\alpha^1$ represents a phenylene group or a biphenyldiyl group; and $R^{11}$ to $R^{17}$ and $R^{21}$ to $R^{24}$ each independently represent hydrogen, an alkyl group having 1 to 10 carbon atoms, or an aryl group having 6 to 25 carbon atoms. The naphthyl group, the fluorenyl group, the spirofluorenyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.

In General Formula (G1), $Ar^4$ is preferably a phenyl group, in which case the thermophysical property of the organic compound is improved in comparison with the case where $Ar^4$ is an alkyl group, so that a long-lifetime light-emitting element can be fabricated. Thus, another embodiment of the present invention is an organic compound represented by General Formula (G2).

[Chemical formula 9]

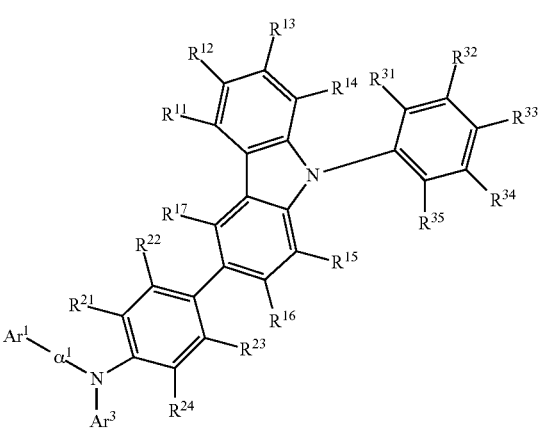

(G2)

In General Formula (G2), $Ar^1$ represents a naphthyl group; $Ar^3$ represents a fluorenyl group or a spirofluorenyl group; $\alpha^1$ represents a phenylene group or a biphenyldiyl group; $R^{11}$ to $R^{17}$ and $R^{21}$ to $R^{24}$ each independently represent hydrogen, an alkyl group having 1 to 10 carbon atoms, or an aryl group having 6 to 25 carbon atoms; and $R^{31}$ to $R^{35}$ each independently represent hydrogen or an alkyl group having 1 to 10 carbon atoms. The naphthyl group, the fluorenyl group, the spirofluorenyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.

Specific examples of $Ar^1$ in General Formulae (G0) to (G2) include substituents represented by Structural Formulae (2-1) to (2-3).

[Chemical formula 10]

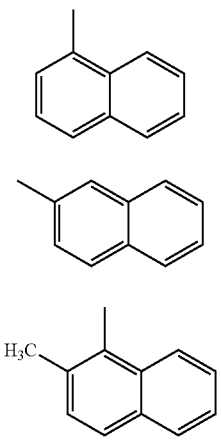

(2-1)

(2-2)

(2-3)

Specific examples of $\alpha^1$ in General Formulae (G0) to (G2) and $\alpha^2$ in General Formula (G0) include substituents represented by Structural Formulae (3-1) to (3-12).

[Chemical formula 11]

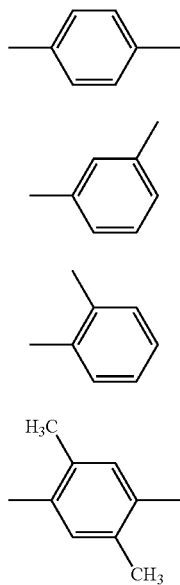

(3-1)

(3-2)

(3-3)

(3-4)

-continued

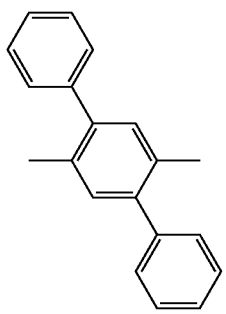

(3-5)

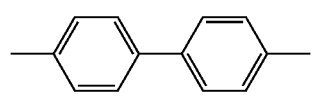

(3-6)

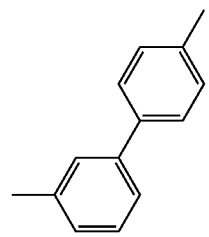

(3-7)

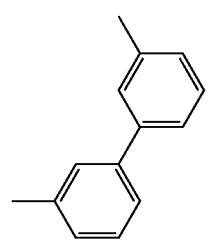

(3-8)

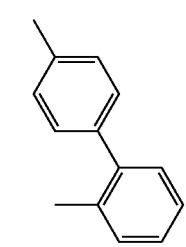

(3-9)

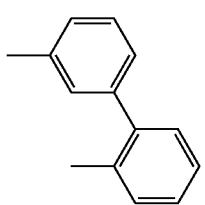

(3-10)

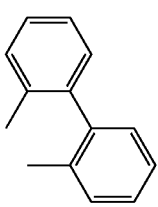

(3-11)

-continued (3-12)
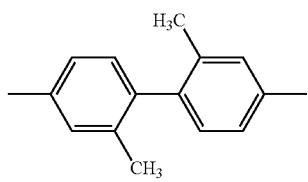

Another embodiment of the present invention is an organic compound represented by General Formula (G3). The organic compound represented by General Formula (G3) is preferred because the synthetic cost can be low.

[Chemical formula 12]

(G3)
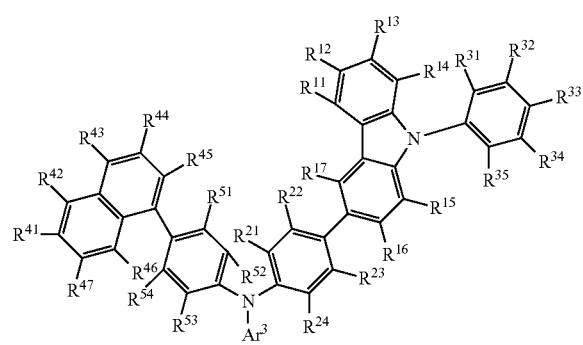

In General Formula (G3), $Ar^3$ represents a fluorenyl group or a spirofluorenyl group; $R^{11}$ to $R^{17}$, $R^{21}$ to $R^{24}$, $R^{41}$ to $R^{47}$, and $R^{51}$ to $R^{54}$ each independently represent hydrogen, an alkyl group having 1 to 10 carbon atoms, or an aryl group having 6 to 25 carbon atoms; and $R^{31}$ to $R^{35}$ each independently represent hydrogen or an alkyl group having 1 to 10 carbon atoms. The fluorenyl group or the spirofluorenyl group is unsubstituted or substituted. In the case where the fluorenyl group or the spirofluorenyl group has a substituent, the substituent is an alkyl group having 1 to 10 carbon atoms or an aryl group having 6 to 25 carbon atoms.

In each of the above General Formulae, specific examples of $Ar^3$ include substituents represented by Structural formulae (4-1) to (4-5).

[Chemical formula 13]

(4-1)
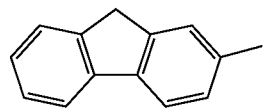

(4-2)
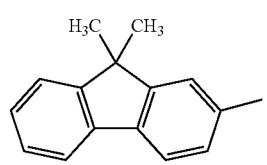

-continued (4-3)

(4-4)
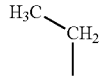

(4-5)
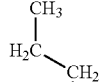

In each of the above General Formulae, when a naphthyl group, a carbazolyl group, a fluorenyl group, a spirofluorenyl group, a phenylene group, or a biphenyldiyl group has a substituent, the substituent is an alkyl group having 1 to 10 carbon atoms or an aryl group having 6 to 25 carbon atoms. Specific examples of the substituent include substituents represented by Structural Formulae (5-1) to (5-31). Specific examples of $R^{11}$ to $R^{17}$, $R^{21}$ to $R^{24}$, $R^{41}$ to $R^{47}$, and $R^{51}$ to $R^{54}$ include substituents represented by Structural Formulae (5-1) to (5-31). Specific examples of $R^{31}$ to $R^{35}$ include substituents represented by Structural Formulae (5-1) to (5-8).

[Chemical formula 14]

(5-1)
CH₃

(5-2)
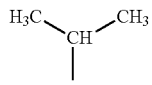

(5-3)
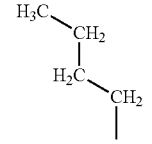

(5-4)

(5-5)

-continued
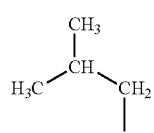 (5-6)
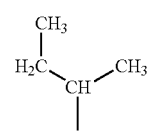 (5-7)
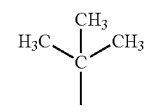 (5-8)
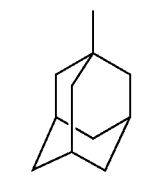 (5-9)
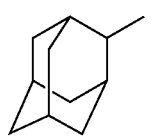 (5-10)
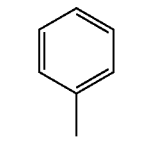 (5-11)
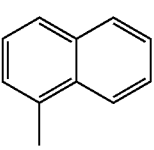 (5-12)
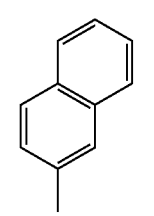 (5-13)
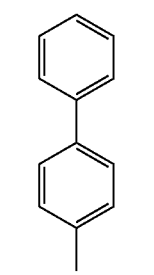 (5-14)
-continued
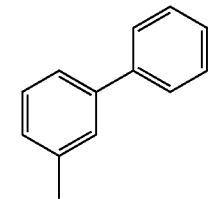 (5-15)
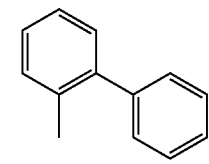 (5-16)
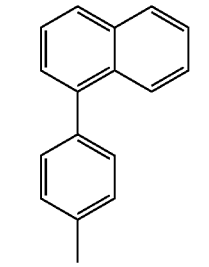 (5-17)
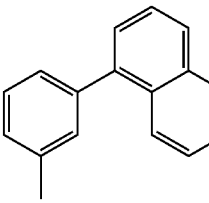 (5-18)
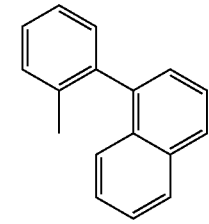 (5-19)
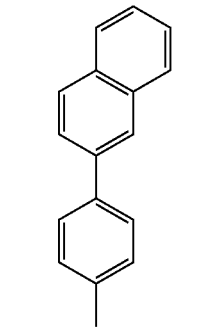 (5-20)

(5-21)
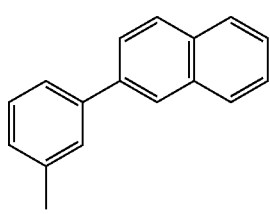
(5-22)
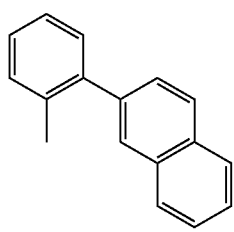
(5-23)
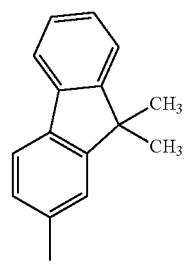
(5-24)
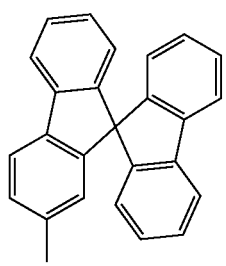
(5-25)
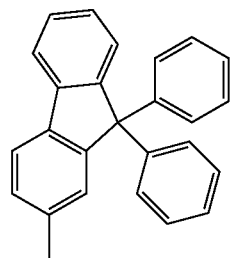
(5-26)
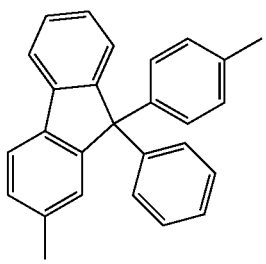
(5-27)
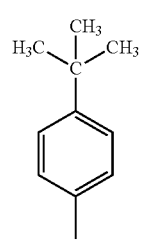
(5-28)
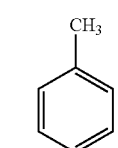
(5-29)
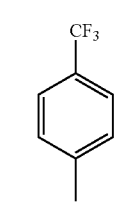
(5-30)
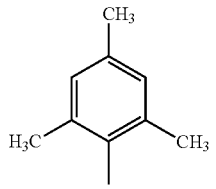
(5-31)
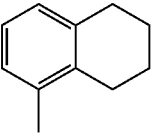
Specific examples of the organic compound represented by General Formula (G0) include organic compounds represented by Structural Formulae (100) to (157). Note that the present invention is not limited to these compounds.

[Chemical formula 15]
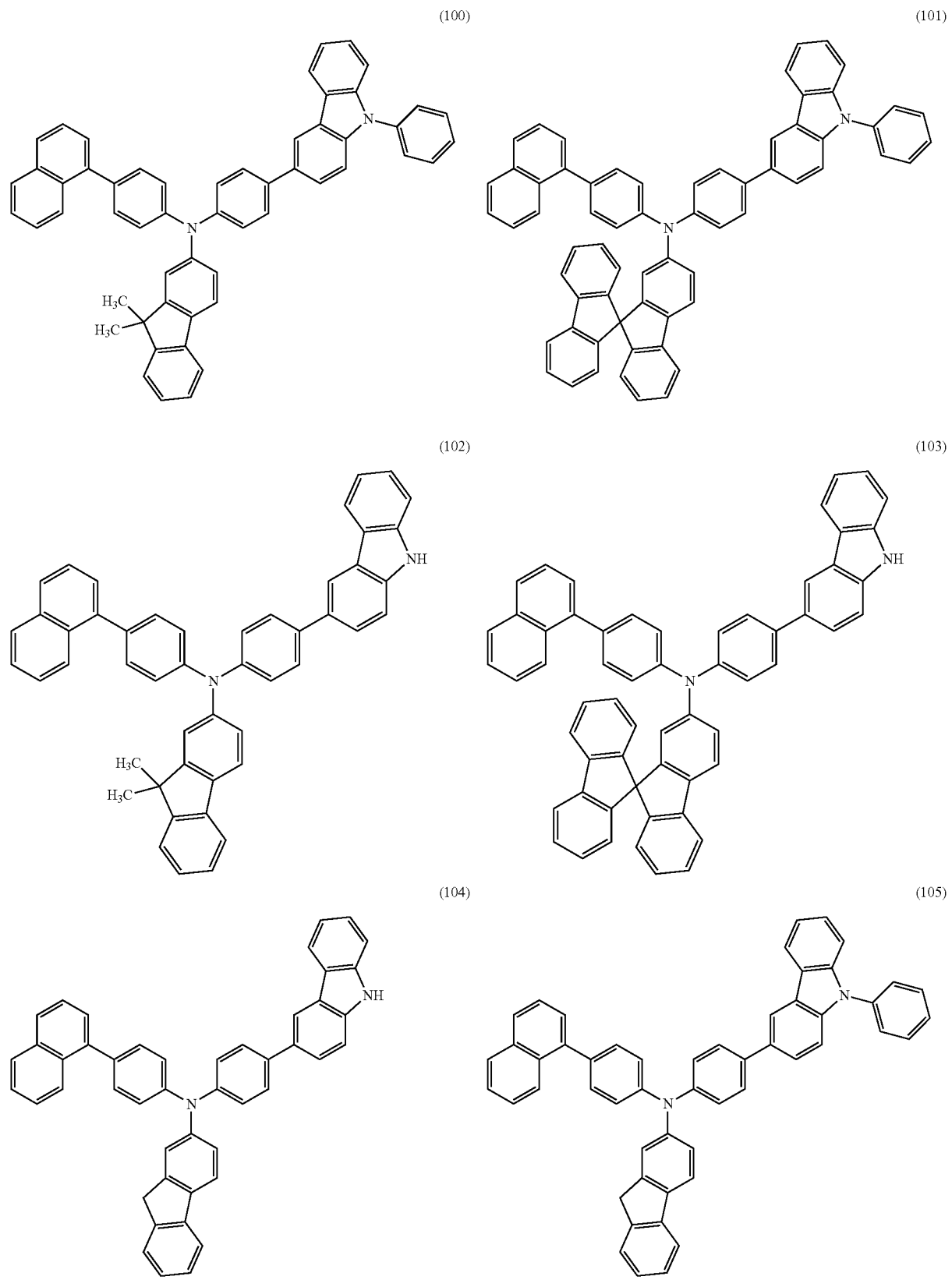

[Chemical formula 16]
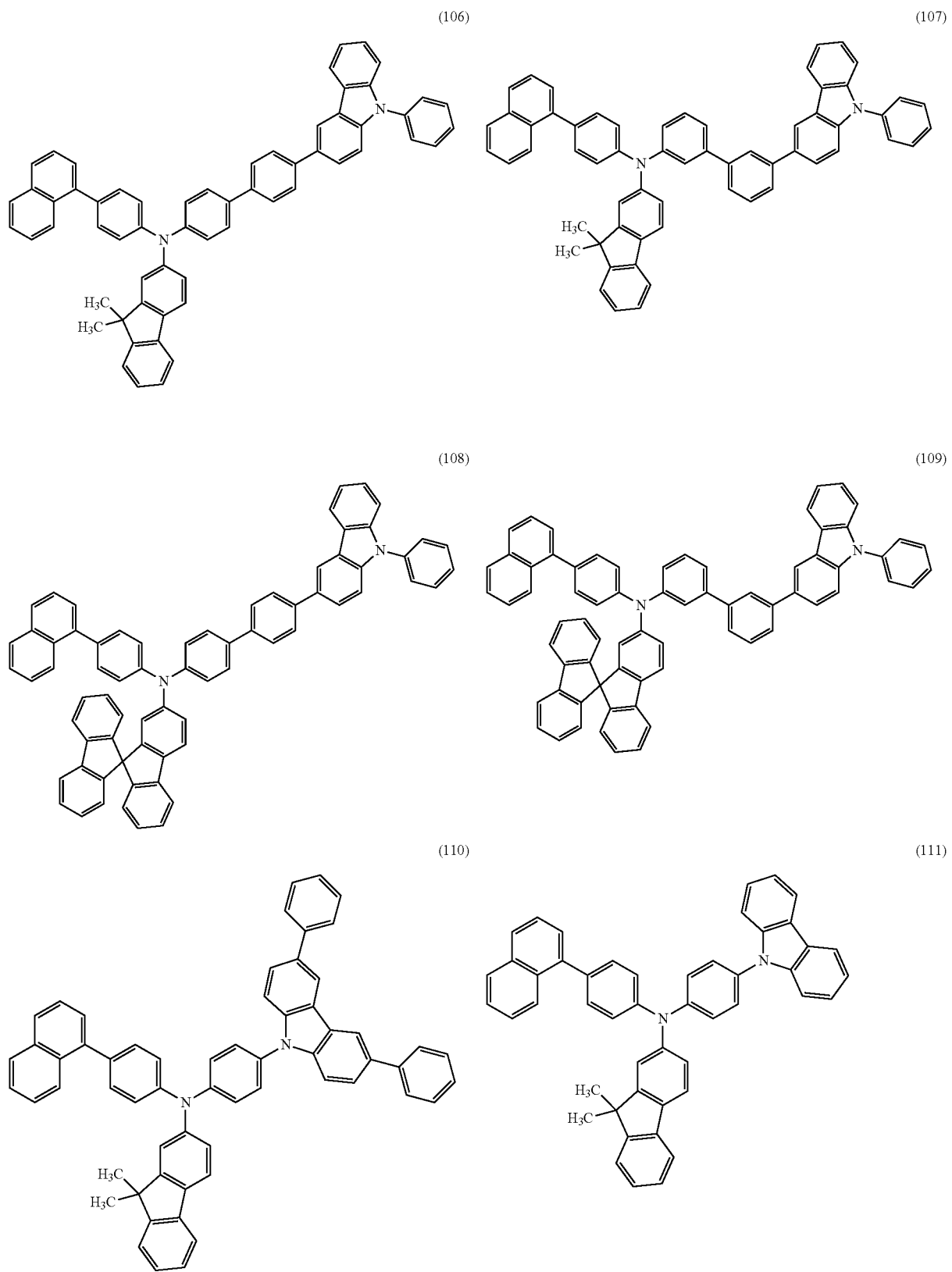

[Chemical formula 17]
(112)
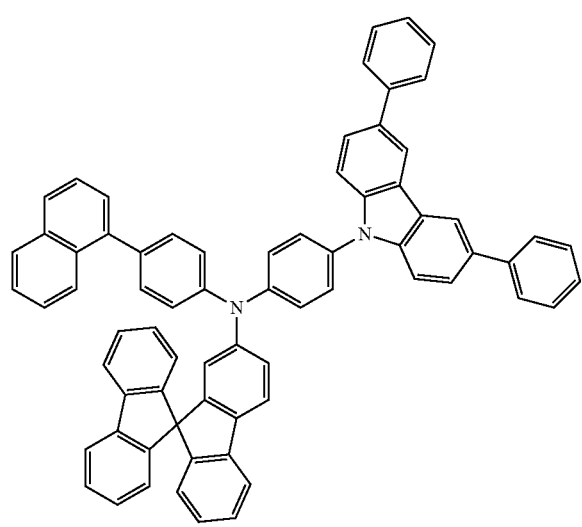
(113)
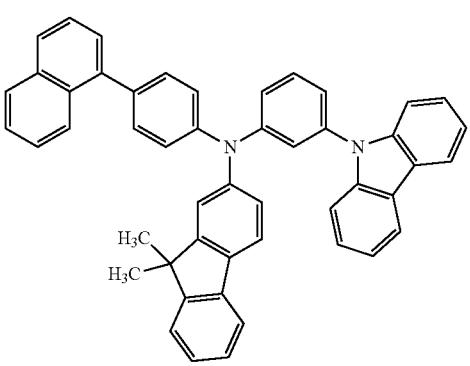
(114)
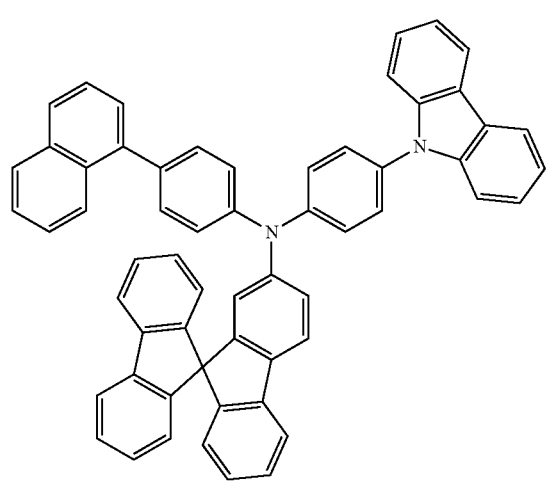
(115)
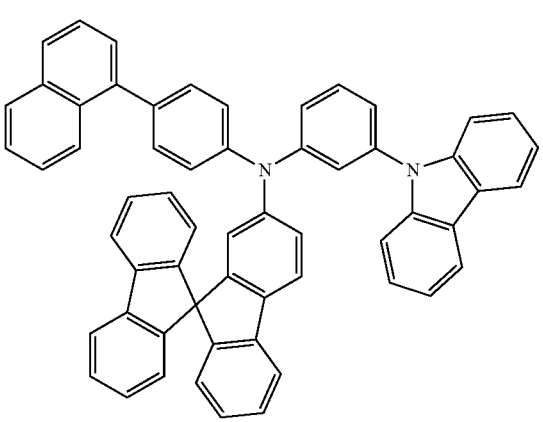
(116)
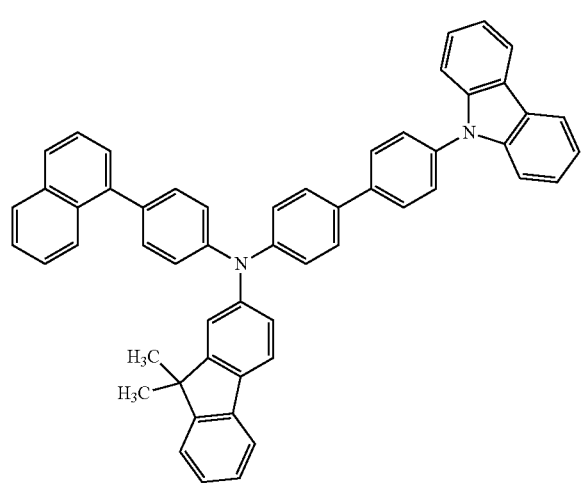
(117)
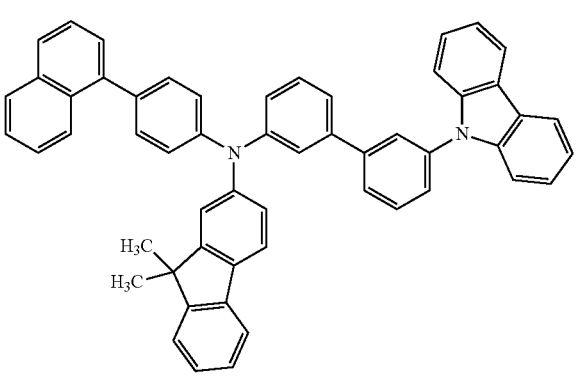

[Chemical formula 18]
(118)
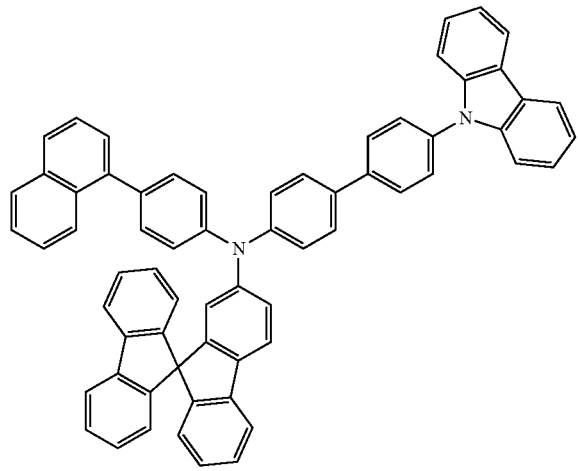
(119)
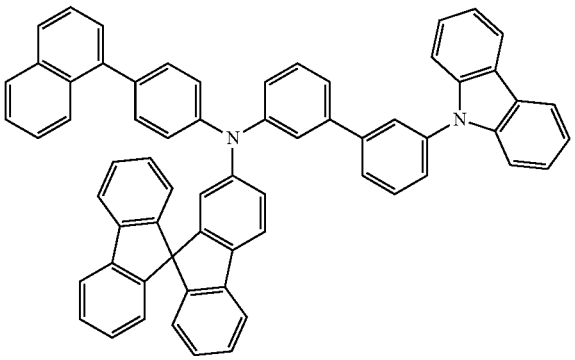
(120)
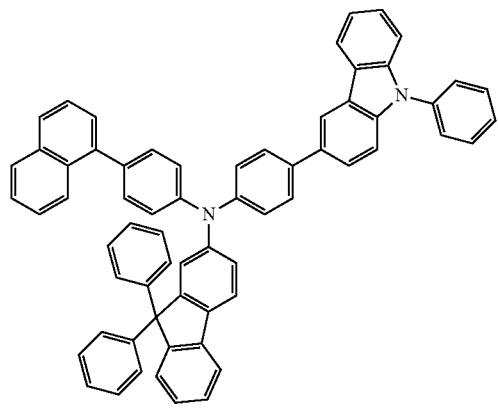
(121)
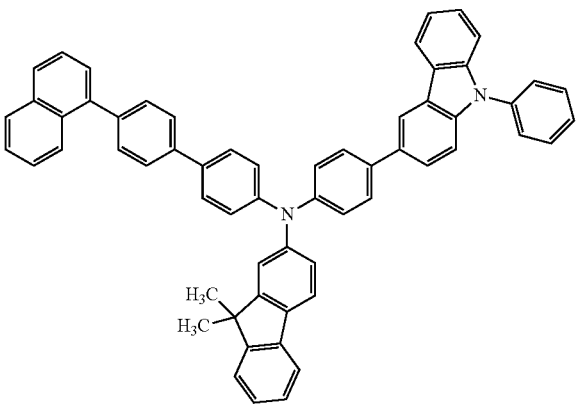
(122)
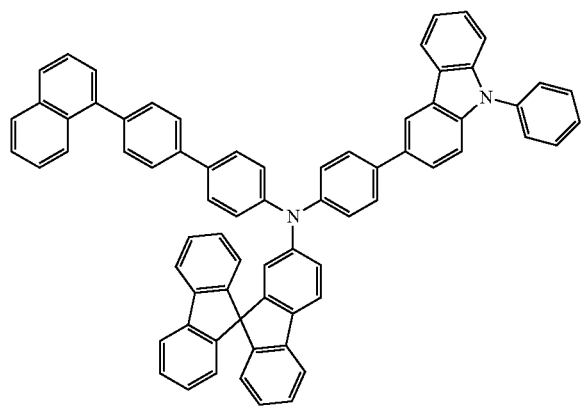
(123)
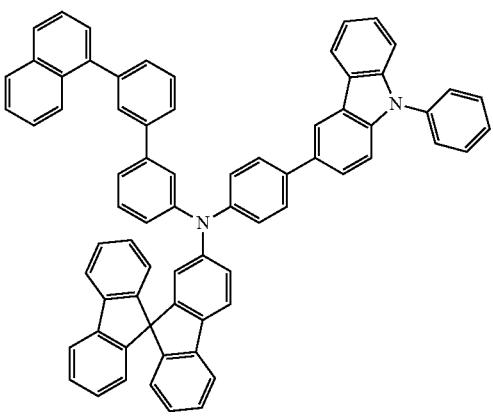

[Chemical formula 19]
(124)
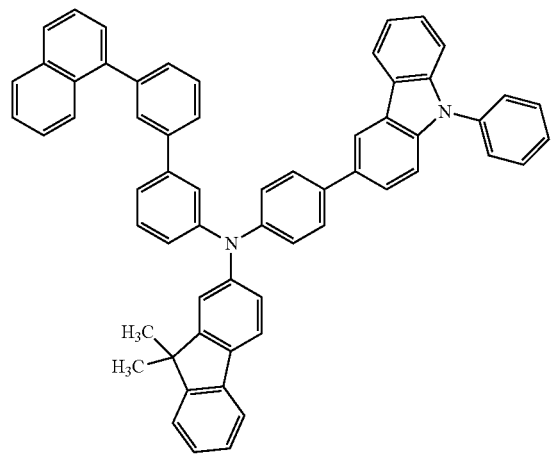
(125)
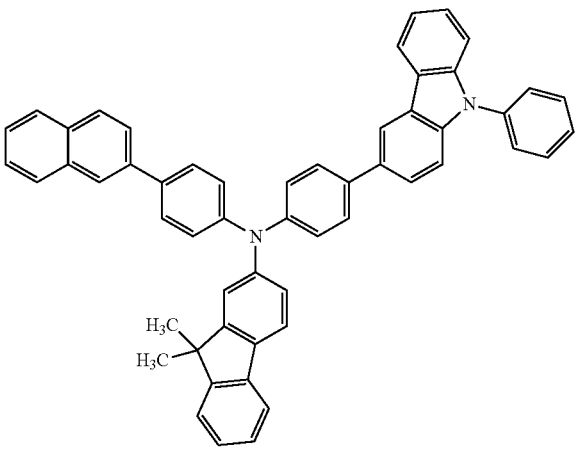
(126)
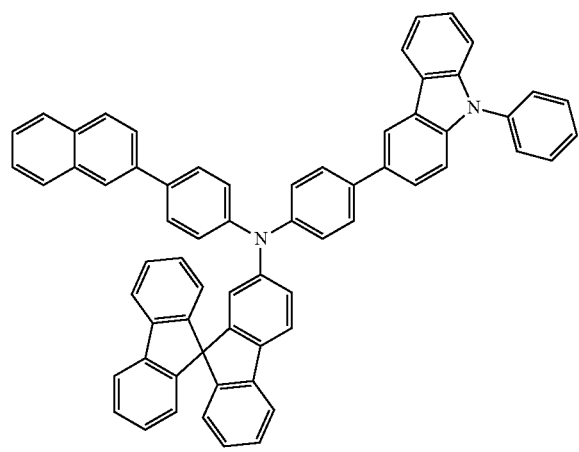
(127)
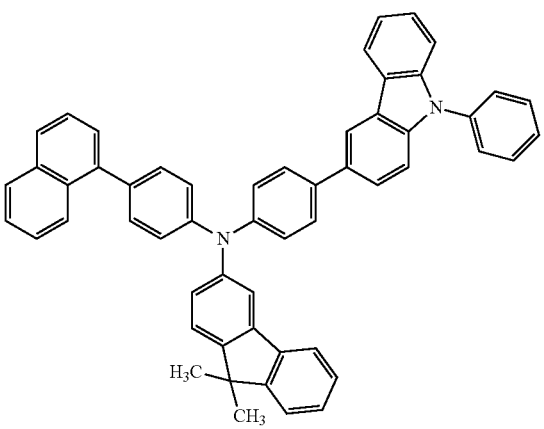
(128)
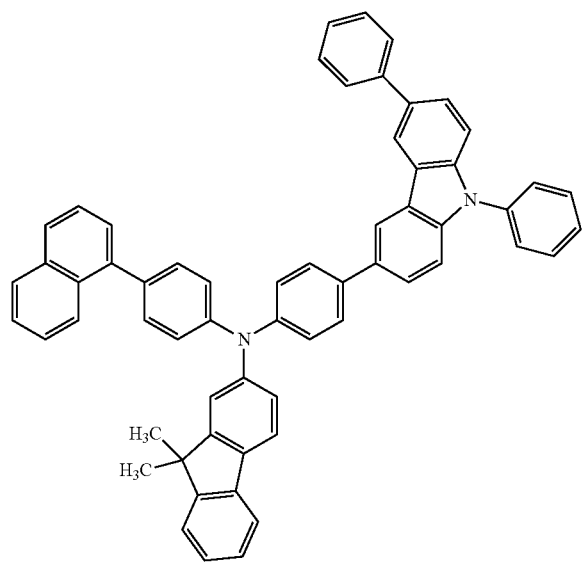

[Chemical formula 20]
(129)
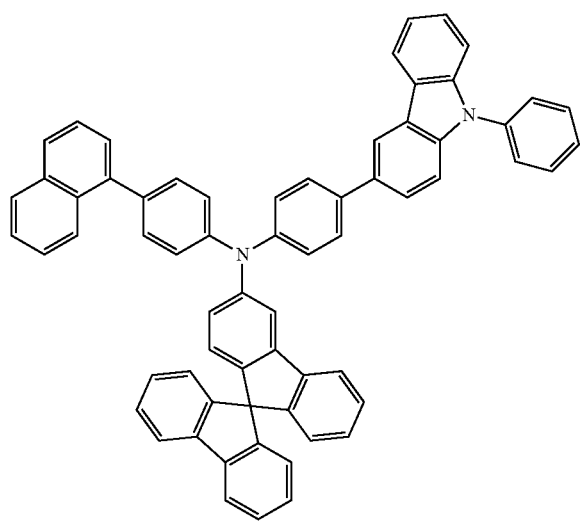
(130)
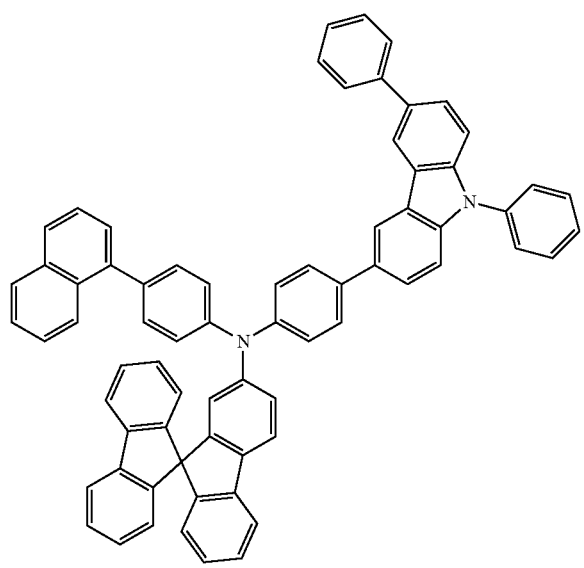
(131)
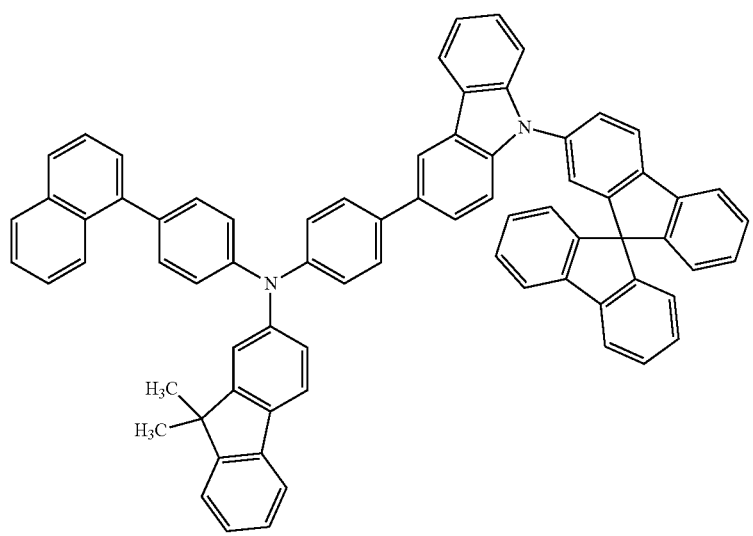
(132)
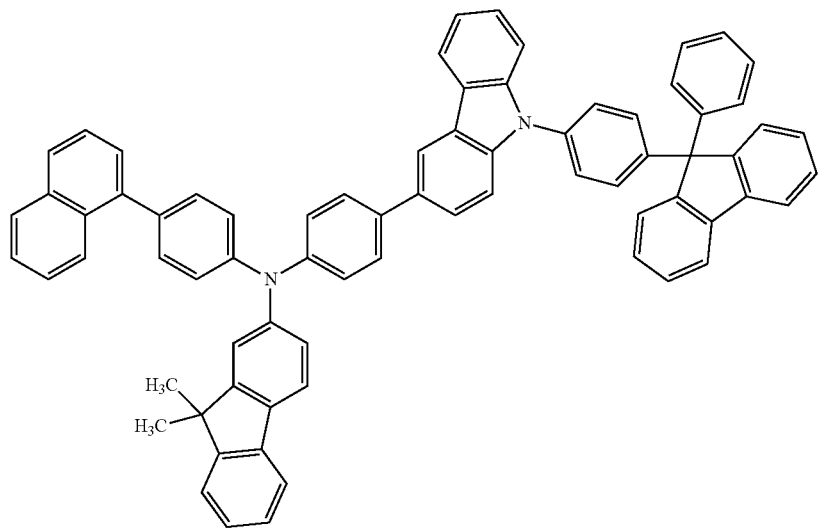

[Chemical formula 21]
(133)
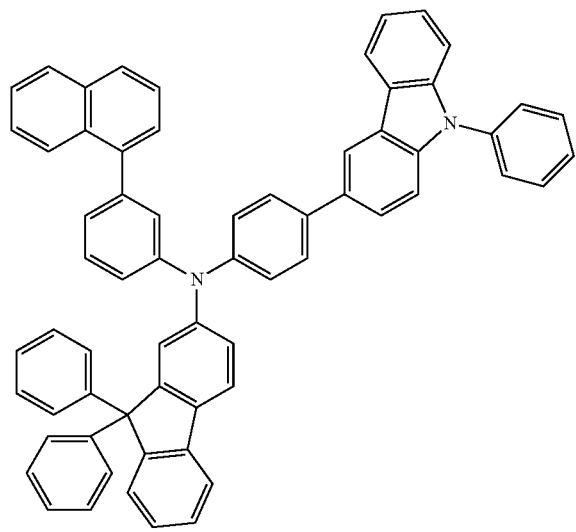
(134)
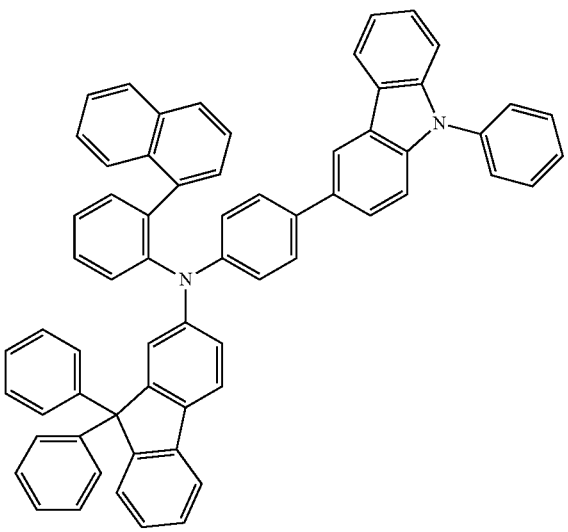
(135)
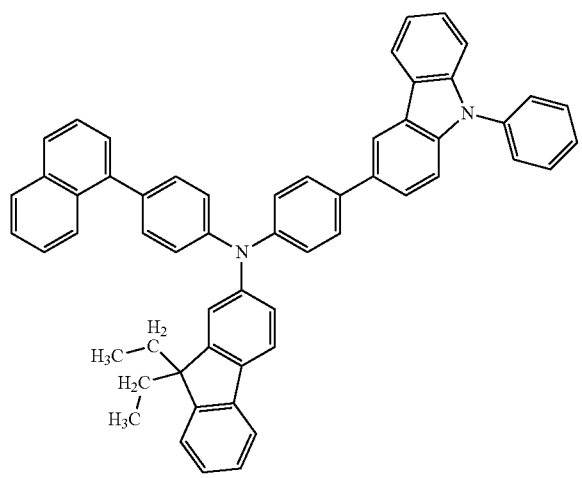
(136)
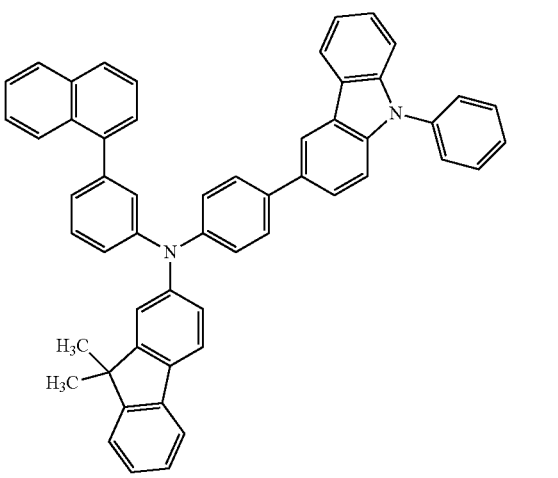
(137)
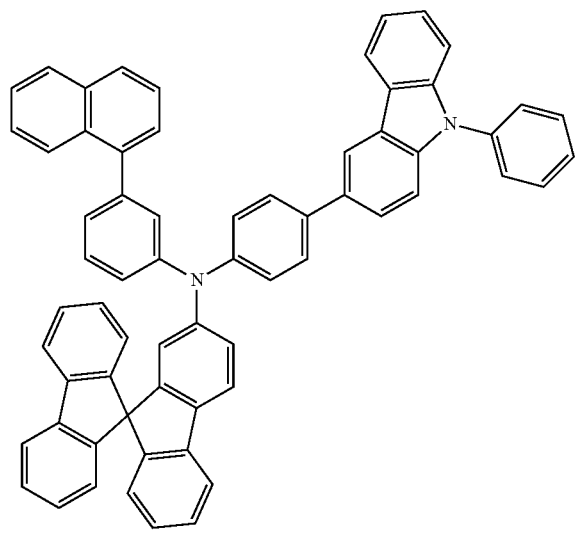
(138)
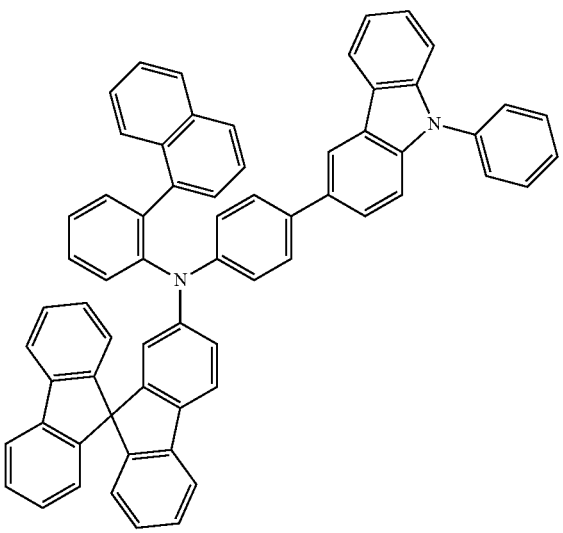

[Chemical formula 22]
(139)
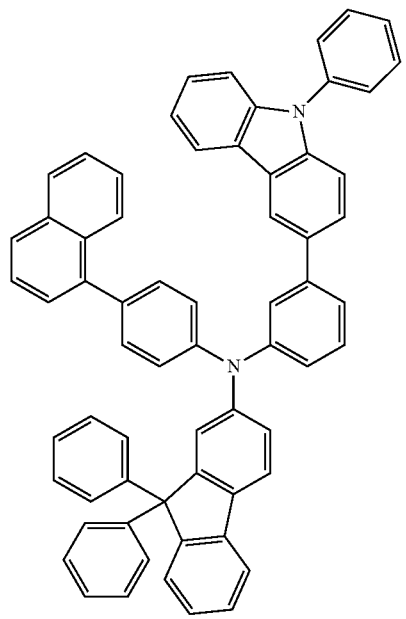
(140)
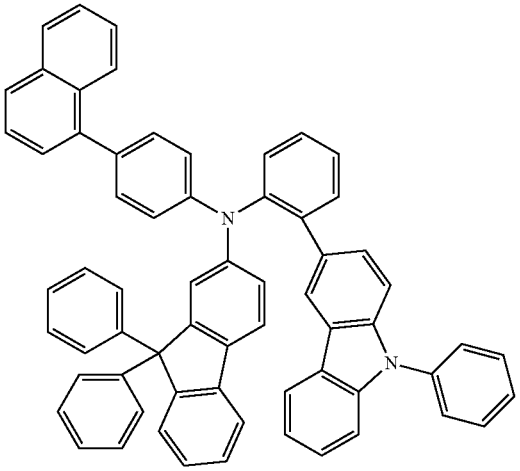
(141)
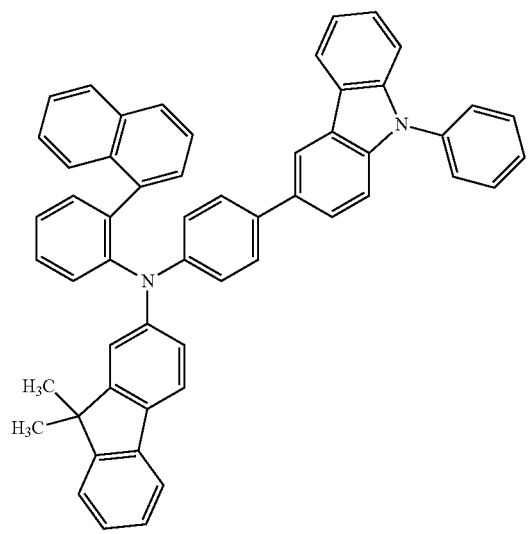
(142)
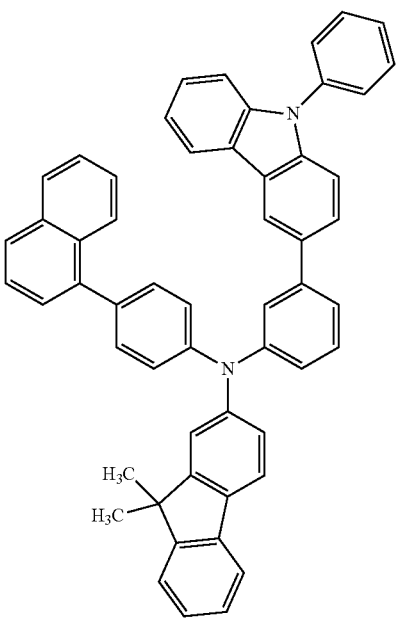

-continued
(143)
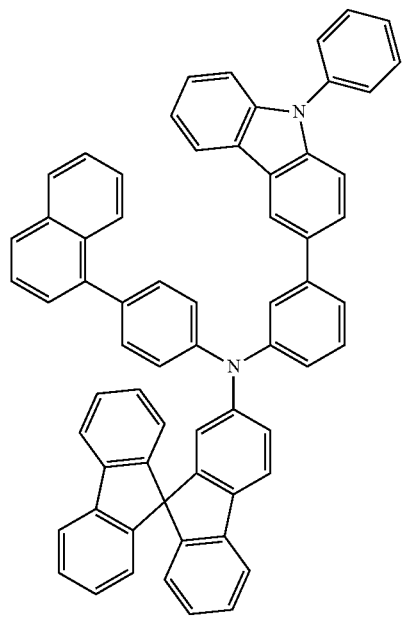
(144)
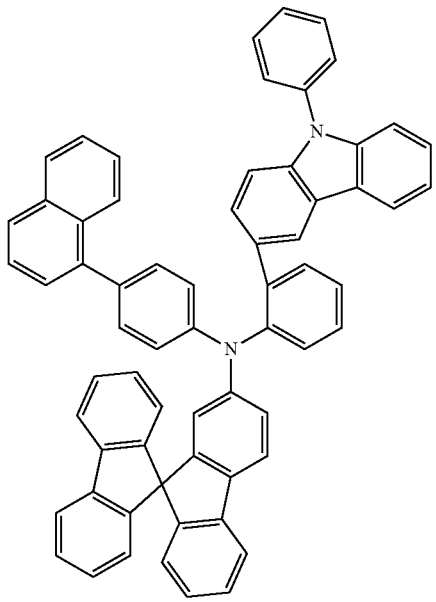
[Chemical formula 23]
(145)
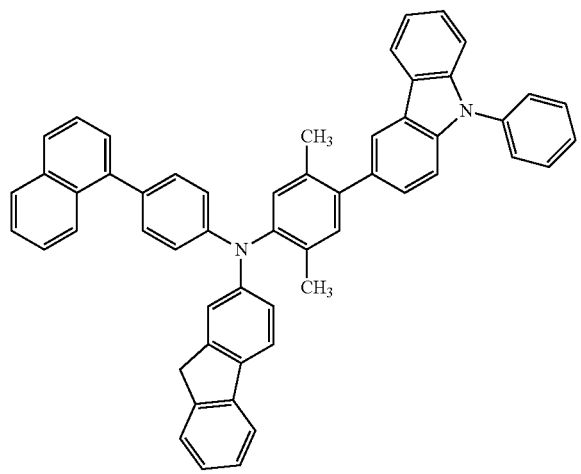
(146)
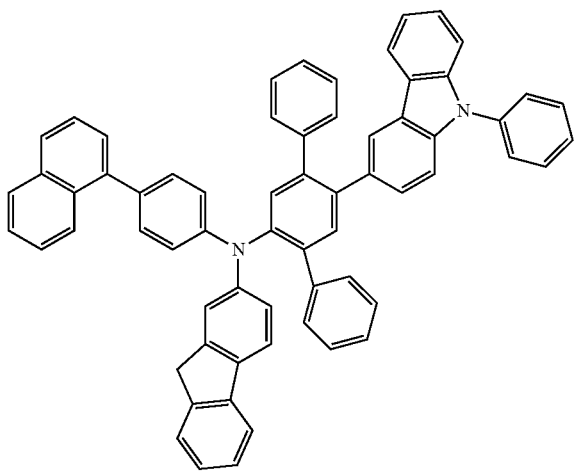
(147)
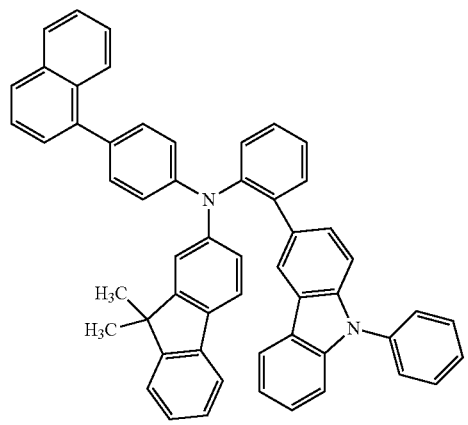
(148)
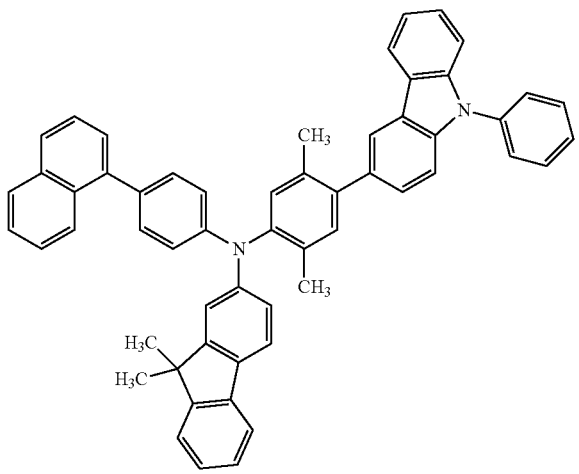

-continued
(149)
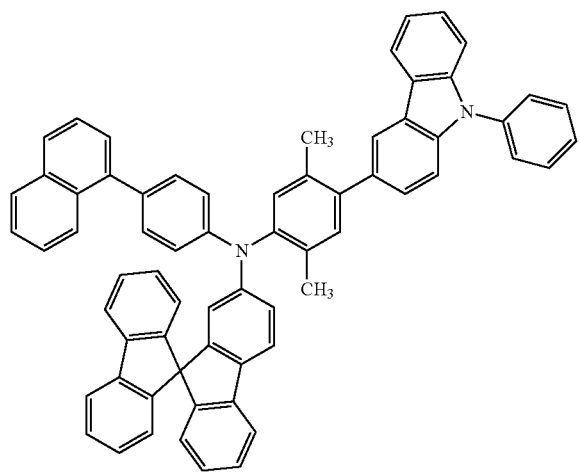
(150)
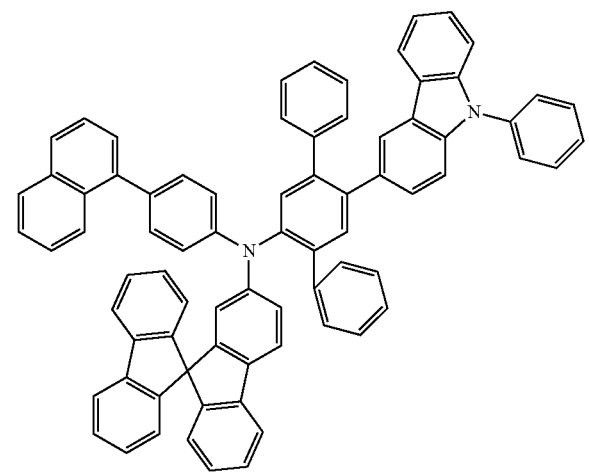
[Chemical formula 24]
(151)
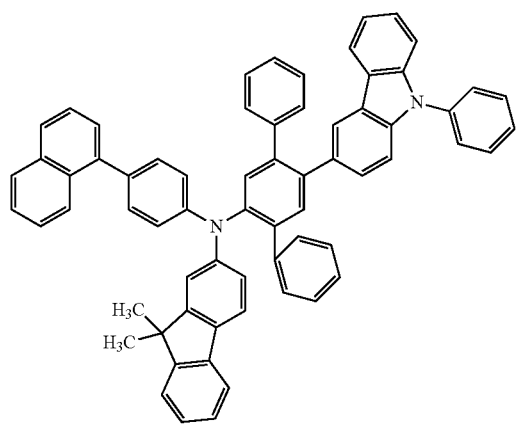
(152)
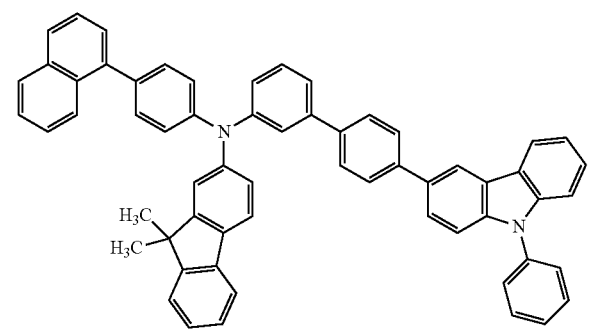
(153)
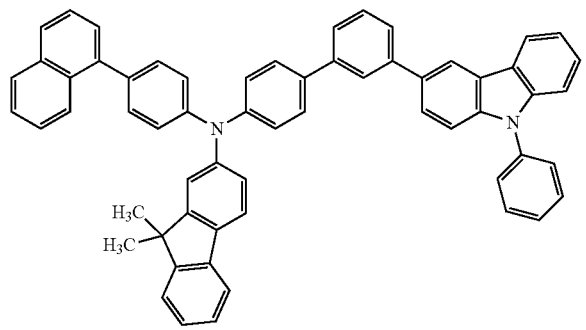
(154)
(155)
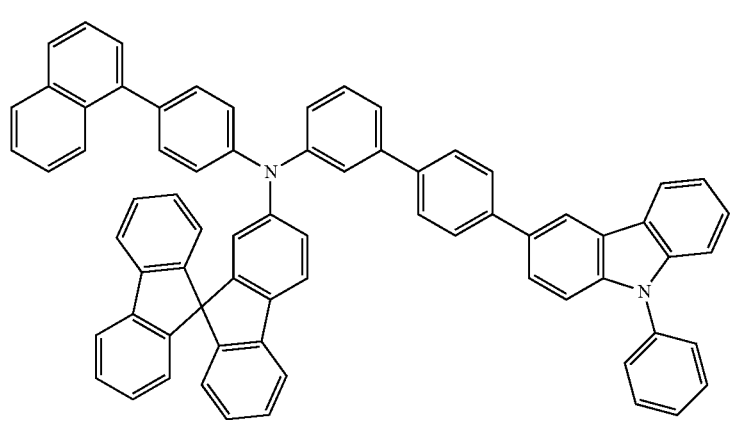

[Chemical formula 25]

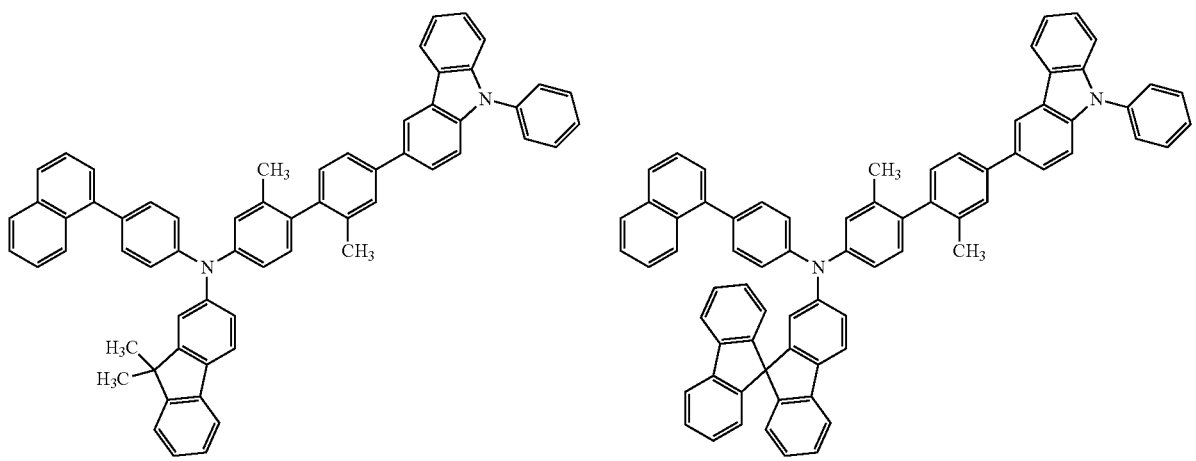

A variety of reactions can be applied to a synthesis method of any of the organic compounds of embodiments of the present invention. For example, Step 1 and Step 2 described below enable the synthesis of the organic compound of one embodiment of the present invention represented by General Formula (G0). Note that the synthesis method of any of the organic compounds of embodiments of the present invention is not limited to the synthesis methods below.

<Step 1>

As shown in Synthesis Scheme (A-1), coupling of primary arylamine (a1) and halogenated aryl (a2) is performed in the presence of a base using a metal catalyst, so that secondary diarylamine (a3) can be obtained.

[Chemical formula 26]

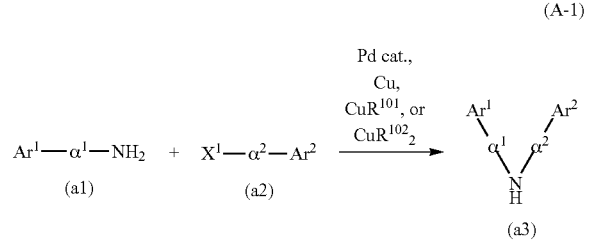

In Synthesis Scheme (A-1), $Ar^1$ represents a naphthyl group; $Ar^2$ represents a carbazolyl group; $\alpha^1$ and $\alpha^2$ each independently represent a phenylene group or a biphenyldiyl group; and $X^1$ represents a halogen group or a trifluoromethanesulfonyl group, preferably represents a bromo group or an iodine group. The naphthyl group, the carbazolyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.

[Case of Performing Buchwald-Hartwig Reaction]

As a palladium catalyst that can be used in Synthesis Scheme (A-1), bis(dibenzylideneacetone)palladium(0) and palladium(II) acetate are given, for example. As a ligand of the palladium catalyst, tris(tert-butyl)phosphine, tri(n-hexyl)phosphine, and tricyclohexylphosphine are given, for example. The catalyst and the ligand which can be used are not limited thereto.

Examples of bases that can be used in Synthesis Scheme (A-1) include an organic base such as sodium tert-butoxide and an inorganic base such as potassium carbonate. Examples of solvents that can be used in Synthesis Scheme (A-1) include toluene, xylene, benzene, and tetrahydrofuran. Note that the base and the solvent which can be used are not limited thereto.

[Case of Performing Ullmann Reaction]

In Synthesis Scheme (A-1), $R^{101}$ and $R^{102}$ each independently represent halogen, an acetyl group, or the like, and as halogen, chlorine, bromine, or iodine can be used. Furthermore, it is preferable to use copper(I) iodide in which $R^{101}$ is iodine or copper(II) acetate in which $R^{102}$ is an acetyl group. The copper compound used for the reaction is not limited thereto. Further, copper can be used other than the copper compound. A base that can be used in Synthesis Scheme (A-1) may be, but not limited to, potassium carbonate. The base that can be used is not limited thereto.

Examples of solvents that can be used in Synthesis Scheme (A-1) include 1,3-dimethyl-3,4,5,6-tetrahydro-2(1H)pyrimidinone (DMPU), toluene, xylene, and benzene. The solvent that can be used is not limited thereto. In the Ullmann reaction, when the reaction temperature is 100° C. or higher, an objective substance can be obtained in a shorter time in a higher yield; therefore, it is preferable to use DMPU, xylene, or toluene each having a high boiling point. The reaction temperature of 150° C. or higher is further preferable; thus, DMPU is more preferably used.

<Step 2>

As shown in Synthesis Scheme (A-2), coupling of secondary diarylamine (a3) and halogenated aryl (a-4) is performed in the presence of a base using a metal catalyst, so that the organic compound represented by General Formula (G0) can be obtained.

[Chemical formula 27]

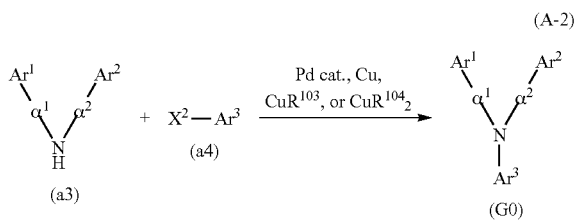

In Synthesis Scheme (A-2), $Ar^1$ represents a naphthyl group; $Ar^2$ represents a carbazolyl group; $Ar^3$ represents a fluorenyl group or a spirofluorenyl group; $\alpha^1$ and $\alpha^2$ each independently represent a phenylene group or a biphenyldiyl group; and $X^2$ represents a halogen group or a trifluoromethanesulfonyl group, preferably represents a bromo group or an iodine group. The naphthyl group, the carbazolyl group, the fluorenyl group, the spirofluorenyl group, the phenylene group, and the biphenyldiyl group are each independently unsubstituted or substituted. In the case where any of the groups has a substituent, the substituent is an alkyl group having 1 to 10 carbon atoms or an aryl group having 6 to 25 carbon atoms.

[Case of Performing Buchwald-Hartwig Reaction]

In the case of performing the Buchwald-Hartwig reaction, a palladium catalyst, a ligand of the palladium catalyst, a base, and a solvent which can be used in Synthesis Scheme (A-2) can be similar to those in Synthesis Scheme (A-1).

[Case of Performing Ullmann Reaction]

In Synthesis Scheme (A-2), $R^{103}$ and $R^{104}$ each independently represent halogen, an acetyl group, or the like, and as halogen, chlorine, bromine, or iodine can be used. Furthermore, it is preferable to use copper(I) iodide in which $R^{103}$ is iodine or copper(II) acetate in which $R^{104}$ is an acetyl group. The copper compound used for the reaction is not limited thereto. Further, copper can be used other than the copper compound.

A base and a solvent which can be used in Synthesis Scheme (A-2) can be similar to those in Synthesis Scheme (A-1).

Through the above-described steps, the organic compound of this embodiment can be synthesized.

The organic compound of this embodiment has a high hole-transport property and thus can be suitably used as a material for a hole-transport layer of a light-emitting element. Furthermore, in the light-emitting element, the organic compound can be suitably used as a host material that disperses light-emitting substances in a light-emitting layer. The light-emitting layer may contain a light-emitting substance and a host material having a high electron-transport property, and may further contain the organic compound of this embodiment as an assist material. With the use of the organic compound of this embodiment, a long-lifetime light-emitting element can be achieved. Furthermore, with the use of the light-emitting element, a light-emitting device, an electronic device, and a lighting device each having high reliability can be obtained.

This embodiment can be freely combined with any of the other embodiments.

Embodiment 2

In this embodiment, a light-emitting element of one embodiment of the present invention will be described with reference to FIGS. 1A and 1B.

The light-emitting element described in this embodiment includes a pair of electrodes (a first electrode and a second electrode) and a layer containing a light-emitting organic compound (EL layer) provided between the pair of electrodes. One of the pair of electrodes serves as an anode and the other serves as a cathode.

Specific examples of a structure of the light-emitting element of one embodiment of the present invention are described below.

A light-emitting element illustrated in FIG. 1A includes an EL layer 203 between a first electrode 201 and a second electrode 205. In this embodiment, the first electrode 201 serves as an anode and the second electrode 205 serves as a cathode.

When a voltage higher than the threshold voltage of the light-emitting element is applied between the first electrode 201 and the second electrode 205, holes are injected from the first electrode 201 side to the EL layer 203 and electrons are injected from the second electrode 205 side to the EL layer 203. The injected electrons and holes are recombined in the EL layer 203 and a light-emitting substance contained in the EL layer 203 emits light.

The EL layer 203 includes at least a light-emitting layer containing a light-emitting substance. In addition to the light-emitting layer, the EL layer 203 may further include one or more layers containing any of a substance with a high hole-injection property, a substance with a high hole-transport property, a hole-blocking material, a substance with a high electron-transport property, a substance with a high electron-injection property, a substance with a bipolar property (a substance with a high electron-transport property and a high hole-transport property), and the like.

A known substance can be used for the EL layer 203. Either a low molecular compound or a high molecular compound can be used, and an inorganic compound may be contained in the EL layer 203. In this embodiment, the EL layer 203 contains the organic compound of one embodiment of the present invention. The organic compound of one embodiment of the present invention has a high hole-transport property, and thus can be used for a hole-transport layer or a light-emitting layer.

A specific example of a structure of the EL layer 203 is illustrated in FIG. 1B. In the EL layer 203 illustrated in FIG. 1B, a hole-injection layer 301, a hole-transport layer 302, a light-emitting layer 303, an electron-transport layer 304, and an electron-injection layer 305 are stacked in this order from the first electrode 201 side.

A light-emitting element illustrated in FIG. 1C includes the EL layer 203 between the first electrode 201 and the second electrode 205, and further includes an intermediate layer 207 between the EL layer 203 and the second electrode 205.

A specific example of a structure of the intermediate layer 207 is illustrated in FIG. 1D. The intermediate layer 207 includes at least a charge-generation region 308. In addition to the charge-generation region 308, the intermediate layer 207 may further include an electron-relay layer 307 and an electron-injection buffer layer 306. In FIG. 1D, the EL layer 203 is provided over the first electrode 201, the intermediate layer 207 is provided over the EL layer 203, and the second electrode 205 is provided over the intermediate layer 207. Also in FIG. 1D, as the intermediate layer 207, the electron-injection buffer layer 306, the electron-relay layer 307, and the charge-generation region 308 are provided in this order from the EL layer 203 side.

When a voltage higher than the threshold voltage of the light-emitting element is applied between the first electrode 201 and the second electrode 205, holes and electrons are generated in the charge-generation region 308, and the holes move into the second electrode 205 and the electrons move into the electron-relay layer 307. The electron-relay layer 307 has a high electron-transport property and immediately transfers the electrons generated in the charge-generation region 308 to the electron-injection buffer layer 306. The electron-injection buffer layer 306 reduces a barrier against electron injection into the EL layer 203, so that the efficiency of the electron injection into the EL layer 203 can be improved. Thus, the electrons generated in the charge-generation region 308 are injected into the lowest unoccupied molecular orbital (LUMO) level of the EL layer 203 through the electron-relay layer 307 and the electron-injection buffer layer 306.

In addition, the electron-relay layer 307 can prevent reaction at the interface between a material contained in the charge-generation region 308 and a material contained in the electron-injection buffer layer 306. Thus, it is possible to prevent interaction such as damaging the functions of the charge-generation region 308 and the electron-injection buffer layer 306.

As illustrated in light-emitting elements in FIGS. 1E and 1F, a plurality of EL layers may be stacked between the first electrode 201 and the second electrode 205. In that case, the intermediate layer 207 is preferably provided between the stacked EL layers. For example, the light-emitting element illustrated in FIG. 1E includes the intermediate layer 207 between a first EL layer 203a and a second EL layer 203b. The light-emitting element illustrated in FIG. 1F includes n EL layers is a natural number of 2 or more). The light-emitting element illustrated in FIG. 1F includes the intermediate layer 207 between an m-th EL layer 203(m) and an (m+1)-th EL layer 203(m+1).

The following will show behaviors of electrons and holes in the intermediate layer 207 between the EL layer 203(m) and the EL layer 203(m+1). When a voltage higher than the threshold voltage of the light-emitting element is applied between the first electrode 201 and the second electrode 205, holes and electrons are generated in the intermediate layer 207, and the holes move into the EL layer 203(m+1) provided on the second electrode 205 side and the electrons move into the EL layer 203(m) provided on the first electrode 201 side. The holes injected into the EL layer 203(m+1) are recombined with the electrons injected from the second electrode 205 side, so that a light-emitting substance contained in the EL layer 203(m+1) emits light. Further, the electrons injected into the EL layer 203(m) are recombined with the holes injected from the first electrode 201 side, so that a light-emitting substance contained in the EL layer 203(m) emits light. Thus, the holes and electrons generated in the intermediate layer 207 cause light emission in the respective EL layers.

Note that the EL layers can be provided in contact with each other as long as the same structure as the intermediate layer is formed therebetween. For example, when the charge-generation region is formed over one surface of an EL layer, another EL layer can be provided in contact with the surface.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. That is, white light emission can be obtained by mixture of light from materials whose emission colors are complementary colors. This can be applied to a light-emitting element having three or more EL layers.

FIGS. 1A to 1F can be used in an appropriate combination. For example, the intermediate layer 207 can be provided between the second electrode 205 and the EL layer 203(n) in FIG. 1F.

Examples of materials which can be used for each layer will be described below. Note that each layer is not limited to a single layer, and may be a stack of two or more layers.
<Anode>

The electrode serving as the anode (the first electrode 201 in this embodiment) can be formed using one or more kinds of conductive metals, alloys, conductive compounds, and the like. In particular, it is preferable to use a material with a high work function (4.0 eV or more). Examples include indium tin oxide (ITO), indium tin oxide containing silicon or silicon oxide, indium zinc oxide, indium oxide containing tungsten oxide and zinc oxide, graphene, gold, platinum, nickel, tungsten, chromium, molybdenum, iron, cobalt, copper, palladium, and a nitride of a metal material (e.g., titanium nitride).

When the anode is in contact with the charge-generation region, any of a variety of conductive materials can be used regardless of their work functions; for example, aluminum, silver, or an alloy containing aluminum can be used.
<Cathode>

The electrode serving as the cathode (the second electrode 205 in this embodiment) can be formed using one or more kinds of conductive metals, alloys, conductive compounds, and the like. In particular, it is preferable to use a material with a low work function (3.8 eV or less). Examples include aluminum, silver, an element belonging to Group 1 or 2 of the periodic table (e.g., an alkali metal such as lithium or cesium, an alkaline earth metal such as calcium or strontium, or magnesium), an alloy containing any of these elements (e.g., Mg—Ag or Al—Li), a rare earth metal such as europium or ytterbium, and an alloy containing any of these rare earth metals.

When the cathode is in contact with the charge-generation region, any of a variety of conductive materials can be used regardless of their work functions; for example, ITO or indium tin oxide containing silicon or silicon oxide can be used.

The light-emitting element may have a structure in which one of the anode and the cathode is formed using a conductive film that transmits visible light and the other is formed using a conductive film that reflects visible light, or a structure in which both the anode and the cathode are formed using conductive films that transmit visible light.

The conductive film that transmits visible light can be formed using, for example, indium oxide, ITO, indium zinc oxide, zinc oxide, or zinc oxide to which gallium is added. Alternatively, a film of a metal material such as gold, platinum, nickel, tungsten, chromium, molybdenum, iron, cobalt, copper, palladium, or titanium, or a nitride of any of these metal materials (e.g., titanium nitride) can be formed thin so as to have a light-transmitting property. Further alternatively, graphene or the like may be used.

The conductive film that reflects visible light can be formed using, for example, a metal material such as aluminum, gold, platinum, silver, nickel, tungsten, chromium, molybdenum, iron, cobalt, copper, or palladium; an aluminum-containing alloy (aluminum alloy) such as an alloy of aluminum and titanium, an alloy of aluminum and nickel, or an alloy of aluminum and neodymium; or a silver-containing alloy such as an alloy of silver and copper. An alloy of silver and copper is preferable because of its high heat resistance. Further, lanthanum, neodymium, or germanium may be added to the metal material or the alloy.

The electrodes may be formed separately by a vacuum evaporation method or a sputtering method. Alternatively, when a silver paste or the like is used, a coating method or an inkjet method may be used.

<Hole-Injection Layer 301>

The hole-injection layer 301 contains a substance with a high hole-injection property.

Examples of the substance with a high hole-injection property include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Alternatively, it is possible to use a phthalocyanine-based compound such as phthalocyanine (abbreviation: $H_2Pc$) or copper(II) phthalocyanine (abbreviation: CuPc).

Further alternatively, it is possible to use an aromatic amine compound which is a low molecular organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

Further alternatively, it is possible to use a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD), or a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS).

The hole-injection layer 301 may serve as the charge-generation region. When the hole-injection layer 301 in contact with the anode serves as the charge-generation region, a variety of conductive materials can be used for the anode regardless of their work functions. Materials contained in the charge-generation region will be described later.

<Hole-transport Layer 302>

The hole-transport layer 302 contains a substance with a high hole-transport property. The organic compound of one embodiment of the present invention has a high hole-transport property, and thus can be suitably used for the hole-transport layer 302.

The substance with a high hole-transport property is preferably a substance with a property of transporting more holes than electrons, and is especially preferably a substance with a hole mobility of $10^{-6}$ cm$^2$/V·s or more.

For the hole-transport layer 302, it is possible to use an aromatic amine compound such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB).

Alternatively, it is possible to use a carbazole derivative such as 4,4'-di(N-carbazolyl)biphenyl (abbreviation: CBP), 9-[4-(10-phenyl-9-anthracenyl)phenyl]-9H-carbazole (abbreviation: CzPA), or 9-phenyl-3-[4-(10-phenyl-9-anthryl)phenyl]-9H-carbazole (abbreviation: PCzPA).

Further alternatively, it is possible to use an aromatic hydrocarbon compound such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth).

Further alternatively, it is possible to use a high molecular compound such as PVK, PVTPA, PTPDMA, or Poly-TPD.

<Light-Emitting Layer 303>

The light-emitting layer 303 contains a light-emitting substance. As the light-emitting substance, a fluorescent compound which emits fluorescence or a phosphorescent compound which emits phosphorescence can be used.

Examples of fluorescent compounds that can be used for the light-emitting layer 303 are given. Examples of materials that emit blue light are as follows: N,N'-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA). Examples of materials that emit green light are as follows: N-(9,10-diphenyl-2-anthryl)-N,9-diphenyl-9H-carbazol-3-amine (abbreviation: 2PCAPA), N-[9,10-bis(1,1-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA). Examples of materials that emit yellow light are as follows: rubrene and 5,12-bis(1,1'-biphenyl-4-yl)-6,11-diphenyltetracene (abbreviation: BPT). Examples of materials that emit red light are as follows: N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-α]fluoranthene-3,10-diamine (abbreviation: p-mPhAFD).

Examples of phosphorescent compounds that can be used for the light-emitting layer 303 are given. For example, a phosphorescent compound having an emission peak at 440 nm to 520 nm is given, examples of which include organometallic iridium complexes having 4H-triazole skeletons, such as tris{2-[5-(2-methylphenyl)-4-(2,6-dimethylphenyl)-4H-1,2,4-triazol-3-yl-kN$^2$]phenyl-k C}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenylyl)-5-isopropyl-3-phenyl-4H-1,2,4-triazolato]iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having imidazole skeletons, such as fac-tris[1-(2,6-diisopropylphenyl)-2-phenyl-1H-imidazole]iridium(III) (abbreviation: [Ir(iPrpm1)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which aphenylpyridine derivative having an electron-withdrawing group is a ligand, such as bis[2-(4',6'-difluorophenyl)pyridinato-N,C$^{2'}$]iridium (III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ ppy)$_2$(pic)]), and bis[2-(4',6'-difluorophenyl)pyridinato-N,C$^{2'}$]iridium(III)acetylacetonate (abbreviation: FIracac). Among the materials given above, the organometallic iridium complex having a 4H-triazole skeleton has high reliability and high emission efficiency and is thus especially preferable.

Examples of the phosphorescent compound having an emission peak at 520 nm to 600 nm include organometallic iridium complexes having pyrimidine skeletons, such as tris (4-methyl-6-phenylpyrimidinato)iridium(III) (abbreviation: [Ir(mppm)$_3$]), tris(4-t-butyl-6-phenylpyrimidinato)iridium (III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[4-(2-norbornyl)-6-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III)acetylacetonate (abbreviation: [Ir(ppy)$_2$(acac)]), bis (benzo[h]quinolinato)iridium(III)acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$) iridium(III) (abbreviation: [Ir(pq)$_3$]), and bis(2-phenylquinolinato-N,C$^{2'}$)iridium(III)acetylacetonate (abbreviation: [Ir(pq)$_2$(acac)]); and a rare earth metal complex such as tris (acetylacetonato) (monophenanthroline)terbium(III) (abbreviation: [Tb(acac)$_3$(Phen)]).

Examples of the phosphorescent material having an emission peak at 600 nm to 700 nm include organometallic iridium complexes having pyrimidine skeletons, such as (diisobutyrylmethanato)bis[4,6-bis(3-methylphenyl)pyrimidinato] iridium(III) (abbreviation: [Ir(5mdppm)$_2$(dibm)]), bis[4,6-bis(3-methylphenyl)pyrimidinato](dipivaloylmethanato) iridium(III) (abbreviation: [Ir(5mdppm)$_2$(dpm)]D, and bis[4,6-di(naphthalen-1-yl)pyrimidinato](dipivaloylmethanato) iridium(III) (abbreviation: [Ir(d1npm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), or (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N, C$^{2'}$)iridium(I11) (abbreviation: [Ir(piq)$_3$]) and bis(1-phenylisoquinolinato-N,C$^{2'}$)iridium(III)acetylacetonate (abbreviation: [Ir(piq)$_2$(acac)]); a platinum complex such as 2,3,7,8, 12,13,17,18-octaethyl-21H,23H-porphyrin platinum(II) (abbreviation: PtOEP); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). Among the materials given above, the organometallic iridium complex having a pyrimidine skeleton has distinctively high reliability and emission efficiency and is thus especially preferable. Furthermore, the organometallic iridium complex having a pyrazine skeleton can provide red light emission with favorable chromaticity.

Alternatively, a high molecular compound can be used for the light-emitting layer 303. Examples of the materials that emit blue light include poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: PF-DMOP), and poly{(9,9-dioctylfluorene-2,7-diyl)-co-[N, M-di-(p-butylphenyl)-1,4-diaminobenzene]} (abbreviation: TAB-PFH). Examples of the materials that emit green light include poly(p-phenylenevinylene) (abbreviation: PPV), poly[(9,9-dihexylfluorene-2,7-diyl)-alt-co-(benzo[2,1,3] thiadiazole-4,7-diyl)] (abbreviation: PFBT), and poly[(9,9-dioctylfluorene-2,7-divinylenefluorenylene)-alt-co-(2-methoxy-5-(2-ethylhex yloxy)-1,4-phenylene)]. Examples of the materials that emit orange to red light include poly[2-methoxy-5-(2'-ethylhexoxy)-1,4-phenylenevinylene] (abbreviation: MEH-PPV), poly(3-butylthiophene-2,5-diyl) (abbreviation: R$^4$-PAT), poly{[9,9-dihexyl-2,7-bis(1-cyanovinylene)fluorenylene]-alt-co-[2,5-bis(N,N'-diphenyl amino)-1,4-phenylene]}, and poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD).

Note that the light-emitting layer 303 may have a structure in which any of the above light-emitting substances (a guest material) is dispersed in another substance (a host material). As the host material, a variety of kinds of materials can be used, and it is preferable to use a substance which has a lowest unoccupied molecular orbital level (LUMO level) higher than that of the guest material and has a highest occupied molecular orbital level (HOMO level) lower than that of the guest material. With the structure in which the guest material is dispersed in the host material, crystallization of the light-emitting layer 303 can be suppressed. Furthermore, concentration quenching due to high concentration of the guest material can be suppressed.

As the host material, the above-described substance having a high hole-transport property (e.g., an aromatic amine compound or a carbazole derivative) or a later-described substance having a high electron-transport property (e.g., a metal complex having a quinoline skeleton or a benzoquinoline skeleton or a metal complex having an oxazole-based or thiazole-based ligand) can be used, for example. The organic compound of one embodiment of the present invention has a high hole-transport property and can be suitably used as the material. Specific examples of the host material are as follows: metal complexes, such as tris(8-quinolinolato)aluminum(III) (abbreviation: Alq), tris(4-methyl-8-quinolinolato) aluminum(III) (abbreviation: Almq$_3$), bis(10-hydroxybenzo[h]quinolinato)beryllium(H) (abbreviation: BeBq$_2$), bis[2-(2'-hydroxyphenyl)pyridinato]zinic(II) (abbreviation: Znpp$_2$), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: Zn(BOX)$_2$), bis[2-(2-benzothiazolyl)phenolato]zinc(II) (abbreviation: Zn(BTZ)$_2$); heterocyclic compounds, such as 2-(4-biphenylyl)-5-(4-tert-butylphenyl)-1,3,4-oxadiazole (abbreviation: PBD), 1,3- bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), and bathocuproine (abbreviation: BCP); carbazole derivatives, such as CzPA and 3,6-diphenyl-9-[4-(10-phenyl-9-anthryl)phenyl]-9H-carbazole (abbreviation: DPCzPA); aromatic hydrocarbon compounds or condensed aromatic compounds, such as DNA, t-BuDNA, DPAnth, 9,10-bis(3,5-diphenylphenyl)anthracene (abbreviation: DPPA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl) tripyrene (abbreviation: TPB3), and 6,12-dimethoxy-5,11-diphenylchrysene; aromatic amine compounds, such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB, TPD, DFLDPBi, and BSPB.

Alternatively, the followings can be used: compounds having an arylamine skeleton, such as 4-phenyl-4'-(9-phenyl-9H-carbazol-3-yl)triphenylamine (abbreviation: PCBA1BP), PCzPCN1, and 2,3-bis(4-diphenylaminophenyl)quinoxaline (abbreviation: TPAQn); carbazole derivatives, such as CBP and 4,4',4"-tris(N-carbazolyl)triphenylamine (abbreviation: TCTA); and nitrogen-containing heteroaromatic compounds, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), and 2-[4-(3,6-diphenyl-9H-carbazol-9-yl)phenyl] dibenzo[f,h]quinoxaline (abbreviation: 2CzPDBq-III). Further alternatively, a high molecular compound such as PVK can be used.

As the host material, plural kinds of materials can be used. For example, in order to suppress crystallization, a substance such as rubrene which suppresses crystallization, may be further added. In addition, NPB, Alq, or the like may be further added in order to efficiently transfer energy to the guest material.

Further, when a plurality of light-emitting layers are provided and emission colors of the layers are made different, light emission of a desired color can be obtained from the light-emitting element as a whole. For example, the emission colors of first and second light-emitting layers are complementary in a light-emitting element having the two light-emitting layers, so that the light-emitting element can be made to emit white light as a whole. Further, the same applies to a light-emitting element having three or more light-emitting layers.

<Electron-Transport Layer 304>

The electron-transport layer 304 contains a substance with a high electron-transport property.

The substance with a high electron-transport property is preferably an organic compound having a property of transporting more electrons than holes, and is especially preferably a substance with an electron mobility of $10^{-6}$ cm$^2$/V·s or more.

For example, metal complexes such as Alq, Almq$_3$, BeBq$_2$, BAlq, Zn(BOX)$_2$, and Zn(BTZ)$_2$ can be used.

Alternatively, heteroaromatic compounds such as PBD, OXD-7, TAZ, BPhen, BCP, 3-(4-tert-butylphenyl)-4-(4-ethylphenyl)-5-(4-biphenylyl)-1,2,4-triazole (abbreviation: p-EtTAZ), 4,4'-bis(5-methylbenzoxazol-2-yl)stilbene (abbreviation: BzOs) can be used.

Further alternatively, it is possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy).

<Electron-Injection Layer 305>

The electron-injection layer 305 contains a substance with a high electron-injection property.

Examples of the substance with a high electron-injection property include an alkali metal, an alkaline earth metal, a rare earth metal, and a compound thereof (e.g., an oxide thereof, a carbonate thereof, and a halide thereof), such as lithium, cesium, calcium, lithium oxide, lithium carbonate, cesium carbonate, lithium fluoride, cesium fluoride, calcium fluoride, and erbium fluoride.

The electron-injection layer 305 may contain the above-described substance with a high electron-transport property and a donor substance. For example, the electron-injection layer 305 may be formed using an Alq layer containing magnesium (Mg). When the substance with a high electron-transport property and the donor substance are contained, the mass ratio of the donor substance to the substance with a high electron-transport property is from 0.001:1 to 0.1:1.

Examples of the donor substance include an alkali metal, an alkaline earth metal, a rare earth metal, and a compound thereof (an oxide thereof), such as lithium, cesium, magnesium, calcium, erbium, ytterbium, lithium oxide, calcium oxide, barium oxide, and magnesium oxide; a Lewis base; and an organic compound such as tetrathiafulvalene (abbreviation: TTF), tetrathianaphthacene (abbreviation: TTN), nickelocene, or decamethylnickelocene.

<Charge-Generation Region>

The charge-generation region included in the hole-injection layer and the charge-generation region 308 each contain a substance with a high hole-transport property and an acceptor substance (electron acceptor). The acceptor substance is preferably added such that the mass ratio of the acceptor substance to the substance with a high hole-transport property is 0.1:1 to 4.0:1.

The charge-generation region is not limited to a structure in which a substance with a high hole-transport property and an acceptor substance are contained in the same film, and may have a structure in which a layer containing a substance with a high hole-transport property and a layer containing an acceptor substance are stacked. Note that in the case of a stacked-layer structure in which the charge-generation region is provided on the cathode side, the layer containing the substance with a high hole-transport property is in contact with the cathode, and in the case of a stacked-layer structure in which the charge-generation region is provided on the anode side, the layer containing the acceptor substance is in contact with the anode.

The substance with a high hole-transport property is preferably an organic compound having a property of transporting more holes than electrons, and is especially preferably an organic compound with a hole mobility of $10^{-6}$ cm$^2$/V·s or more.

Specifically, it is possible to use any of the materials with a high hole-transport property shown as materials that can be used for the hole-transport layer 302, such as an organic compound of one embodiment of the present invention, aromatic amine compounds such as NPB and BPAFLP, carbazole derivatives such as CBP, CzPA, and PCzPA, aromatic hydrocarbon compounds such as t-BuDNA, DNA, and DPAnth, and high molecular compounds such as PVK and PVTPA.

Examples of the acceptor substance include organic compounds, such as 7,7,8,8-tetracyano-2,3,5,6-tetrafluoroquinodimethane (abbreviation: $F_4$-TCNQ) and chloranil, oxides of transition metals, and oxides of metals that belong to Groups 4 to 8 in the periodic table. Specifically, vanadium oxide, niobium oxide, tantalum oxide, chromium oxide, molybdenum oxide, tungsten oxide, manganese oxide, and rhenium oxide are preferable since their electron-accepting property is high. In particular, use of molybdenum oxide is preferable because of its stability in the air, a low hygroscopic property, and easily handling.

<Electron-Injection Buffer Layer 306>

The electron-injection buffer layer 306 contains a substance with a high electron-injection property. The electron-injection buffer layer 306 facilitates electron injection from the charge-generation region 308 into the EL layer 203. As the material having a high electron-injection property, any of the above-described materials can be used. Alternatively, the electron-injection buffer layer 306 may contain any of the above-described materials with a high electron-transport property and donor substances.

<Electron-Relay Layer 307>

The electron-relay layer 307 immediately accepts electrons drawn out of the acceptor substance in the charge-generation region 308.

The electron-relay layer 307 contains a substance with a high electron-transport property. As the substance with a high electron-transport property, a phthalocyanine-based material or a metal complex having a metal-oxygen bond and an aromatic ligand is preferably used.

As the phthalocyanine-based material, specifically, it is possible to use CuPc, a phthalocyanine tin(II) complex (SnPc), a phthalocyanine zinc complex (ZnPc), cobalt(II) phthalocyanine, β-form (CoPc), phthalocyanine iron (FePc), vanadyl 2,9,16,23-tetraphenoxy-29H,31H-phthalocyanine (PhO-VOPc), or the like.

As the metal complex having a metal-oxygen bond and an aromatic ligand, a metal complex having a metal-oxygen double bond is preferably used. A metal-oxygen double bond has an acceptor property; thus, electrons can transfer (be donated and accepted) more easily.

As the metal complex having a metal-oxygen bond and an aromatic ligand, a phthalocyanine-based material is also preferably used. In particular, vanadyl phthalocyanine (VOPc), a phthalocyanine tin(IV) oxide complex (SnOPc), or a phthalocyanine titanium oxide complex (TiOPc) is preferable because a metal-oxygen double bond is more likely to act on another molecule in term's of a molecular structure and an acceptor property is high.

As the phthalocyanine-based material, a phthalocyanine-based material having a phenoxy group is preferably used. Specifically, a phthalocyanine derivative having a phenoxy group, such as PhO-VOPc, is preferably used. The phthalocyanine derivative having a phenoxy group is soluble in a solvent; thus, the phthalocyanine derivative has an advantage of being easily handled during formation of a light-emitting element and an advantage of facilitating maintenance of an apparatus used for film formation.

Examples of other materials with a high electron-transport property include perylene derivatives such as 3,4,9,10-perylenetetracarboxylic dianhydride (abbreviation: PTCDA), 3,4,9,10-perylenetetracarboxylic bisbenzimidazole (abbreviation: PTCBI), N,N'-dioctyl-3,4,9,10-perylenetetracarboxylic diimide (abbreviation: PTCDI-C8H), N,N'-dihexyl-3,4,9,10-perylenetetracarboxylic diimide (abbreviation: Hex PTC), and the like. Alternatively, it is possible to use a nitrogen-containing condensed aromatic compound such as pirazino[2,3-f][1,10]phenanthroline-2,3-dicarbonitrile (abbreviation: PPDN), 2,3,6,7,10,11-hexacyano-1,4,5,8,9,12-hexaazatriphenylene (abbreviation: HAT (CN)$_6$), 2,3-diphenylpyrido[2,3-b]pyrazine (abbreviation: 2PYPR), or 2,3-bis(4-fluorophenyl)pyrido[2,3-b]pyrazine (abbreviation: F2PYPR). The nitrogen-containing condensed aromatic compound is preferably used for the electron-relay layer 307 because of its stability.

Further alternatively, it is possible to use 7,7,8,8-tetracyanoquinodimethane (abbreviation: TCNQ), 1,4,5,8-naphthalenetetracarboxylicdianhydride (abbreviation: NTCDA), perfluoropentacene, copper hexadecafluoro phthalocyanine (abbreviation: $F_{16}$CuPc), N,N'-bis(2,2,3,3,4,4,5,5,6,6,7,7,8,8,8-pentadecafluorooctyl)-1,4,5,8-naphthalenetetracarboxylic diimide (abbreviation: NTCD1-C8F), 3',4'-dibutyl-5,5''-bis(dicyanomethylene)-5,5''-dihydro-2,2':5',2''-terthiophene (abbreviation: DCMT), or a methanofullerene (e.g., [6,6]-phenyl $C_{61}$ butyric acid methyl ester).

The electron-relay layer 307 may further contain any of the above-described donor substances. When the donor substance is contained in the electron-relay layer 307, electrons can transfer easily and the light-emitting element can be driven at a lower voltage.

The LUMO levels of the substance with a high electron-transport property and the donor substance are preferably −5.0 eV to −3.0 eV, i.e., between the LUMO level of the acceptor substance contained in the charge-generation region 308 and the LUMO level of the substance with a high electron-transport property contained in the electron-transport layer 304 (or the LUMO level of the EL layer 203 in contact with the electron-relay layer 307 through the electron-injection buffer layer 306). When a donor substance is contained in the electron-relay layer 307, as the substance with a high electron-transport property, a substance with a LUMO level higher than the acceptor level of the acceptor substance contained in the charge-generation region 308 can be used.

The above-described layers included in the EL layer 203 and the intermediate layer 207 can be formed separately by any of the following methods: an evaporation method (including a vacuum evaporation method), a transfer method, a printing method, an inkjet method, a coating method, and the like.

By use of a light-emitting element described in this embodiment, a passive matrix light-emitting device or an active matrix light-emitting device in which driving of the light-emitting element is controlled by a transistor can be manufactured.

Furthermore, the light-emitting device can be applied to an electronic device, a lighting device, and the like.

This embodiment can be freely combined with any of the other embodiments.

Embodiment 3

In this embodiment, a light-emitting element of one embodiment of the present invention will be described with reference to FIG. 2.

A light-emitting element illustrated in FIG. 2 includes the EL layer 203 between the first electrode 201 and the second electrode 205. The EL layer 203 includes at least a light-emitting layer 213 that contains a first organic compound 221, a second organic compound 222, and a phosphorescent compound 223. In addition to the light-emitting layer 213, the EL layer 203 may further include one or more layers containing any of a substance with a high hole-injection property, a substance with a high hole-transport property, a hole-blocking material, a substance with a high electron-transport property, a substance with a high electron-injection property, a substance with a bipolar property (a substance with a high electron-transport property and a high hole-transport property), and the like.

The phosphorescent compound 223 is a guest material in the light-emitting layer 213. In this embodiment, one of the first organic compound 221 and the second organic compound 222, the content of which in the light-emitting layer 213 is higher than that of the other, is a host material in the light-emitting layer 213. The organic compound of one embodiment of the present invention can be suitably used as the first organic compound 221 or the second organic compound 222.

When the light-emitting layer 213 has the structure in which the guest material is dispersed in the host material, the crystallization of the light-emitting layer can be suppressed. Further, it is possible to suppress concentration quenching due to high concentration of the guest material; thus, the light-emitting element can have higher emission efficiency.

Note that it is preferable that a triplet excited energy level ($T_1$ level) of each of the first organic compound 221 and the second organic compound 222 be higher than that of the phosphorescent compound 223. This is because, when the $T_1$ level of the first organic compound 221 (or the second organic compound 222) is lower than that of the phosphorescent compound 223, the triplet excited energy of the phosphorescent compound 223, which is to contribute to light emission, is quenched by the first organic compound 221 (or the second organic compound 222) and accordingly, the emission efficiency decreases.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) largely overlap with an absorption spectrum of a guest material (specifically, spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, because the phosphorescence spectrum of the host material is located on the longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For this reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in one embodiment of the present invention, a combination of the first organic compound 221 and the second organic compound 222 preferably forms an excited complex (also referred to as exciplex). In that case, the first organic compound 221 and the second organic compound 222 form an exciplex at the time of recombination of carriers (electrons and holes) in the light-emitting layer 213. Thus, in the light-emitting layer 213, a fluorescence spectrum of the first organic compound 221 and that of the second organic compound 222 are converted into an emission spectrum of the exciplex which is located on a longer wavelength side. Moreover, when the first organic compound and the second organic compound are selected such that the emission spectrum of the exciplex largely overlaps with the absorption spectrum of the guest material, energy transfer from a singlet excited state can be maximized. Note that also in the case of a triplet excited state, energy transfer from the exciplex, not the host material, is considered to occur.

As the phosphorescent compound 223, for example, the phosphorescent compound described in Embodiment 2 can be used. Although any combination of the first organic compound 221 and the second organic compound 222 can be used as long as an exciplex is formed, a compound which is likely to accept electrons (a compound having an electron-trapping property) and a compound which is likely to accept holes (a compound having a hole-trapping property) are preferably combined.

As the compound which is likely to accept electrons, a π-electron deficient heteroaromatic compound such as a nitrogen-containing heteroaromatic compound, a metal complex having a quinoline skeleton or a benzoquinoline skeleton, or a metal complex having an oxazole-based ligand or a thiazole-based ligand can be used, for example.

Specific examples are as follows: metal complexes such as $BeBq_2$, BAlq, Znq, $Zn(BOX)_2$, and $Zn(BTZ)_2$; heterocyclic compounds having a polyazole skeleton, such as PBD, TAZ, OXD-7, 9-[4-(5-phenyl-1,3,4-oxadiazol-2-yl)phenyl]-9H-carbazole (abbreviation: CO11), 2,2',2"-(1,3,5-Benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a quinoxaline skeleton or a dibenzoquinoxaline skeleton, such as 2mDBTPDBq-II, 2mDBTBPDBq-II, 2CzPDBq-III, 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and 2-[3'-(9H-carbazol-9-yl)biphenyl-3-yl]dibenzo[f,h]quinoxaline (abbreviation: 2mCzBPDBq); heterocyclic compounds having a diazine skeleton (a pyrimidine skeleton or a pyrazine skeleton), such as 4,6-bis[3-(phenanthren-9-yl)phenyl]pyrimidine (abbreviation: 4,6mPnP2Pm), 4,6-bis[3-(9H-carbazol-9-yl)phenyl]pyrimidine (abbreviation: 4,6mCzP2Pm), and 4,6-bis[3-(4-dibenzothienyl)phenyl]pyrimidine (abbreviation: 4,6mDBTP2Pm-II); and heterocyclic compounds having a pyridine skeleton, such as 3,5-bis[3-(9H-carbazol-9-yl)phenyl]pyridine, 1,3,5-tri[3-(3-pyridyl)phenyl]benzene (abbreviation: TmPyPB), and 3,3',5,5'-tetra[(m-pyridyl)-phen-3-yl]biphenyl (abbreviation: BP4mPy). Among the above substances, the heterocyclic compounds having a quinoxaline skeleton or a dibenzoquinoxaline skeleton, the heterocyclic compounds having a diazine skeleton, and the heterocyclic compounds having a pyridine skeleton have high reliability and are thus preferable.

As the compound which is likely to accept holes, the organic compound of one embodiment of the present invention can be suitably used. Alternatively, a π-electron rich heteroaromatic compound (e.g., a carbazole derivative or an indole derivative) or an aromatic amine compound can be suitably used, examples of which include PCBA1BP, 4,4'-di (1-naphthyl)-4''-(9-phenyl-9H-carbazol-3-yl)triphenylamine (abbreviation: PCBNBB), PCzPCN1, 4,4',4''-tris[N-(1-naphthyl)-N-phenylamino]triphenylamine (abbreviation: 1'-TNATA), [N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N', N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), TPD, DPAB, N-(9,9-dimethyl-9H-fluoren-2-yl)-N-{9,9-dimethyl-2-[N'-phenyl-N'-(9,9-dimethyl-9H-fluoren-2-yl)amino]-9H-1-fluoren-7-yl}phenylamine (abbreviation: DFLADFL), PCzPCA1,3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyl)amino]-9-phenylcarbazole (abbreviation: PCzTPN2), and PCzPCA2.

The materials that can be used for the first organic compound 221 and the second organic compound 222 are not limited to the above compounds as long as the combination of the first organic compound 221 and the second organic compound 222 can form an exciplex, the emission spectrum of the exciplex overlaps with the absorption spectrum of the phosphorescent compound 223, and the peak of the emission spectrum of the exciplex has a longer wavelength than the peak of the absorption spectrum of the phosphorescent compound 223.

Note that in the case where a compound which is likely to accept electrons and a compound which is likely to accept holes are used for the first organic compound 221 and the second organic compound 222, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, the light-emitting element can achieve high external quantum efficiency.

Note that in one embodiment of the present invention, the light-emitting layer 213 can be formed using a host molecule having a hole-trapping property and a host molecule having an electron-trapping property as the two kinds of organic compounds other than the phosphorescent compound 223 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

This embodiment can be freely combined with any of the other embodiments.

Embodiment 4

Figure 3A:
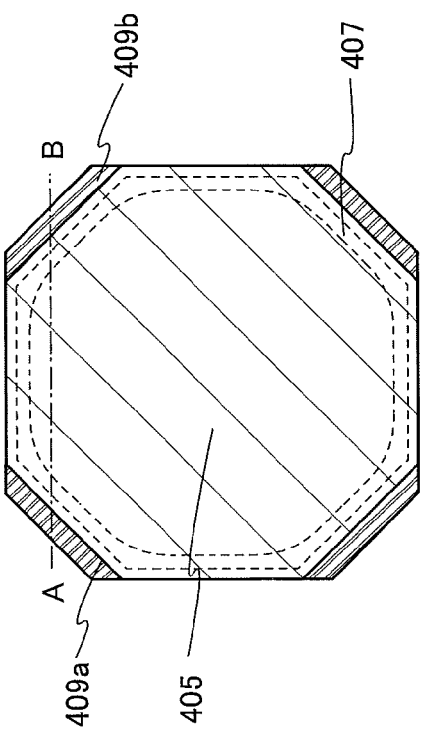
FIGS. 3A and 3B illustrate an example of a light-emitting device of one embodiment of the present invention.
Figure 3B:
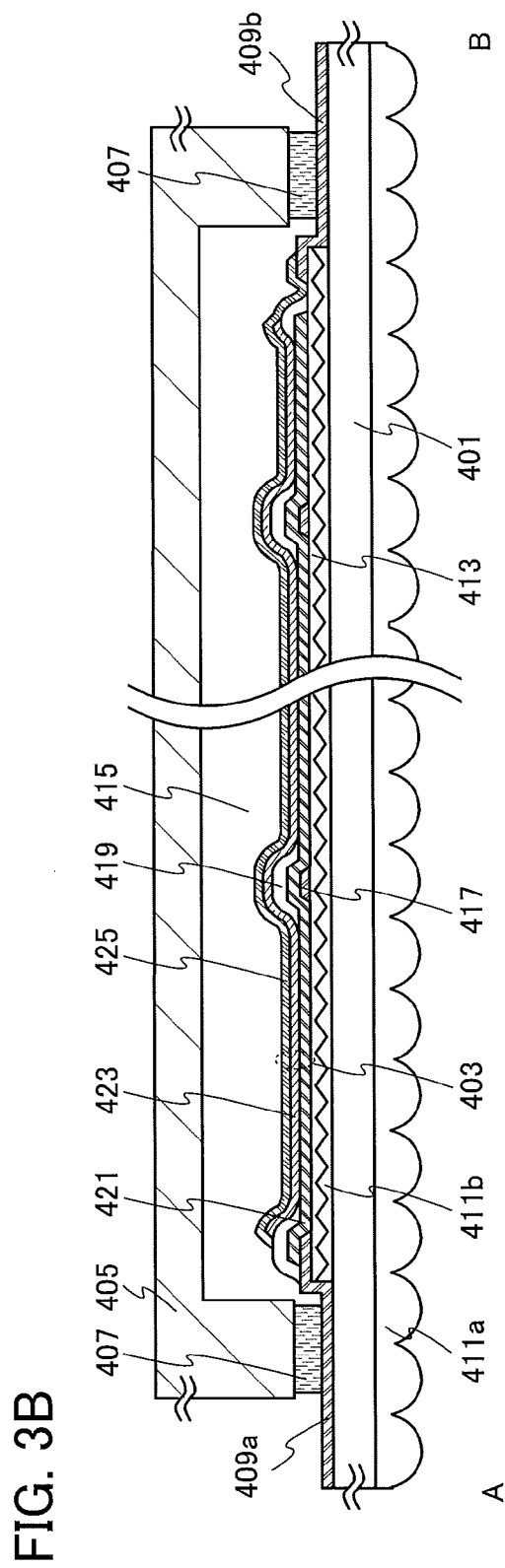

In this embodiment, a light-emitting device of one embodiment of the present invention will be described with reference to FIGS. 3A and 3B. FIG. 3A is a plan view of a light-emitting device of one embodiment of the present invention and FIG. 3B is a cross-sectional view taken along a dashed-dotted line A-B in FIG. 3A.

In the light-emitting device of this embodiment, a light-emitting element 403 (a first electrode 421, an EL layer 423, and a second electrode 425) is provided in a space 415 surrounded by a support substrate 401, a sealing substrate 405, and a sealant 407. The light-emitting element 403 has a bottom emission structure. Specifically, the light-emitting element 403 includes the first electrode 421 that transmits visible light over the support substrate 401, the EL layer 423 over the first electrode 421, and the second electrode 425 that reflects visible light over the EL layer 423.

One embodiment of the present invention is applied to the light-emitting element 403. Specifically, a light-emitting layer included in the EL layer 423 contains the organic compound of one embodiment of the present invention. Thus, the light-emitting element 403 has a long lifetime. By application of one embodiment of the present invention, a highly reliable light-emitting device can be achieved.

A first ten final 409a is electrically connected to an auxiliary wiring 417 and the first electrode 421. An insulating layer 419 is provided in a region which overlaps with the auxiliary wiring 417 over the first electrode 421. The first terminal 409a and the second electrode 425 are electrically insulated by the insulating layer 419. The second terminal 409b is electrically connected to the second electrode 425. Note that although the first electrode 421 is formed over the auxiliary wiring 417 in this embodiment, the auxiliary wiring 417 may be formed over the first electrode 421.

The organic EL element emits light in a region with a refractive index higher than that of the air; thus, when light is extracted to the atmosphere, total reflection occurs in the organic EL element or at the interface between the organic EL element and the atmosphere under a certain condition, which results in a light extraction efficiency of lower than 100%.

Accordingly, for example, a light extraction structure 411a is preferably provided at an interface between the support substrate 401 and the atmosphere. The refractive index of the support substrate 401 is higher than that of the atmosphere. Therefore when provided at the interface between the support substrate 401 and the atmosphere, the light extraction structure 411a can reduce light which cannot be extracted to the atmosphere due to total reflection, resulting in an increase in the light extraction efficiency of the light-emitting device.

A light extraction structure 411b is preferably provided at an interface between the light-emitting element 403 and the support substrate 401.

However, when the first electrode 421 has unevenness, leakage current might occur in the EL layer 423 formed over the first electrode 421. Therefore, in this embodiment, a planarization layer 413 having a refractive index higher than or equal to that of the EL layer 423 is provided in contact with the light extraction structure 411b. Thus, the first electrode 421 can be a flat film, and occurrence of leakage current in the EL layer 423 due to the unevenness of the first electrode 421 can be suppressed. Moreover, since the light extraction structure 411b is provided at an interface between the planarization layer 413 and the support substrate 401, light which cannot be extracted to the atmosphere due to total reflection can be reduced, so that the light extraction efficiency of the light-emitting device can be improved.

Note that in FIG. 3B, the support substrate 401, the light extraction structure 411a, and the light extraction structure 411b are different components, but one embodiment of the present invention is not limited to this structure. Two or all of these may be formed as one component. Furthermore, in the case where unevenness of the first electrode 421 is not formed (for example, in the case where the light extraction structure 411b does not have unevenness) when the light extraction structure 411b is provided, the planarization layer 413 is not necessarily provided.

Although the shape of the light-emitting device illustrated in FIG. 3A is octagonal, one embodiment of the present invention is not limited thereto. The shape of the light-emitting device may be another polygonal shape or a shape having a curved portion. As the shape of the light-emitting device, a triangle, a quadrilateral, a hexagon, or the like is especially preferred. This is because a plurality of light-emitting devices having such a shape can be provided in a limited area without a gap. In addition, such light-emitting devices can be formed effectively utilizing a limited substrate area. Furthermore, the number of light-emitting elements included in the light-emitting device is not limited to one and may be more than one.

The shapes of the unevenness of the light extraction structure 411a and the light extraction structure 411b do not necessarily have regularity. When the shape of the unevenness has regularity, the unevenness functions as a diffraction grating depending on the size of the unevenness, so that an interference effect is increased and light with a certain wavelength is easily extracted to the atmosphere in some cases. Therefore, it is preferable that the shape of the unevenness do not have regularity.

There is no particular limitation on the base shape of the unevenness; for example, the shape may be a polygon such a triangle or a quadrangle, a circle, or the like. When the base shape of the unevenness has order of regularity, the unevenness is preferably provided such that gaps are not formed between adjacent portions of the unevenness. A regular hexagon is given as an example of a preferable base shape.

There is no particular limitation on the shape of the unevenness; for example, a hemisphere or a shape with a vertex such as a circular cone, a pyramid (e.g., a triangular pyramid or a square pyramid), or an umbrella shape can be used.

In particular, the size or height of the unevenness is preferably greater than or equal to 1 in which case the influence of interference of light can be reduced.

The light extraction structure 411a and the light extraction structure 411b can be formed directly on the support substrate 401. For example, any of the following methods can be used as appropriate: an etching method, a sand blasting method, a microblast processing method, a frost processing method, a droplet discharge method, a printing method (screen printing or offset printing by which a pattern is formed), a coating method such as a spin coating method, a dipping method, a dispenser method, an imprint method, and a nanoimprint method.

As a material of the light extraction structure 411a and the light extraction structure 411b, a resin can be used, for example. As the light extraction structure 411a and the light extraction structure 411b, a hemispherical lens, a micro lens array, a film provided with an uneven structure, a light diffusing film, or the like can be used. For example, the above lens or film is attached onto the support substrate 401 with the use of an adhesive whose refractive index is substantially equal to that of the support substrate 401 or the above lens or film, so that the light extraction structure 411a and the light extraction structure 411b can be formed.

The planarization layer 413 is more flat in its one surface that is in contact with the first electrode 421 than in its other surface that is in contact with the light extraction structure 411b. Accordingly, the first electrode 421 can be a flat film. As a result, generation of leakage current in the EL layer 423 due to unevenness of the first electrode 421 can be suppressed. As a material of the planarization layer 413, a glass, a liquid, a resin, or the like having a high refractive index can be used. The planarization layer 413 has a light-transmitting property.

This embodiment can be combined with any of the other embodiments as appropriate.

Embodiment 5

Figure 4A:
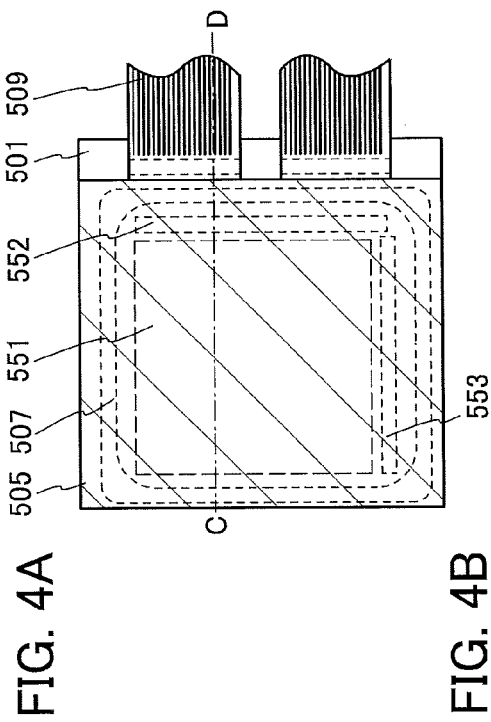
FIGS. 4A and 4B illustrate an example of a light-emitting device of one embodiment of the present invention.

In this embodiment, a light-emitting device of one embodiment of the present invention will be described with reference to FIGS. 4A and 4B. FIG. 4A is a plan view of the light-emitting device of one embodiment of the present invention and FIG. 4B is a cross-sectional view taken along a dashed-dotted line C-D in FIG. 4A.

An active matrix light-emitting device according to this embodiment includes, over a support substrate 501, a light-emitting portion 551, a driver circuit portion 552 (gate side driver circuit portion), a driver circuit portion 553 (source side drive circuit portion), and the sealant 507. The light-emitting portion 551, the driver circuit portions 552 and 553 are formed in a space 515 formed by the support substrate 501, a sealing substrate 505, and the sealant 507.

Figure 4B:
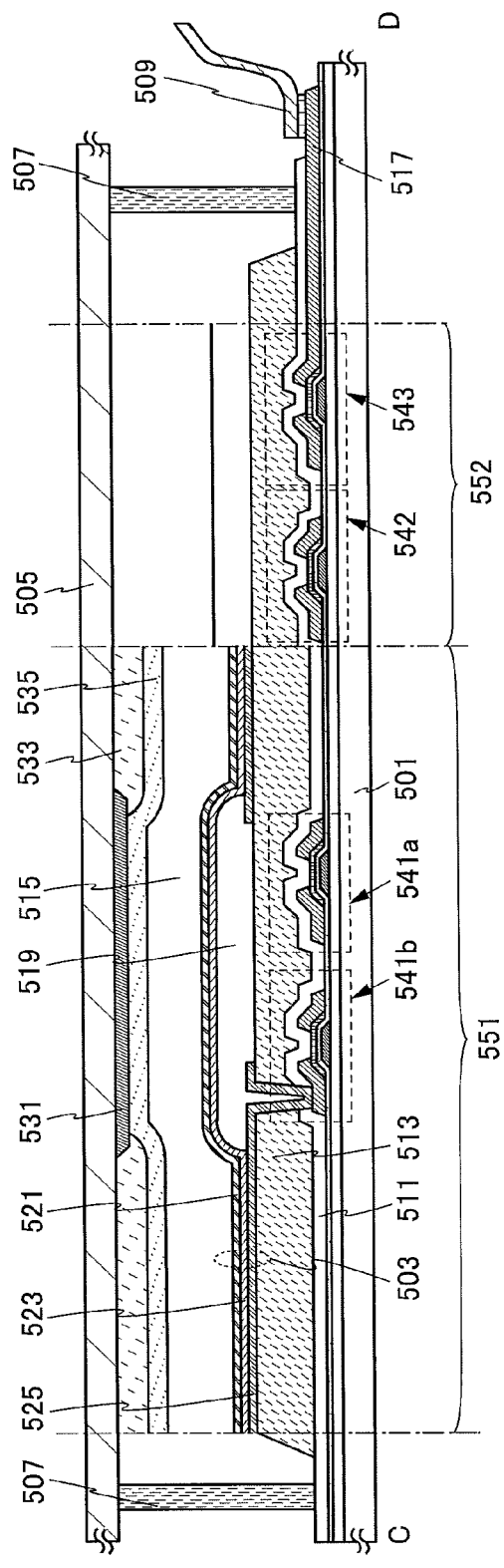

The light-emitting portion 551 illustrated in FIG. 4B includes a plurality of light-emitting units each including a switching transistor 541a, a current control transistor 541b, and the second electrode 525 electrically connected to a wiring (a source electrode or a drain electrode) of the transistor 541b.

A light-emitting element 503 has a top emission structure, and includes a first electrode 521 that transmits visible light, an EL layer 523, and the second electrode 525 that reflects visible light. Further, a partition wall 519 is formed to cover an end portion of the second electrode 525.

One embodiment of the present invention is applied to the light-emitting element 503. Specifically, a light-emitting layer included in the EL layer 523 contains the organic compound of one embodiment of the present invention. Thus, the light-emitting element 503 has a long lifetime. By application of one embodiment of the present invention, a highly reliable light-emitting device can be achieved.

Over the support substrate 501, a lead wiring 517 for connecting an external input terminal through which a signal (e.g., a video signal, a clock signal, a start signal, or a reset signal) or a potential from the outside is transmitted to the driver circuit portions 552 and 553 is provided. Here, an example in which a flexible printed circuit (FPC) 509 is provided as the external input terminal is described. Note that a printed wiring board (PWB) may be attached to the FPC 509. In this specification, the light-emitting device includes in its category the light-emitting device itself and the light-emitting device on which the FPC or the PWB is mounted.

The driver circuit portions 552 and 553 have a plurality of transistors. FIG. 4B illustrates an example in which the driver circuit portion 552 has a CMOS circuit which is a combination of an n-channel transistor 542 and a p-channel transistor 543. A circuit included in the driver circuit portion can be formed with various types of circuits such as a CMOS circuit, a PMOS circuit, or an NMOS circuit. The present invention is not limited to a driver-integrated type described in this embodiment in which the driver circuit is formed over the substrate over which the light-emitting portion is formed. The driver circuit can be formed over a substrate that is different from the substrate over which the light-emitting portion is formed.

To prevent an increase in the number of manufacturing steps, the lead wiring 517 is preferably formed using the same material and the same step(s) as those of the electrode or the wiring in the light-emitting portion or the driver circuit portion.

Described in this embodiment is an example in which the lead wiring 517 is formed using the same material and the same step(s) as those of the source electrode and the drain electrode of the transistor included in the light-emitting portion 551 and the driver circuit portion 552.

In FIG. 4B, the sealant 507 is in contact with a first insulating layer 511 over the lead wiring 517. The adhesion of the sealant 507 to metal is low in some cases. Therefore, the sealant 507 is preferably in contact with an inorganic insulating film over the lead wiring 517; such a structure enables a light-emitting device with high sealing property, high adhesion property, and high reliability to be achieved. As examples of the inorganic insulating film, an oxide film of a metal or a semiconductor, a nitride film of a metal or a semiconductor, and an oxynitride film of a metal or a semiconductor are given; specifically, a silicon oxide film, a silicon nitride film, a silicon oxynitride film, a silicon nitride oxide film, an aluminum oxide film, a titanium oxide film, and the like can be given.

The first insulating layer 511 has an effect of preventing diffusion of impurities into a semiconductor included in the transistor. As the second insulating layer 513, an insulating film with a planarization function is preferably selected in order to reduce surface unevenness due to the transistor.

There is no particular limitation on the structure of the transistor used in the light-emitting device of one embodiment of the present invention. A top-gate transistor may be used, or a bottom-gate transistor such as an inverted staggered transistor may be used. The transistor may be a channel-etched transistor or a channel protective transistor. In addition, there is no particular limitation on a material used for the transistor.

A semiconductor layer can be formed using silicon or an oxide semiconductor. As a silicon semiconductor, single crystal silicon, polycrystalline silicon, or the like can be used as appropriate. As an oxide semiconductor, an In—Ga—Zn-based metal oxide or the like can be used as appropriate. Note that the semiconductor layer is preferably formed using an oxide semiconductor which is an In—Ga—Zn-based metal oxide so that a transistor with low off-state current is achieved, in which case an off-state leakage current of the light-emitting element can be reduced.

A color filter 533 that is a coloring layer is provided on the sealing substrate 505 so as to overlap with the light-emitting element 503 (its light-emitting region). The color filter 533 is provided to control the color of light emitted from the light-emitting element 503. For example, in a full-color display device using white light-emitting elements, a plurality of light-emitting units provided with color filters of different colors are used. In that case, three colors, red (R), green (G), and blue (B), may be used, or four colors, red (R), green (G), blue (B), and yellow (Y), may be used.

A black matrix 531 is provided between the adjacent color filters 533 (in a position overlapping with the partition wall 519). The black matrix 531 shields a light-emitting unit from light emitted from the light-emitting elements 503 in adjacent light-emitting units and prevents color mixture between the adjacent light-emitting units. Here, the color filter 533 is provided so that its end portions overlap with the black matrix 531, whereby light leakage can be reduced. The black matrix 531 can be formed using a material that blocks light emitted from the light-emitting element 503; for example, a metal or a resin can be used. Note that the black matrix 531 may be provided in a region other than the light-emitting portion 551, for example, in the driver circuit portion 552.

An overcoat layer 535 is formed to cover the color filter 533 and the black matrix 531. The overcoat layer 535 is formed using a material that transmits light emitted from the light-emitting element 503; for example, an inorganic insulating film or an organic insulating film can be used. The overcoat layer 535 is not necessarily provided unless needed.

A structure of the present invention is not limited to the light-emitting device using a color filter method, which is described as an example in this embodiment. For example, a separate coloring method or a color conversion method may be used.

This embodiment can be combined with any of the other embodiments as appropriate.

Embodiment 6

In this embodiment, examples of electronic devices and lighting devices using a light-emitting device to which one embodiment of the present invention is applied will be described with reference to FIGS. 5A to 5E and FIGS. 6A and 6B.

A light-emitting element containing the organic compound of one embodiment of the present invention is applied to a light-emitting device used for electronic devices and lighting devices of this embodiment; thus, the electronic devices and lighting devices have high reliability.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, a large-sized game machine such as a pachinko machine, and the like. Specific examples of these electronic devices and a lighting device are illustrated in FIGS. 5A to 5E and FIGS. 6A and 6B.

Figure 5A:
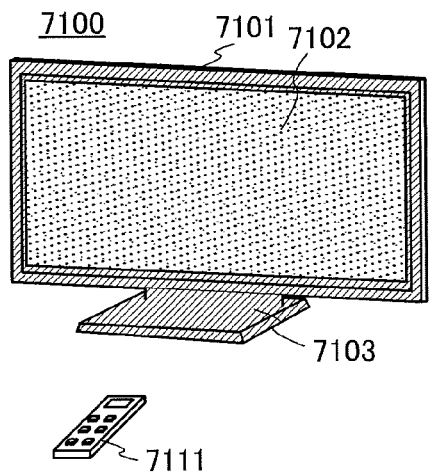
FIGS. 5A to 5E each illustrate an electronic device of one embodiment of the present invention.

FIG. 5A illustrates an example of a television device. In a television device 7100, a display portion 7102 is incorporated in a housing 7101. The display portion 7102 is capable of displaying images. The light-emitting device to which one embodiment of the present invention is applied can be used for the display portion 7102. In addition, here, the housing 7101 is supported by a stand 7103.

Operation of the television device 7100 can be performed with an operation switch of the housing 7101 or a separate remote controller 7111. With operation keys of the remote controller 7111, channels and volume can be controlled and images displayed on the display portion 7102 can be controlled. Furthermore, the remote controller 7111 may be provided with a display portion for displaying data output from the remote controller 7111.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
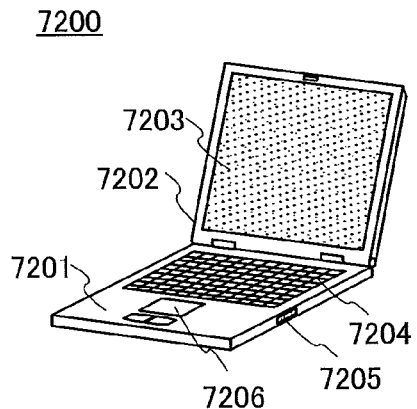

FIG. 5B illustrates an example of a computer. A computer 7200 includes a main body 7201, a housing 7202, a display portion 7203, a keyboard 7204, an external connection port 7205, a pointing device 7206, and the like. Note that this computer is manufactured by using the light-emitting device of one embodiment of the present invention for the display portion 7203.

Figure 5C:
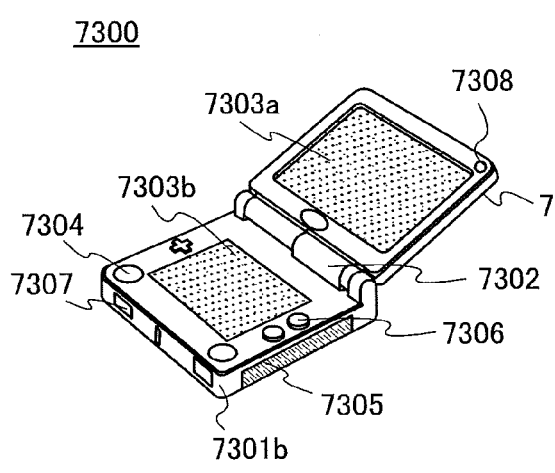

FIG. 5C illustrates an example of a portable game machine. A portable game machine 7300 includes two housings, a housing 7301*a* and a housing 7301*b*, which are connected with a joint portion 7302 so that the portable game machine can be opened or folded. A display portion 7303*a* is incorporated in the housing 7301*a* and a display portion 7303*b* is incorporated in the housing 7301*b*. In addition, the portable game machine illustrated in FIG. 5C includes a speaker portion 7304, a recording medium insertion portion 7305, operation keys 7306, a connection terminal 7307, a sensor 7308 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, vibration, smell, or infrared ray), an LED lamp, a microphone, and the like. The structure of the portable game machine is not limited to the above as long as the light-emitting device according to one embodiment of the present invention is used for at least either the display portion 7303*a* or the display portion 7303*b*, or both of them. The portable game machine may be provided with other accessories as appropriate. The portable game machine illustrated in FIG. 5C has a function of reading a program or data stored in a recording medium to display it on the display portion, and a function of sharing data with another portable game machine by wireless communication. Note that a function of the portable game machine illustrated in FIG. 5C is not limited to the above, and the portable game machine can have a variety of functions.

Figure 5D:
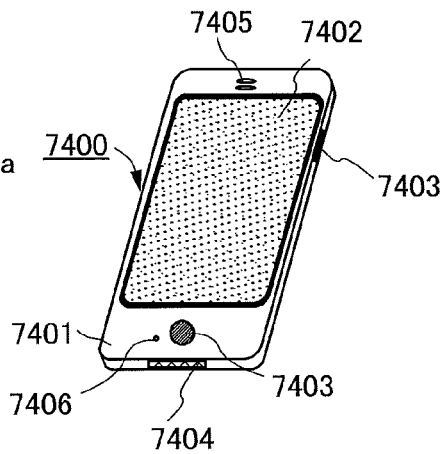

FIG. 5D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using the light-emitting device of one embodiment of the present invention for the display portion 7402. A highly reliable mobile phone can be obtained by using the light-emitting device of one embodiment of the present invention for the display portion 7402.

When the display portion 7402 of the mobile phone 7400 illustrated in FIG. 5D is touched with a finger or the like, data can be input into the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be inputted.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

Figure 5E:
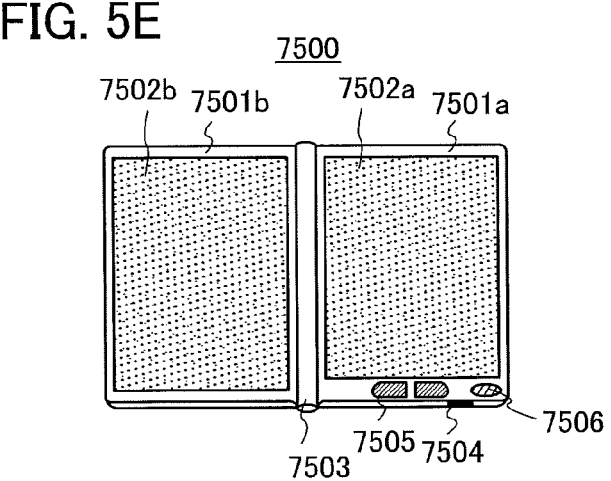

FIG. 5E illustrates an example of a fordable tablet terminal (in an open state). A tablet terminal 7500 includes a housing 7501*a*, a housing 7501*b*, a display portion 7502*a*, and a display portion 7502*b*. The housing 7501*a* and the housing 7501*b* are connected by a hinge 7503 and can be opened and closed along the hinge 7503. The housing 7501*a* includes a power switch 7504, operation keys 7505, a speaker 7506, and the like. Note that the tablet terminal 7500 is manufactured using the light-emitting device of one embodiment of the present invention for either the display portion 7502*a* or the display portion 7502*b* or both.

Part of the display portion 7502*a* or the display portion 7502*b* can be used as a touch panel region, and data can be input by touching displayed operation keys. For example, the entire area of the display portion 7502*a* can display keyboard buttons and serve as a touch panel while the display portion 7502*b* can be used as a display screen.

Figure 6A:
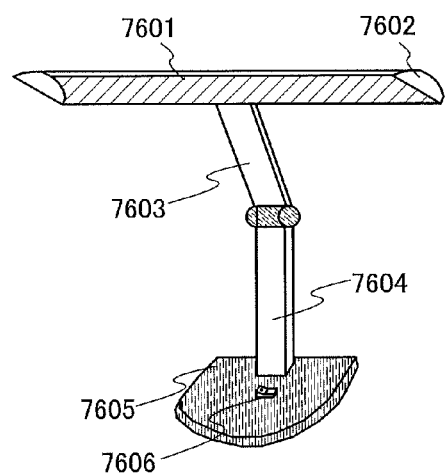
FIGS. 6A and 6B illustrate examples of lighting devices of one embodiment of the present invention.

FIG. 6A illustrates a desk lamp including a lighting portion 7601, a shade 7602, an adjustable atm 7603, a support 7604, a base 7605, and a power switch 7606. The desk lamp is manufactured using the light-emitting device of one embodiment of the present invention for the lighting portion 7601. Note that a lamp includes a ceiling light, a wall light, and the like in its category.

Figure 6B:
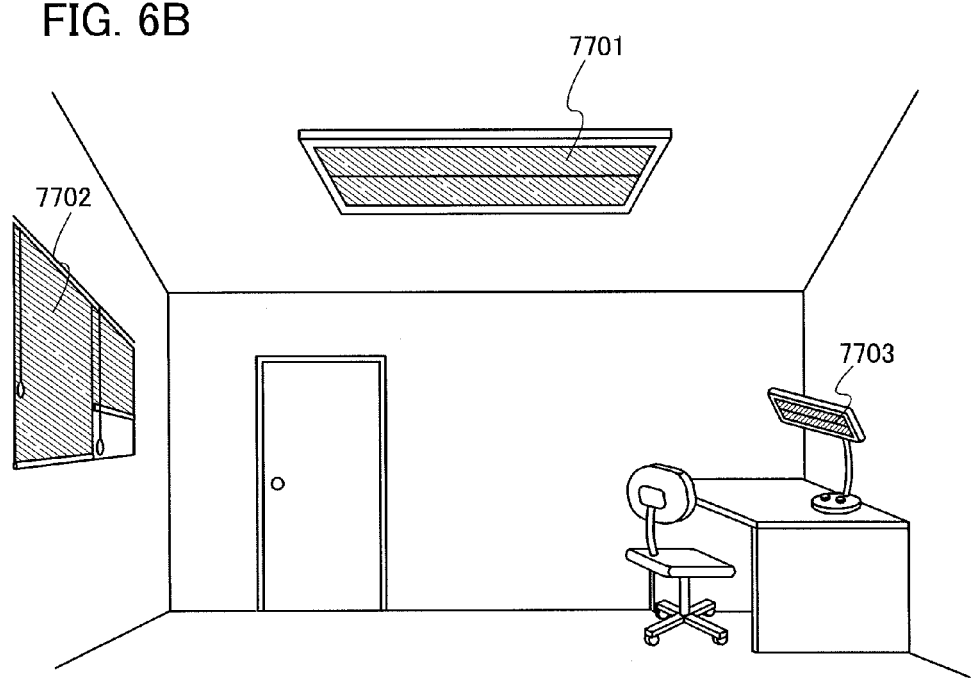

FIG. 6B illustrates an example in which the light-emitting device of one embodiment of the present invention is used for an indoor lighting device 7701. Since the light-emitting device of one embodiment of the present invention can have a larger area, it can be used as a large-area lighting device. In addition, the light-emitting device can be used as a roll-type lighting device 7702. As illustrated in FIG. 6B, a desk lamp 7703 described with reference to FIG. 6A may be used in a room provided with the indoor lighting device 7701.

EXAMPLE 1

Synthesis Example 1

In this example, a description will be made of a method of synthesizing 9,9-dimethyl-N-[4-(1-naphthyl)phenyl]-N-[4-

(9-phenyl-9H-carbazol-3-yl)phenyl]-9H-fluoren-2-amine (abbreviation: PCBNBF) represented by Structural Formula (100) shown below.

[Chemical formula 28]

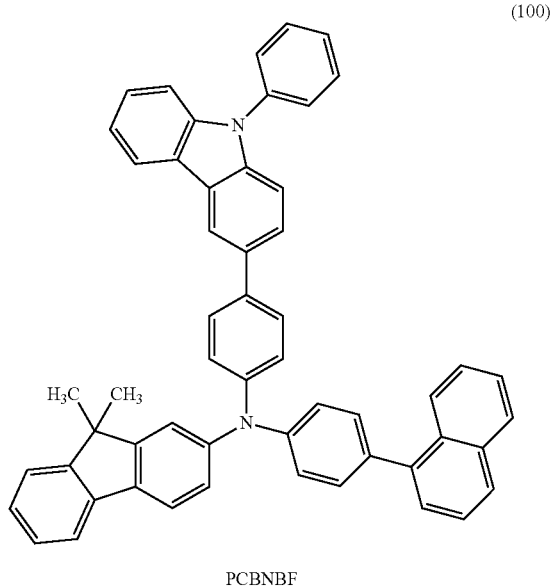

PCBNBF (100)

In this example, two methods of synthesizing PCBNBF will be described.

Synthesis Method 1

Step 1-1: Synthesis of 1-(4-bromophenyl)naphthalene

Synthesis Scheme (a-1) of Step 1-1 is shown.

[Chemical formula 29]

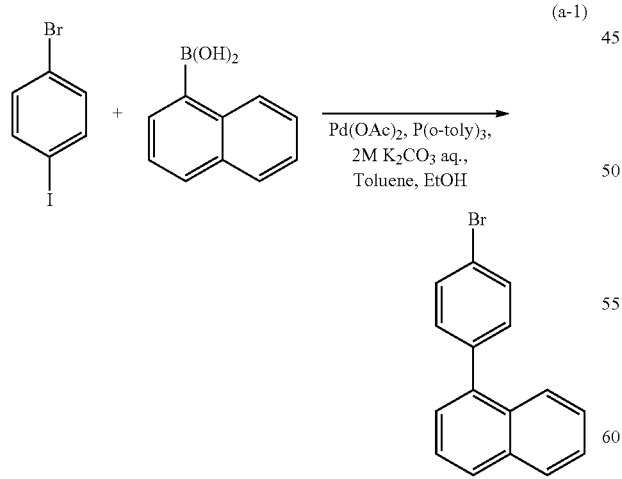

(a-1)

Into a 3-L three-neck flask were put 47 g (0.28 mol) of 1-naphthaleneboronic acid and 82 g (0.29 mol) of 4-bromoiodobenzene, and 750 mL of toluene and 250 mL of ethanol were added thereto. While the pressure was reduced, this mixture was degassed by being stirred. After the degassing, the atmosphere in the flask was replaced with nitrogen. To the solution was added 415 mL (2.0 mol/L) of a potassium carbonate solution. The obtained mixture was degassed by being stirred while the pressure was reduced, and then, the atmosphere in the flask was replaced with nitrogen. Into this were added 4.2 g (14 mmol) of tris(2-methylphenyl)phosphine and 0.7 g (2.8 mmol) of palladium(II) acetate. This mixture was stirred under a nitrogen stream at 90° C. for an hour.

After the stirring, this mixture was allowed to cool to room temperature, and an aqueous layer of this mixture was extracted three times with toluene. The extracted solution and an organic layer were combined and washed twice with water and washed twice with saturated saline. Into this mixture was added magnesium sulfate, and the mixture was dried for 18 hours. The obtained mixture was subjected to natural filtration to remove magnesium sulfate, and the filtrate was concentrated to obtain an orange liquid.

To this orange liquid was added 500 mL of hexane, and the obtained solution was filtrated through Celite (produced by Wako Pure Chemical Industries, Ltd., Catalog No. 531-16855, the same applies to Celite described below and a repetitive description thereof is omitted) and Florisil (produced by Wako Pure Chemical Industries, Ltd., Catalog No. 540-00135, the same applies to Florisil described below and a repetitive description thereof is omitted). The obtained filtrate was concentrated to give a colorless liquid. Into the colorless liquid was added hexane, the obtained mixture was kept at −10° C., and a precipitated impurity was separated by filtration. The obtained filtrate was concentrated to give a colorless liquid. This colorless liquid was purified by distillation under reduced pressure to give a yellow liquid, and the yellow liquid was purified by silica gel column chromatography (developing solvent: hexane), whereby 56 g of an objective colorless liquid was obtained in a yield of 72%.

Step 1-2: Synthesis of 9,9-dimethyl-N-(4-naphthyl)phenyl-N-phenyl-9H-fluoren-2-amine Synthesis Scheme (a-2) of Step 1-2 is shown.

[Chemical formula 30]

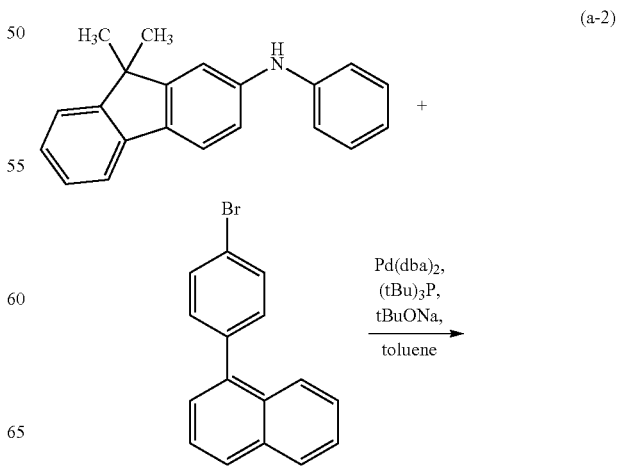

(a-2)

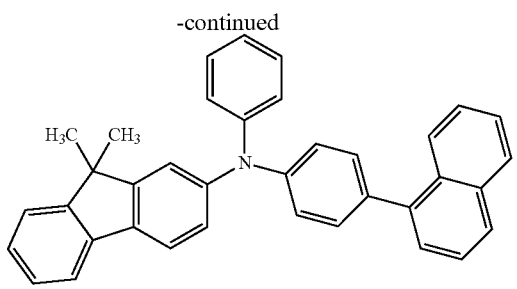

Into a 1-L three-neck flask were put 40 g (0.14 mol) of 9,9-dimethyl-N-phenyl-9H-fluoren-2-amine, 40 g (0.42 mol) of sodium tert-butoxide, and 2.8 g (1.4 mmol) of bis(dibenzylideneacetone)palladium(0), and 560 mL of a toluene solution containing 44 g (0.15 mol) of 1-(4-bromophenyl)naphthalene was added thereto. This mixture was degassed by being stirred while the pressure was reduced. After the degassing, the atmosphere in the flask was replaced with nitrogen. Then, 14 mL (7.0 mmol) of tri(tert-butyl)phosphine (a 10 wt % hexane solution) was added, and the obtained mixture was stirred under a nitrogen stream at 110° C. for two hours.

The mixture was cooled to room temperature, and a solid was separated by suction filtration. The obtained filtrate was concentrated to give a dark brown liquid. The dark brown liquid and toluene were combined, and the obtained solution was filtrated through Celite, alumina, and Florisil. The obtained filtrate was concentrated to give a light yellow liquid. The light yellow liquid was recrystallized from acetonitrile, whereby 53 g of an objective light yellow powder was obtained in a yield of 78%.

Step 1-3: Synthesis of N-(4-bromophenyl)-9,9-dimethyl-N-[4-(1-naphthyl)phenyl]-9H-fluoren-2-amine Synthesis Scheme (a-3) of Step 1-3 is shown.

[Chemical formula 31]

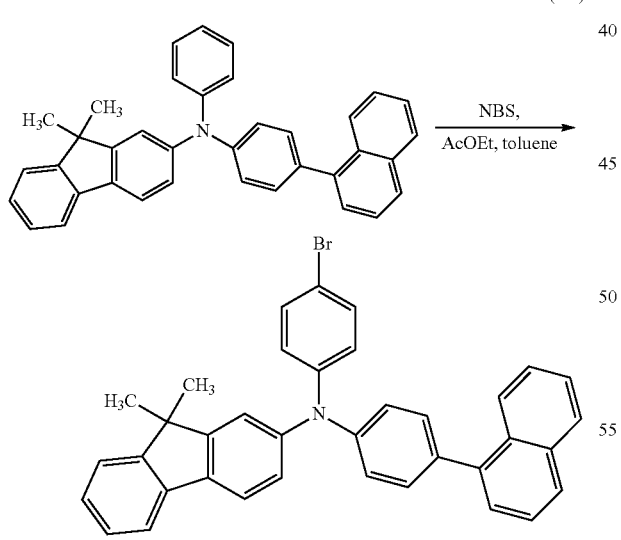

(a-3)

Into a 2-L Meyer flask were put 59 g (0.12 mol) of 9,9-dimethyl-N-(4-naphthyl)phenyl-N-phenyl-9H-fluoren-2-amine and 300 mL of toluene, and the mixture was stirred while being heated. The obtained solution was allowed to cool to room temperature, and 300 mL of ethyl acetate was added thereto. To this mixture was added 21 g (0.12 mol) of N-bromosuccinimide (abbreviation: NBS), and the obtained mixture was stirred at room temperature for about 2.5 hours.

To this mixture was added 400 mL of a saturated aqueous solution of sodium hydrogen carbonate, and the mixture was stirred at room temperature. An organic layer of this mixture was washed twice with a saturated aqueous solution of sodium hydrogen carbonate, and washed twice with saturated saline. Then, magnesium sulfate was added thereto and the mixture was dried for two hours. The obtained mixture was subjected to natural filtration to remove magnesium sulfate, and the filtrate was concentrated to give a yellow liquid. This liquid was dissolved in toluene, and the obtained solution was filtrated through Celite, alumina, and Florisil, whereby a light yellow solid was obtained. The obtained light yellow solid was reprecipitated from toluene/acetonitrile, whereby 56 g of an objective white powder was obtained in a yield of 85%.

Step 1-4: Synthesis of PCBNBF

Synthesis Scheme (a-4) of Step 1-4 is shown.

[Chemical formula 32]

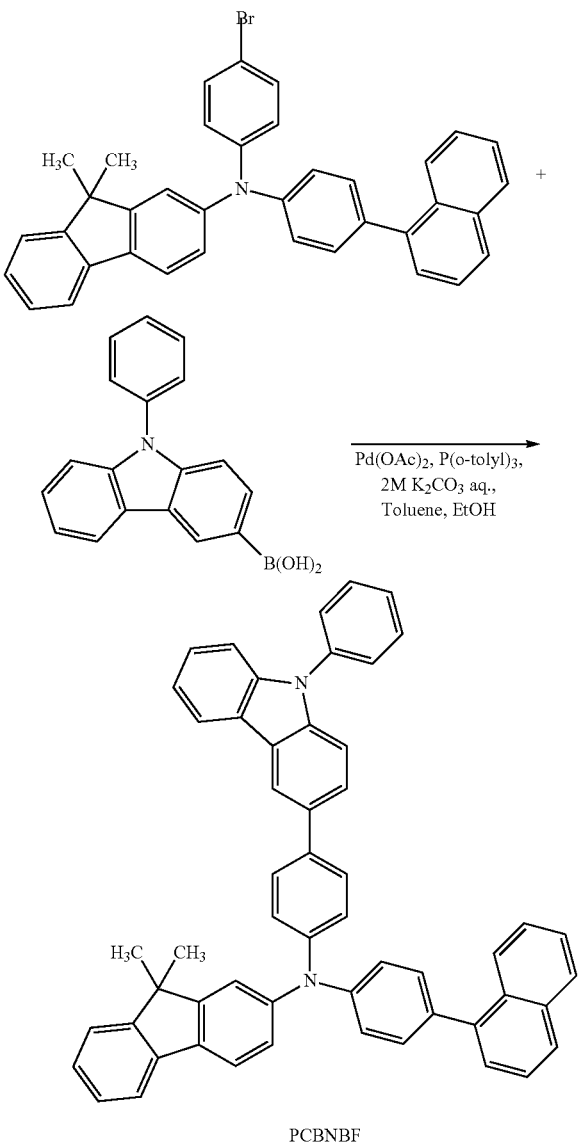

(a-4)

PCBNBF

Into a 1-L three-neck flask were put 51 g (90 mmol) of N-(4-bromophenyl)-9,9-dimethyl-N-[4-(1-naphthyl)phenyl]-9H-fluoren-2-amine, 28 g (95 mmol) of 9-phenyl-9H-carbazole-3-boronic acid, 0.4 mg (1.8 mmol) of palladium(II) acetate, 1.4 g (4.5 mmol) of tri(o-tolyl)phosphine, 300 mL of toluene, 100 mL of ethanol, and 135 mL (2.0 mol/L) of a potassium carbonate solution. The mixture was degassed by being stirred while the pressure was reduced. After the degassing, the atmosphere in the flask was replaced with nitrogen. The mixture was stirred under a nitrogen stream at 90° C. for 1.5 hours. After the stirring, the mixture was allowed to cool to room temperature, and the precipitated solid was collected by suction filtration. An organic layer was extracted from the obtained mixture of an aqueous layer and the organic layer, and the organic layer was concentrated to give a brown solid. The brown solid was recrystallized from toluene/ethyl acetate/ethanol, whereby an objective white powder was obtained. The solid collected after the stirring and the white powder obtained by the recrystallization were dissolved in toluene, and then filtrated through Celite, alumina, and Florisil. The obtained solution was concentrated and recrystallized from toluene/ethanol, whereby 54 g of an objective white powder was obtained in a yield of 82%.

By a train sublimation method, 51 g of the obtained white powder was purified by sublimation. In the purification by sublimation, the white powder was heated at 360° C. under a pressure of 3.7 Pa with a flow rate of argon gas of 15 mL/min. After the purification by sublimation, 19 g of an objective light yellow solid was obtained at a collection rate of 38%.

By a nuclear magnetic resonance (NMR) method, this compound was identified as 9,9-dimethyl-N-[4-(1-naphthyl)phenyl]-N-[4-(9-phenyl-9H-carbazol-3-yl)phenyl]-9H-fluoren-2-amine (abbreviation: PCBNBF), which was an objective substance.

$^1$H NMR data of the obtained substance are as follows: $^1$H NMR (CDCl$_3$, 500 MHz): δ=1.50 (s, 6H), 7.21 (dd, J=8.0 Hz, 1.6 Hz, 1H), 7.26-7.38 (m, 8H), 7.41-7.44 (m, 5H), 7.46-7.55 (m, 6H), 7.59-7.69 (m, 9H), 7.85 (d, J=8.0 Hz, 1H), 7.91 (dd, J=7.5 Hz, 1.7 Hz, 1H), 8.07-8.09 (m, 1H), 8.19 (d, J=8.0 Hz, 1H), 8.37 (d, J=1.7 Hz, 1H).

Figure 7A:
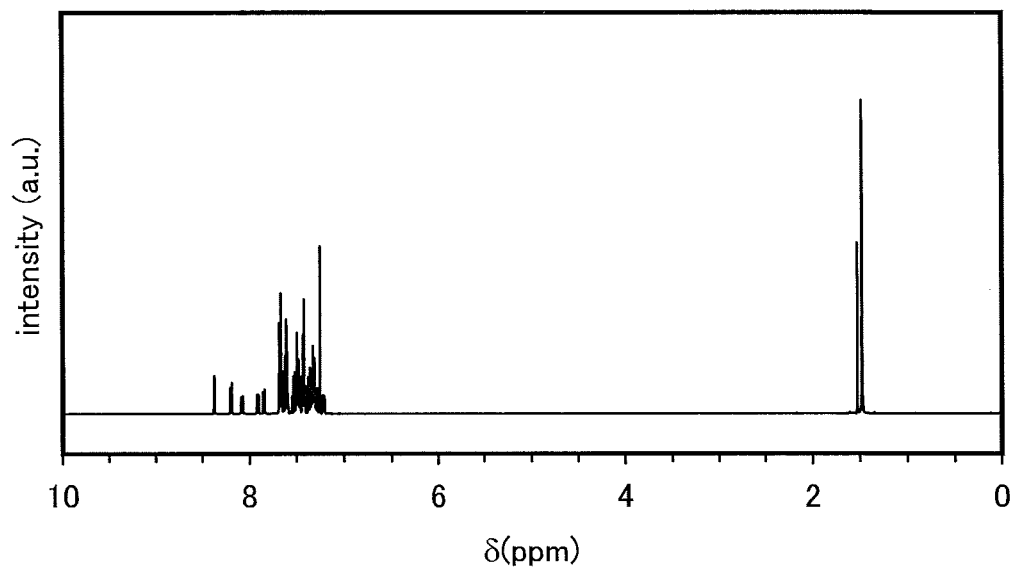
FIGS. 7A and 7B are $^1$H NMR charts of 9,9-dimethyl-N-[4-(1-naphthyl)phenyl]-N-[4-(9-phenyl-9H-carbazol-3-yl)phenyl]-9H-fluoren-2-amine (abbreviation: PCBNBF).
Figure 7B:
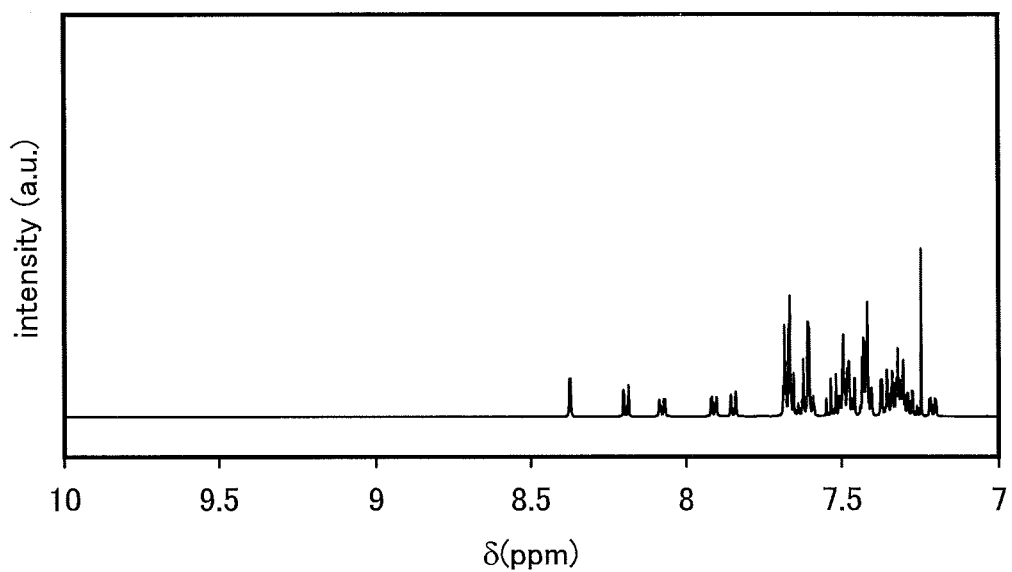

The $^1$H-NMR chart is shown in FIGS. 7A and 7B. Note that FIG. 7B is a chart showing an enlarged part of FIG. 7A in the range of 7.00 ppm to 10.0 ppm.

Synthesis Method 2

Step 2-1: Synthesis of 1-(4-aminophenyl)naphthalene

Synthesis Scheme (b-1) of Step 2-1 is shown.

[Chemical formula 33]

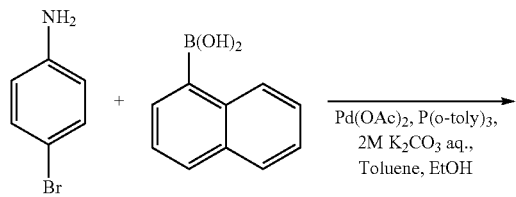

(b-1)

Into a 2-L three-neck flask were put 25 g (0.15 mol) of 4-bromoaniline, 25 g (0.15 mol) of 1-naphthaleneboronic acid, 450 mL of toluene, and 150 mL of ethanol. While the pressure was reduced, this mixture was degassed by being stirred. After the degassing, the atmosphere in a system was replaced with nitrogen. Into the solution was added 220 mL (2.0 mol/L) of a potassium carbonate solution. The obtained mixture was degassed by being stirred while the pressure was reduced, and then, the atmosphere in the system was replaced with nitrogen. To this mixture were added 0.48 g (2.1 mmol) of palladium(II) acetate and 2.4 g (7.9 mmol) of tris(2-methylphenyl)phosphine, and the obtained mixture was stirred under a nitrogen stream at 80° C. for three hours. After the stirring, this mixture was allowed to cool to room temperature, and an aqueous layer of this mixture was extracted three times with toluene. The extracted solution and an organic layer were combined and washed twice with water and washed twice with saturated saline. Into this mixture was added magnesium sulfate, and the mixture was dried for 18 hours. The obtained mixture was subjected to natural filtration to remove magnesium sulfate, and the filtrate was concentrated to obtain an orange liquid. This orange liquid was dissolved in toluene, and this solution was filtrated through Celite, alumina, and Florisil. The obtained filtrate was concentrated to give 33 g of an objective orange liquid in a yield of 99%.

Step 2-2: Synthesis of 4-(1-naphthyl)-4'-(9-phenyl-9H-carbazol-3-yl)diphenylamine>

Synthesis Scheme (b-2) of Step 2-2 is shown.

[Chemical formula 34]

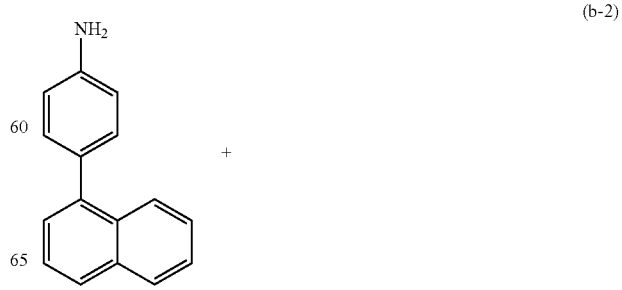

(b-2)

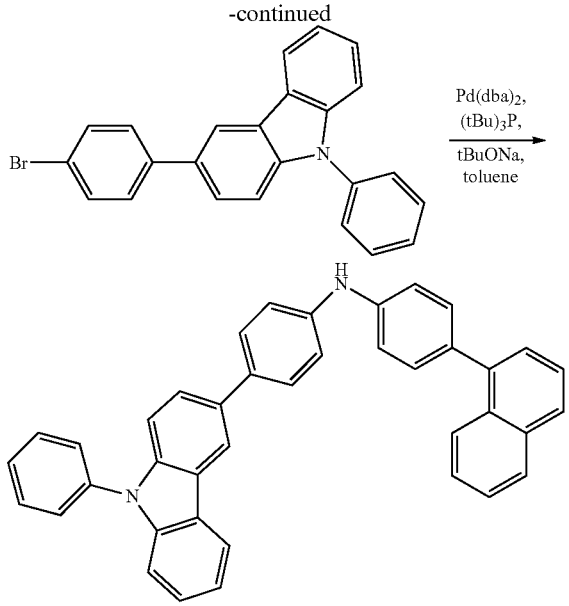

Into a 2-L three-neck flask were put 50 g (0.13 mol) of 3-(4-bromophenyl)-9-phenyl-9H-carbazole, 36 g (0.38 mol) of sodium tert-butoxide, 30 g (0.14 mol) of 4-(1-naphthyl) aniline, and 500 mL of toluene. This mixture was degassed by being stirred while the pressure in a system was reduced. After the degassing, the atmosphere in the system was replaced with nitrogen. Then, into this mixture was added 0.79 g (1.4 mmol) of bis(dibenzylideneacetone)palladium(0) and 13 mL of tri(tert-butyl)phosphine (a 10 wt % hexane solution), and the obtained mixture was stirred at 80° C. for about two hours, and then stirred at 110° C. for three hours. After the stirring, 0.39 g (0.68 mmol) of bis(dibenzylideneacetone)palladium(0) and 4.5 mL of tri(tert-butyl)phosphine (a 10 wt % hexane solution) were added, and the obtained mixture was stirred at 110° C. for three hours. After the heating, the mixture was cooled down to room temperature while being stirred, and was subjected to suction filtration so as to separate a solid. The obtained filtrate was concentrated. The obtained solution was dissolved in toluene, and this solution was filtrated through Celite, alumina, and Florisil. A liquid obtained by concentrating the solution was recrystallized from hexane, whereby a black solid was obtained.

The black solid was dissolved in toluene, and the solution was washed three times with water and washed twice with saturated saline. Magnesium sulfate was added to the organic layer to dry the organic layer, and the mixture was naturally filtered to remove the magnesium sulfate. The obtained filtrate was filtrated through Celite, alumina, and Florisil. The obtained solution was concentrated to give a yellow liquid. This yellow liquid was recrystallized from hexane to give a yellow powder. This yellow powder was suspended in toluene and the resulting mixture was washed by ultrasonic irradiation, whereby 18 g of an objective light yellow powder was obtained in a yield of 27%. The filtrate obtained by the recrystallization and the filtrate resulted from the filtration by the ultrasonic wave irradiation were combined, and then purified by silica gel column chromatography (the ratio of hexane to toluene in a developing solvent was gradually changed from 4:1 to 2:3), whereby a yellow solid was obtained. This yellow solid was recrystallized from toluene, whereby 12 g of an objective light yellow powder was obtained in a yield of 18%. In total, 30 g of the objective light yellow powder was obtained in a yield of 45%. In addition, the filtrate obtained after the recrystallization was concentrated to give 26 g of a yellow solid containing the objective substance.

By a train sublimation method, 22 g of the yellow solid, which was obtained by concentration after the recrystallization, was subjected to purification by sublimation. The purification by sublimation was conducted by heating the yellow solid at 305° C. under a pressure of 2.9 Pa with a flow rate of argon gas of 10 mL/min. After the purification by sublimation, 7.1 g of a light yellow solid was obtained at a collection rate of 38%.

By a train sublimation method, 7.1 g of the light yellow solid, which was obtained by the purification by sublimation, was purified by sublimation. The purification by sublimation was conducted by heating of the light yellow solid at 305° C. under a pressure of 2.2 Pa with a flow rate of argon gas of 10 mL/min. After the purification by sublimation, 5.7 g of an objective light yellow solid was obtained at a collection rate of 80%.

Step 2-3: Synthesis of PCBNBF

Synthesis Scheme (b-3) of Step 2-3 is shown.

[Chemical formula 35]

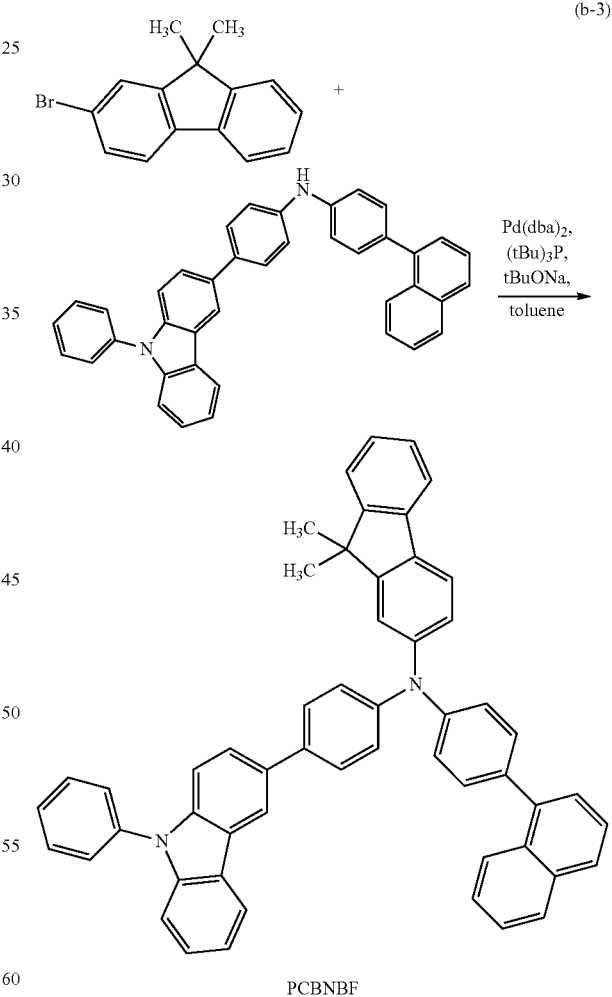

PCBNBF

Into a 100-mL three-neck flask were put 4.7 g (8.8 mmol) of 4-(1-naphthyl)-4'-(9-phenyl-9H-carbazol-3-yl)diphenylamine, 2.6 g (27 mmol) of sodium tert-butoxide, 0.17 g (0.17 mmol) of bis(dibenzylideneacetone)palladium(0), and a solution obtained by dissolving 2.3 g (8.1 mmol) of 2-bromo-9,9'-dimethyl-9H-fluorene in 40 mL of toluene. This mixture was degassed by being stirred while the pressure in a system was reduced, and the atmosphere in the system was replaced with nitrogen. After the degassing, 0.8 mL of tri(tert-butyl) phosphine (a 10 wt % hexane solution) was added to this mixture, and the mixture was refluxed at 110° C. for two hours. After the reflux, the mixture was allowed to cool to room temperature, and filtered through Celite to remove a solid. The obtained filtrate was filtrated through Celite, alumina, and Florisil, whereby an objective light yellow solid was obtained.

This light yellow solid was recrystallized from toluene/ethanol, so that 1.4 g of an objective white powder was obtained. Mother liquor obtained by the recrystallization was concentrated, and a resulting white solid was recrystallized from ethyl acetate/acetonitrile, whereby 2.2 g of an objective white powder was obtained. The total amount of the objective white powder including the one collected in the previous step was 3.6 g and the yield was 59%.

By a train sublimation method, 3.6 g of the obtained white powder was purified by sublimation. In the purification by sublimation, the white powder was heated at 370° C. under a pressure of 3.7 Pa with a flow rate of argon gas of 15 mL/min. After the purification by sublimation, 2.0 g of an objective light yellow solid was obtained at a collection rate of 56%.

By a nuclear magnetic resonance (NMR) method, this compound was identified as PCBNBF, which was an objective substance. Note that $^1$H NMR data of the obtained substance were similar to those of the substance obtained by Synthesis Method 1.

In Synthesis Method 2 described in this example, the yield of 4-(1-naphthyl)-4'-(9-phenyl-9H-carbazol-3-yl)diphenylamine (hereinafter referred to as an objective substance A), which is the objective substance in Step 2-2, was low. This is because 4-(1-naphthyl)-4',4"-bis(9-phenyl-9H-carbazol-3-yl)triphenylamine (hereinafter referred to as a by-product B), which is a compound represented by Structural Formula (900), was generated as a by-product.

[Chemical formula 36]

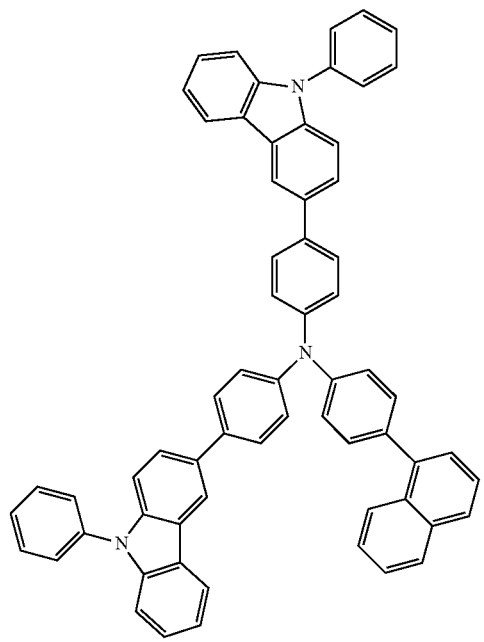

The by-product B has solubility and polarity that are very similar to those of the objective substance A; thus, it was difficult to remove the by-product B by recrystallization or a purification method such as column chromatography.

Here, the by-product B has an extra substituent including a carbazolyl group in comparison with the objective substance A; thus, thermophysical property of the by-product B is higher than that of the objective substance A. For this reason, when purification by sublimation was performed by a train sublimation method to obtain the objective substance A, the by-product B was able to be removed easily.

Note that in the case where synthesis of Step 2-3 is performed using the objective substance A containing a small amount of the by-product B, it is difficult to remove the by-product B by recrystallization or a purification method such as column chromatography because the by-product B has solubility and polarity that are very similar to those of PCBNBF that is the objective substance in Step 2-3. In addition, the molecular weight of the by-product B is close to that of PCBNBF; thus, it is difficult to remove the by-product B by purification by sublimation. Therefore, in the case where PCBNBF is synthesized by Synthesis Method 2, the objective substance A needs to be highly purified.

Accordingly, Synthesis Method 1 is applied to synthesis of PCBNBF, which is an objective substance, in order to highly purify the objective substance A, so that the objective substance A can be obtained without generating the by-product B. Therefore, Synthesis Method 1 is preferred as the method of synthesizing PCBNBF.

Figure 8A:
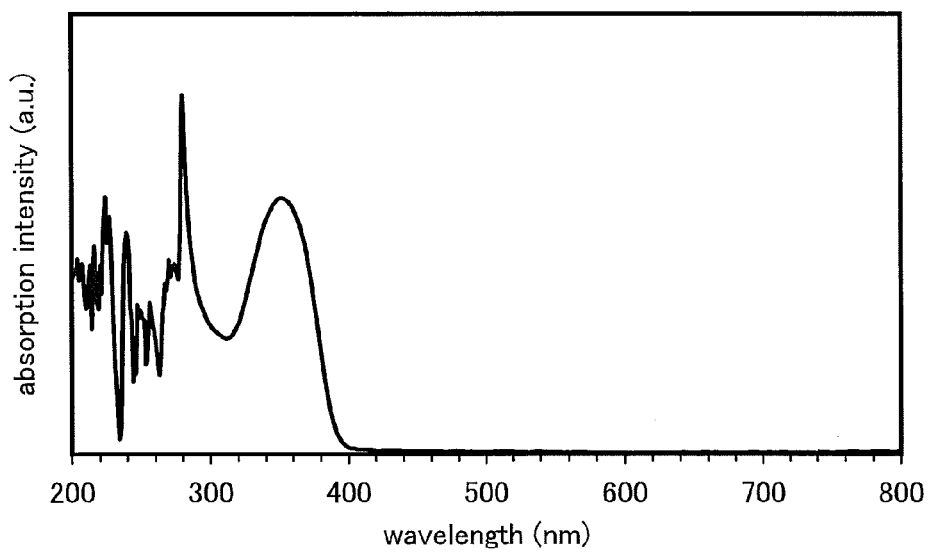
FIGS. 8A and 8B show an absorption spectrum and an emission spectrum of PCBNBF in a toluene solution of PCBNBF.
Figure 8B:
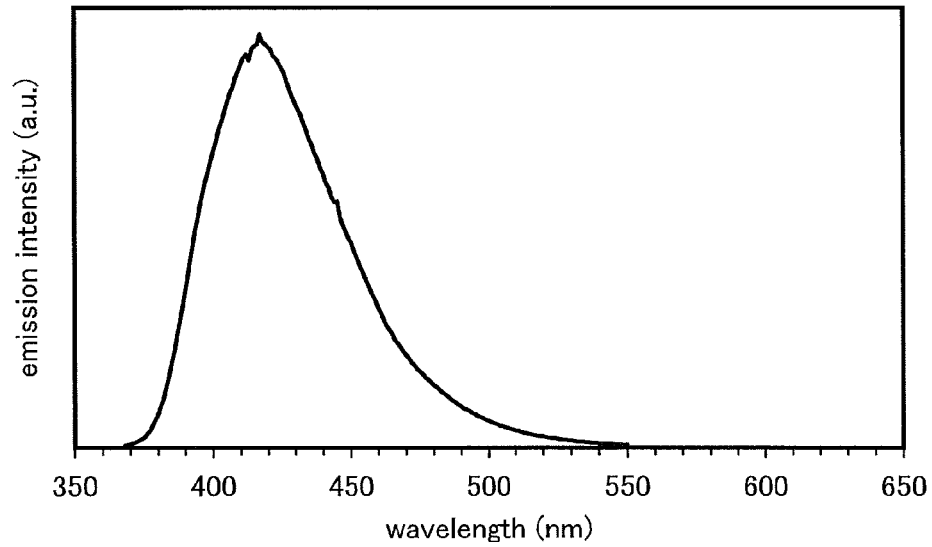
Figure 9A:
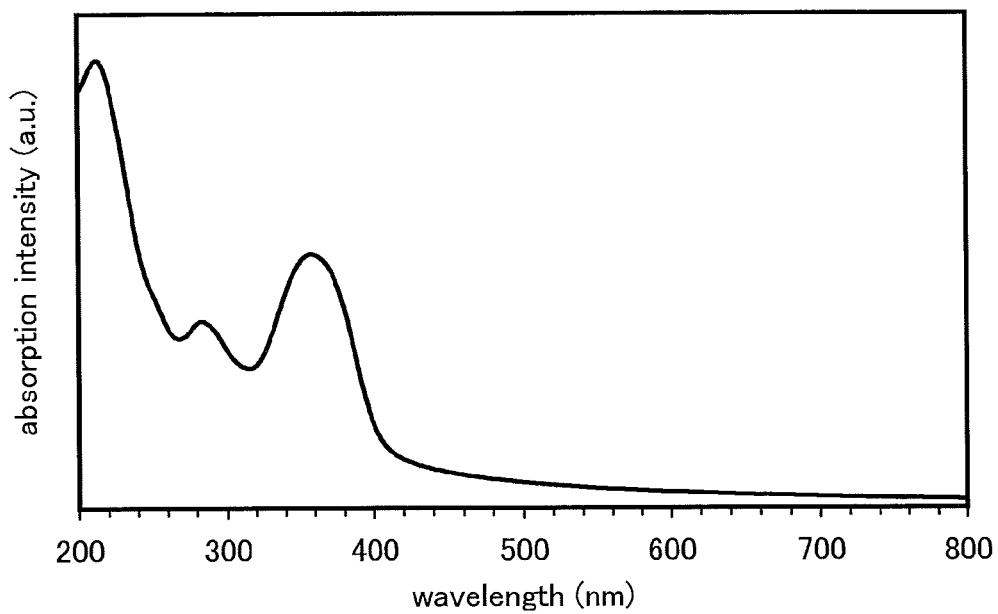
FIGS. 9A and 9B show an absorption spectrum and an emission spectrum of a thin film of PCBNBF.
Figure 9B:
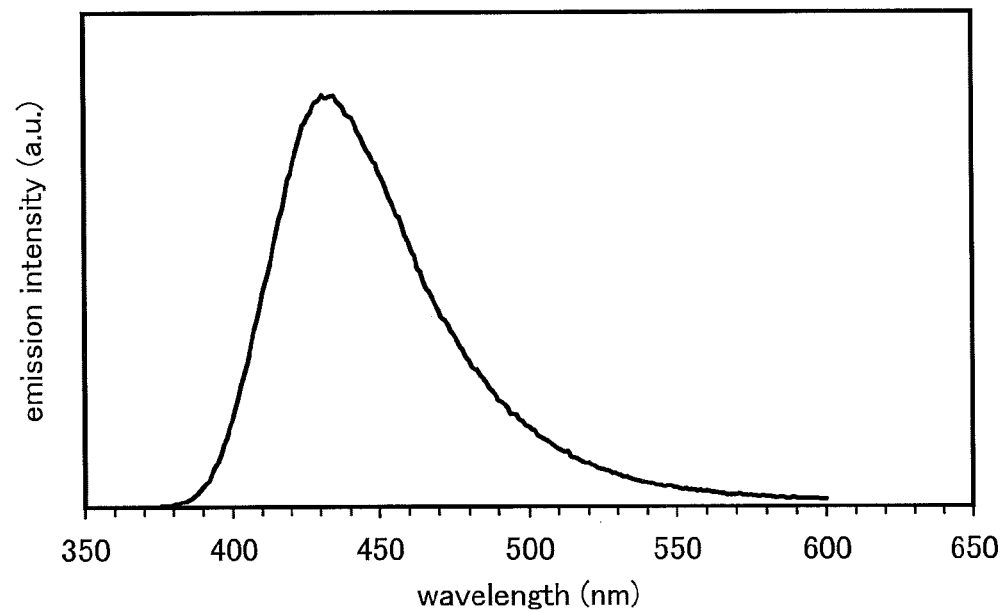

FIG. 8A shows the absorption spectrum of PCBNBF in a toluene solution of PCBNBF, and FIG. 8B shows the emission spectrum thereof. FIG. 9A shows the absorption spectrum of a thin film of PCBNBF, and FIG. 9B shows an emission spectrum thereof. The absorption spectrum was measured with a UV-visible spectrophotometer (V-550, manufactured by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 8A and 8B and FIGS. 9A and 9B, the horizontal axis represents wavelength (nm) and the vertical axis represents intensity (arbitrary unit). In the case of the toluene solution, an absorption peak is observed at around 352 nm, and an emission wavelength peak is observed at 417 nm (an excitation wavelength of 352 nm). In the case of the thin film, absorption peaks are observed at around 212 nm, 283 nm, and 358 nm, and an emission wavelength peak is observed at 434 nm (an excitation wavelength of 371 nm).

Furthermore, mass spectrometry (MS) of PCBNBF was conducted by liquid chromatography mass spectrometry (LC/NIS).

Figure 22A:
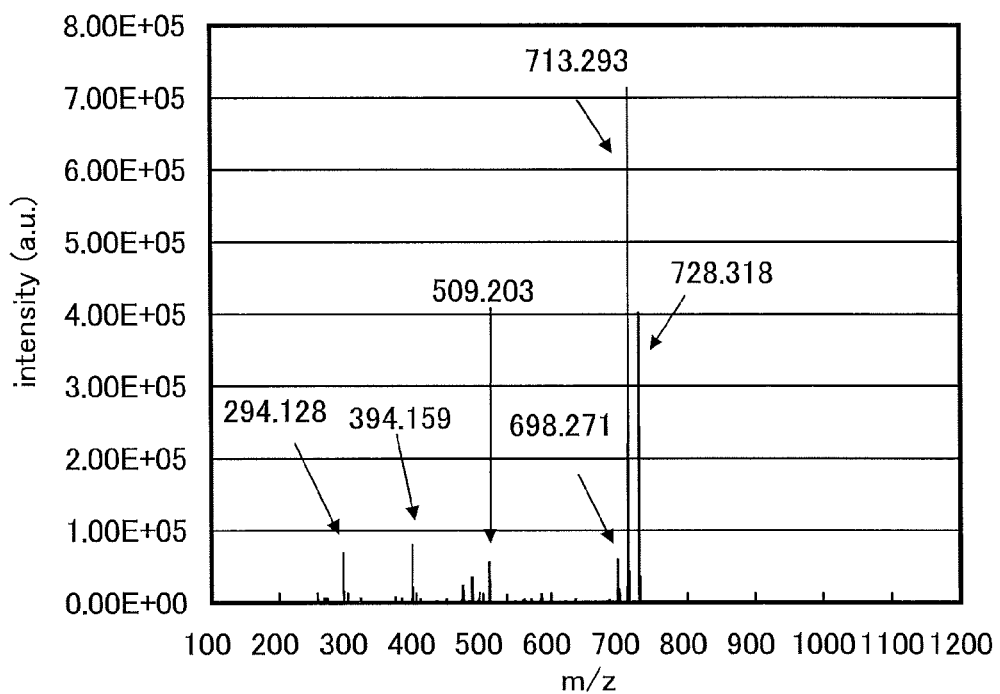
FIGS. 22A and 22B show the results of LC/MS analysis of PCBNBF.
Figure 22B:
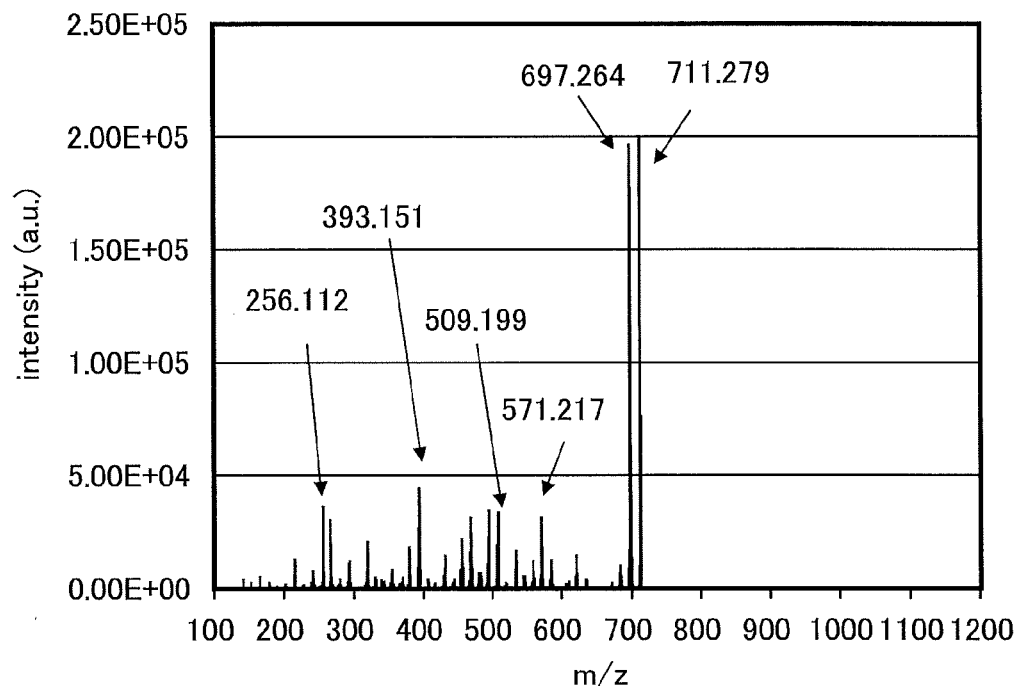

The analysis by LC/MS was carried out with Acquity UPLC (manufactured by Waters Corporation) and Xevo G2 T of MS (manufactured by Waters Corporation). In the MS, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above conditions was collided with an argon gas in a collision cell to dissociate into product ions. Energy (collision energy) for the collision with argon was 50 eV and 70 eV. A mass range for the measurement was m/z 100-1200. FIG. 22A shows the measurement results in the case of a collision energy of 50 eV. FIG. 22B shows the measurement results in the case of a collision energy of 70 eV.

The results in FIG. 22A show that, owing to the presence and absence of hydrogen ions and isotopes, a plurality of product ions of PCBNBF are detected mainly around m/z 728, m/z 713, m/z 698, m/z 509, m/z 394, and m/z 294 in the case of a collision energy of 50 eV.

The results in FIG. 22B show that, owing to the presence and absence of hydrogen ions and isotopes, a plurality of product ions of PCBNBF are detected mainly around m/z 711, m/z 697, m/z 571, m/z 509, m/z 393, and m/z 256 in the case of a collision energy of 70 eV. The results in FIGS. 22A and 22B are characteristically derived from PCBNBF and thus can be regarded as important data in identification of PCBNBF contained in a mixture.

EXAMPLE 2

Synthesis Example 2

In this example, a description will be made of a method of synthesizing N-[4-(9-phenyl-9H-carbazol-3-yl)phenyl]-N-[4-(1-naphthyl)phenyl]-9,9'-spirobi[9H-fluoren]-2-amine (abbreviation: PCBNBSF) represented by Structural Formula (101) shown below.

[Chemical formula 37]

(101)

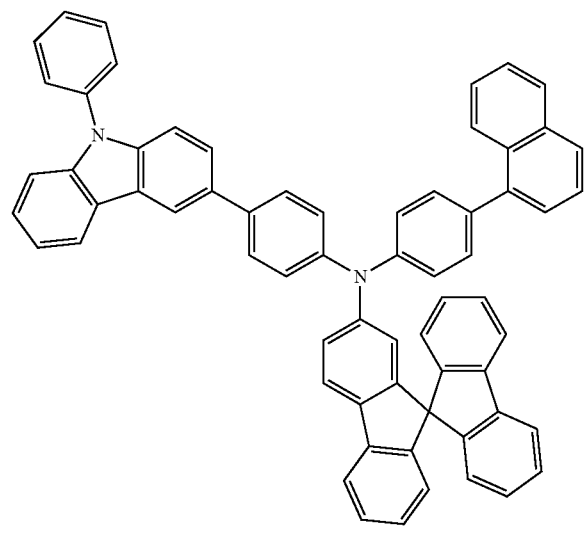

PCBNBSF

Synthesis Scheme (c-1) of PCBNBSF is shown.

[Chemical formula 38]

(c-1)

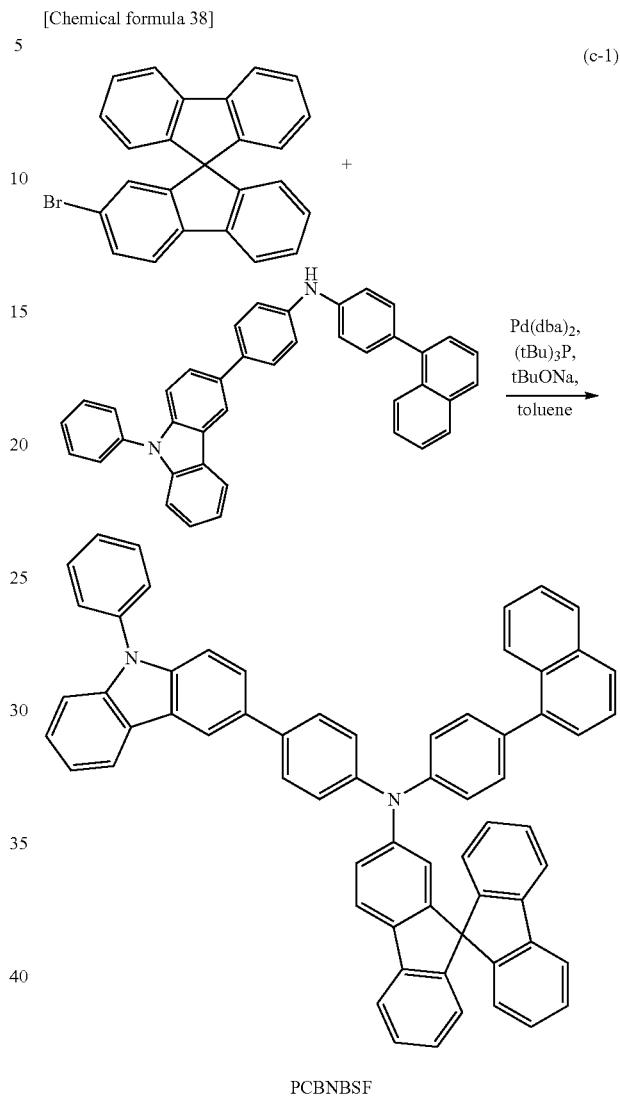

PCBNBSF

Into a 1-L three-neck flask were put 33 g (62 mmol) of 4-(1-naphthyl)-4'-(9-phenyl-9H-carbazol-3-yl)diphenylamine, 23 g (59 mmol) of 2-bromo-9,9'-spirobi[9H-fluorene], 17 g (180 mmol) of sodium tert-butoxide, and 235 mL of toluene. The mixture was degassed by being stirred while the pressure was reduced and then, the atmosphere in the flask was replaced with nitrogen. To the mixture were added 1.5 mL (3.0 mmol) of tri(tert-butyl)phosphine (a 10 wt % hexane solution) and 0.34 g (0.59 mmol) of bis(dibenzylideneacetone)palladium(0). The obtained mixture was stirred under a nitrogen stream at 80° C. for two hours. After the stirring, this mixture was cooled down to room temperature, and the precipitated solid was separated by suction filtration. The obtained filtrate was dissolved in toluene, and this solution was filtrated through Celite and Florisil. The obtained solution was concentrated to give a yellow solid. The yellow solid was recrystallized from ethyl acetate/hexane, so that 47 g of an objective light yellow powder was obtained in a yield of 94%. Note that Example 1 can be referred to for the method of synthesizing 4-(1-naphthyl)-4'-(9-phenyl-9H-carbazol-3-yl) diphenylamine By a train sublimation method, 7.4 g of the obtained light yellow powder was purified by sublimation. In the purification by sublimation, the light yellow powder was heated at 380° C. under a pressure of 3.6 Pa with a flow rate of argon gas of 15 mL/min. After the purification by sublimation, 6.1 g of a light yellow solid was obtained at a collection rate of 82%.

By a train sublimation method, 6.1 g of the light yellow solid, which was obtained by the purification by sublimation, was purified by sublimation. The purification by sublimation was conducted by heating of the light yellow solid at 380° C. under a pressure of 3.6 Pa with a flow rate of argon gas of 15 mL/min. After the purification by sublimation, 5.1 g of an objective light yellow solid was obtained at a collection rate of 83%.

By a nuclear magnetic resonance (NMR) method, this compound was identified as N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), which was an objective substance.

$^1$H NMR data of the obtained substance are as follows: $^1$H NMR (CDCl$_3$, 500 MHz): δ=6.69-6.71 (m, 2H), 6.85 (d, J=7.5 Hz, 2H), 7.06 (t, J=7.5 Hz, 1H), 7.09-7.17 (m, 6H), 7.20 (dd, J=8.0 Hz, 2.3 Hz, 1H), 7.27-7.54 (m, 16H), 7.58-7.63 (m, 5H), 7.74-7.83 (m, 5H), 7.88-7.93 (m, 2H), 8.17 (d, J=7.5 Hz, 1H), 8.28 (d, J=1.7 Hz, 1H).

Figure 10A:
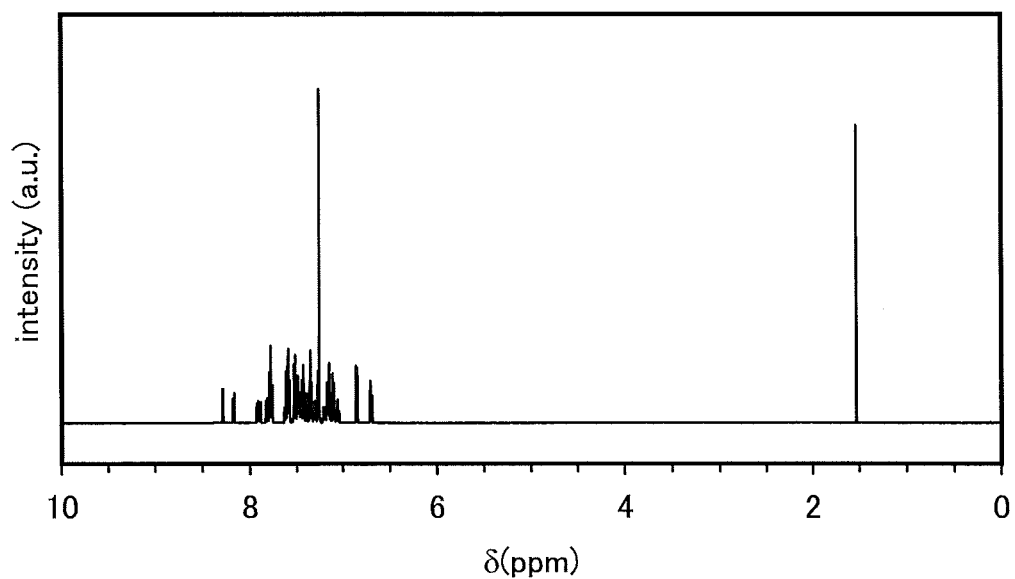
FIGS. 10A and 10B are $^1$H NMR charts of N-[4-(9-phenyl-9H-carbazol-3-yl)phenyl]-N-[4-(1-naphthyl)phenyl]-9,9'-spirobi[9H-fluoren]-2-amine (abbreviation: PCBNBSF).
Figure 10B:
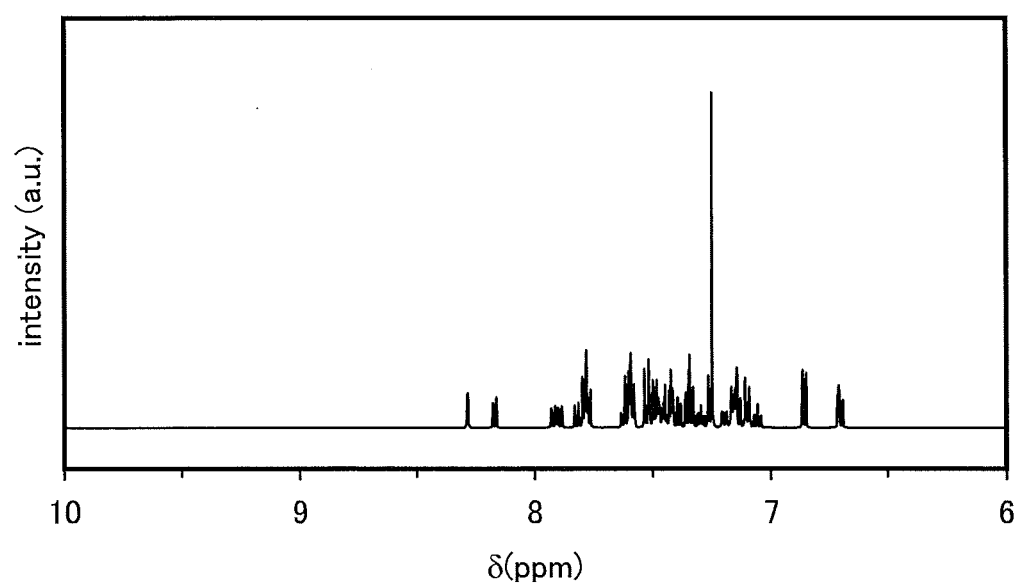

The $^1$H-NMR chart is shown in FIGS. 10A and 10B. Note that FIG. 10B is a chart showing an enlarged part of FIG. 10A in the range of 6.00 ppm to 10.0 ppm.

Figure 11A:
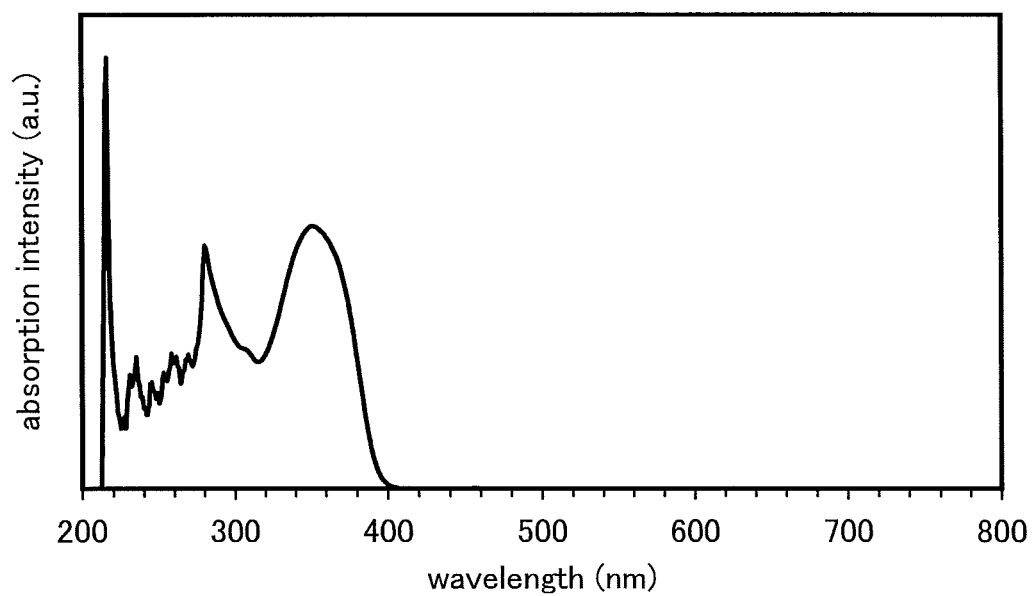
FIGS. 11A and 11B show an absorption spectrum and an emission spectrum of a toluene solution of PCBNBSF.
Figure 11B:
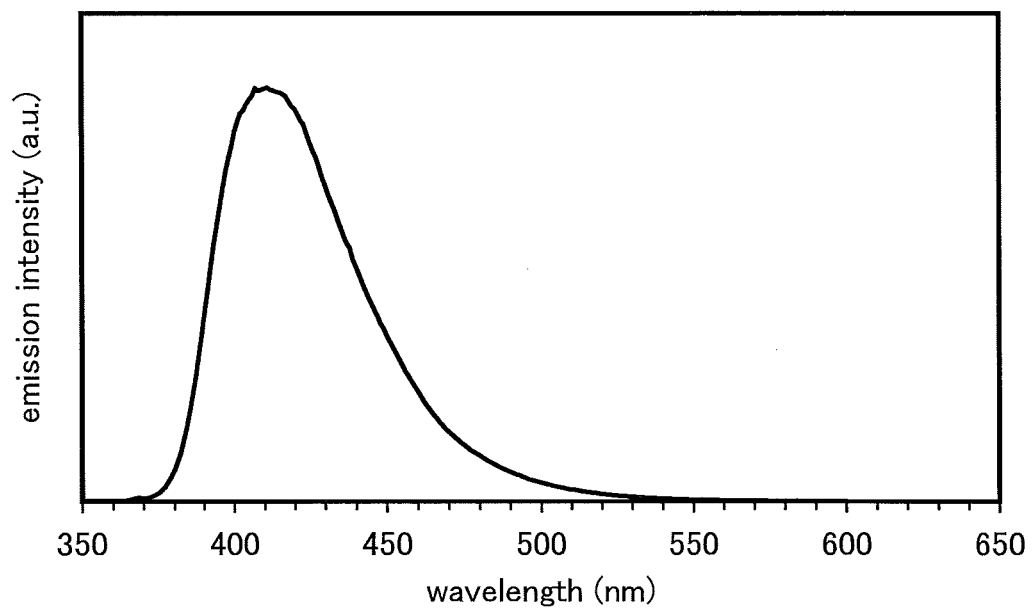
Figure 12A:
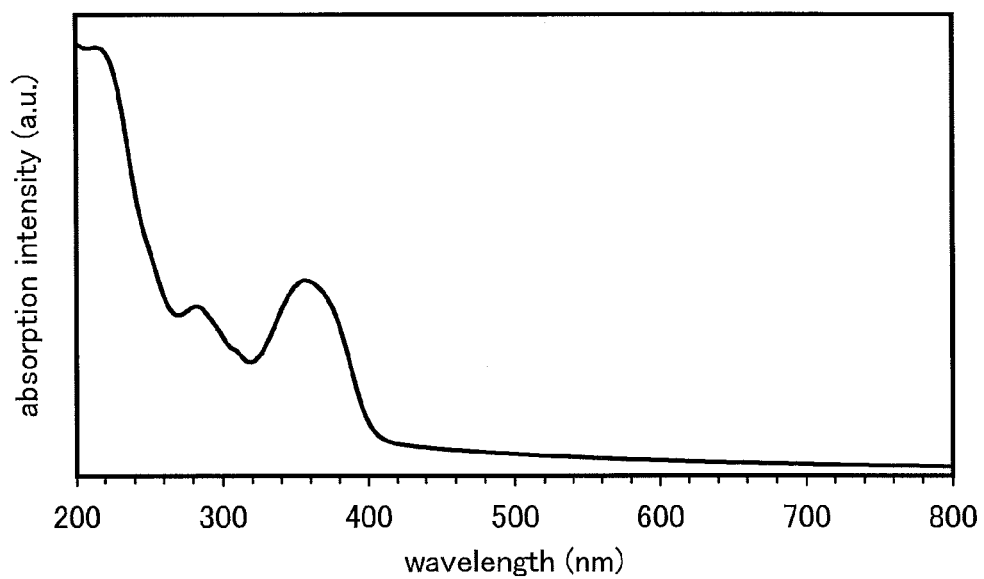
FIGS. 12A and 12B show an absorption spectrum and an emission spectrum of a thin film of PCBNBSF.
Figure 12B:
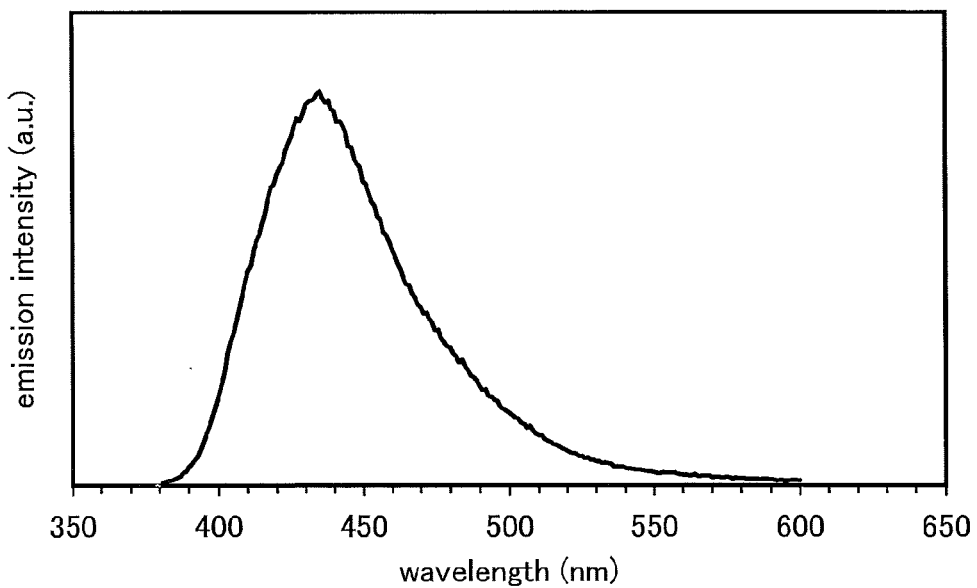

FIG. 11A shows the absorption spectrum of PCBNBSF in a toluene solution of PCBNBSF, and FIG. 11B shows the emission spectrum thereof. FIG. 12A shows the absorption spectrum of a thin film of PCBNBSF, and FIG. 12B shows an emission spectrum thereof. The absorption spectra were measured in the same manner as Example 1. In FIGS. 11A and 11B and FIGS. 12A and 12B, the horizontal axis represents wavelength (nm) and the vertical axis represents intensity (arbitrary unit). In the case of the toluene solution, an absorption peak is observed at around 351 nm, and an emission wavelength peak is observed at 411 nm (an excitation wavelength of 331 nm). In the case of the thin film, an absorption peak is observed at around 366 nm, and an emission wavelength peak is observed at 435 nm (an excitation wavelength of 375 nm).

Furthermore, mass spectrometry (MS) of PCBNBSF was conducted by liquid chromatography mass spectrometry (LC/MS).

Figure 23A:
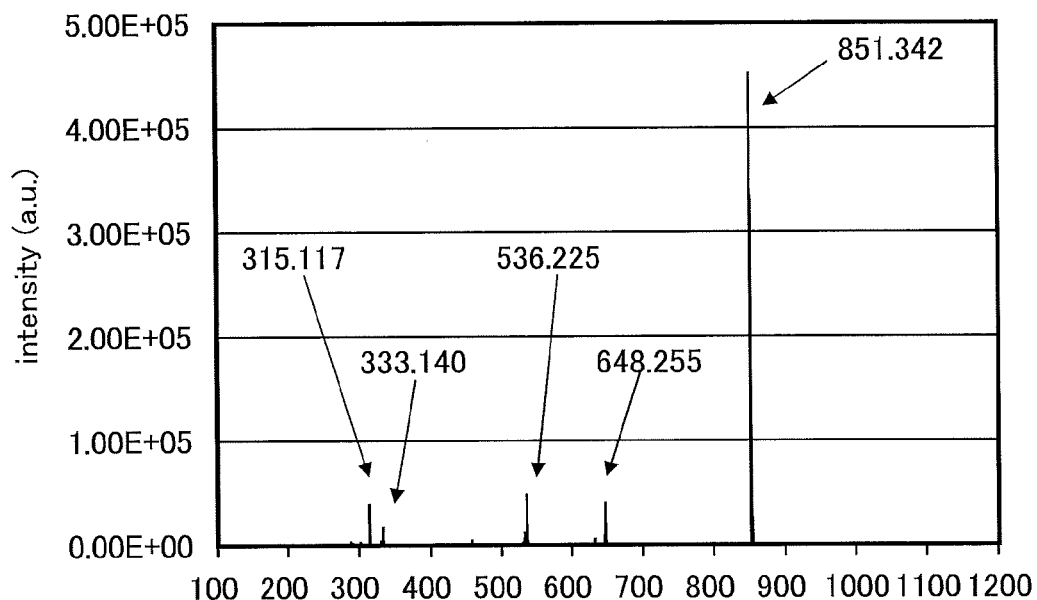
FIGS. 23A and 23B show the results of LC/MS analysis of PCBNBSF.
Figure 23B:
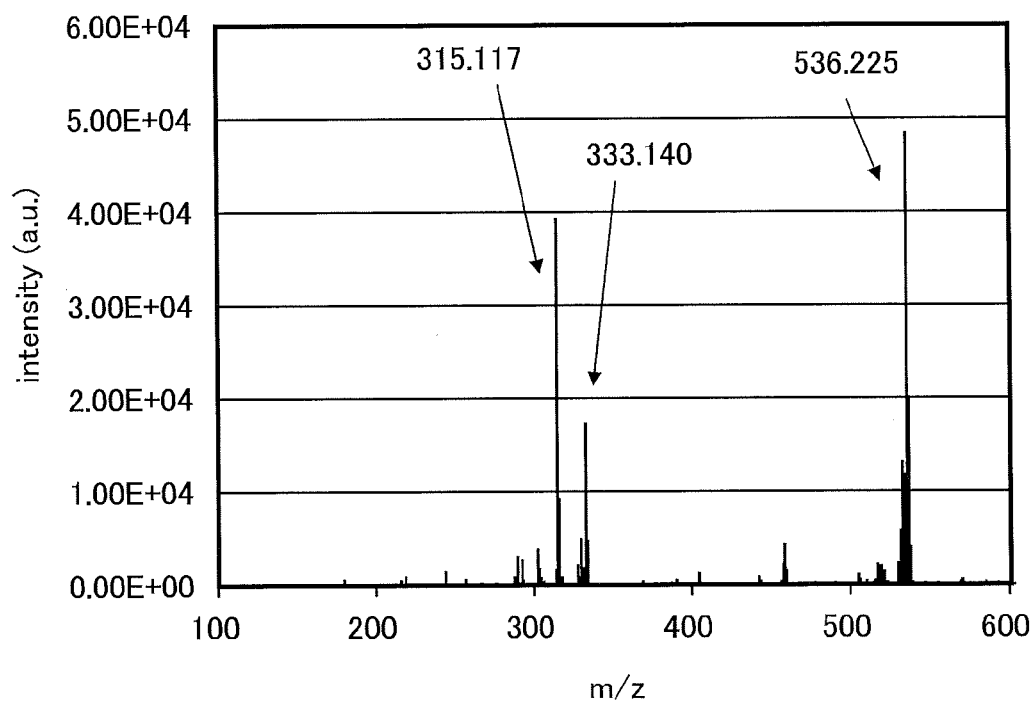

Methods, conditions, and the like for the analysis by LC/MS were the same as those in Example 1. Energy (collision energy) for the collision with argon was 70 eV. A mass range for the measurement was m/z 100-1200. FIGS. 23A and 23B show the measurement results.

The results in FIGS. 23A and 23B show that, owing to the presence and absence of hydrogen ions and isotopes, a plurality of product ions of PCBNBSF are detected mainly around m/z 851, m/z 648, m/z 536, m/z 333, and m/z 315. The results in FIGS. 23A and 23B are characteristically derived from PCBNBSF and thus can be regarded as important data in identification of PCBNBSF contained in a mixture.

EXAMPLE 3

Figure 13:
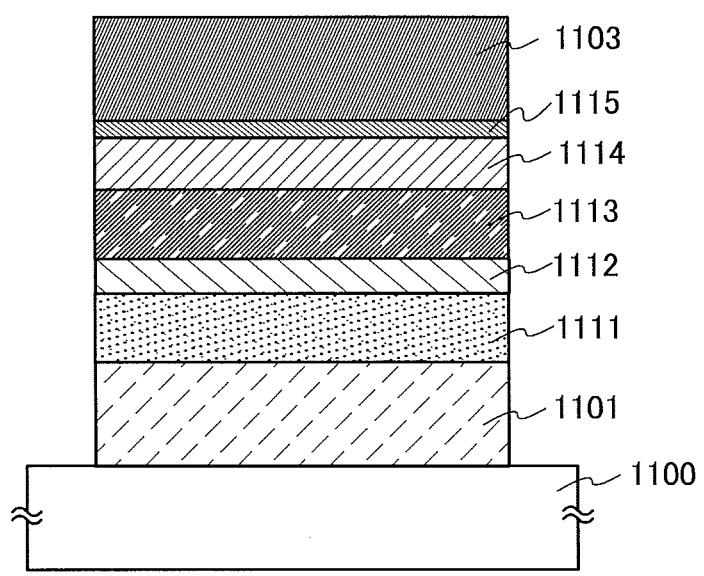
FIG. 13 illustrates a light-emitting element of Example.

In this example, a light-emitting element of one embodiment of the present invention will be described with reference to FIG. 13. Chemical formulae of materials used in this example are shown below.

[Chemical formula 39]

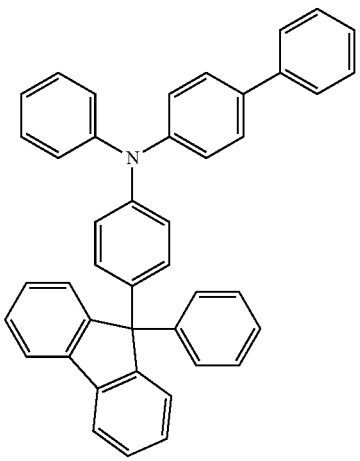

BPAFLP

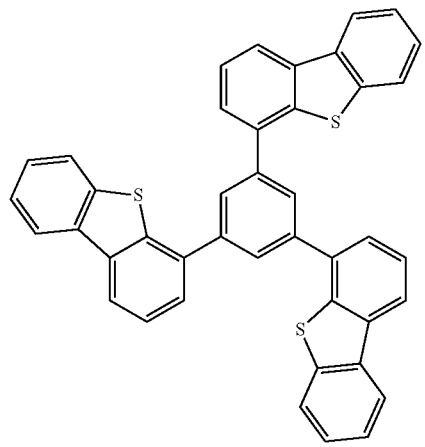

DBTDP-II

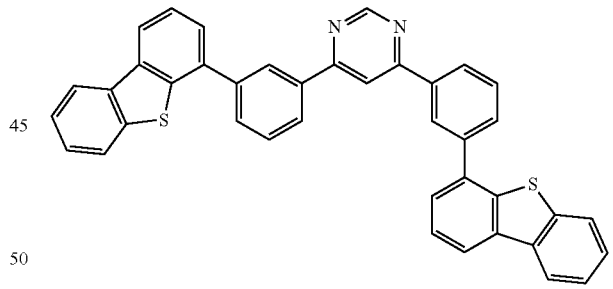

4,6mDBTP2Pm-II

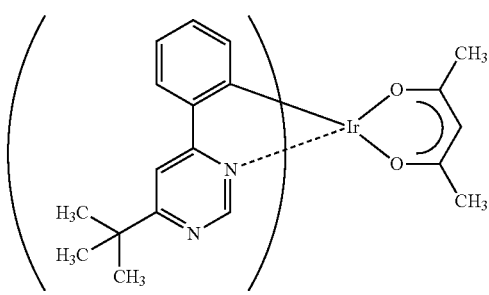

[Ir(tBuppm)$_2$(acac)]

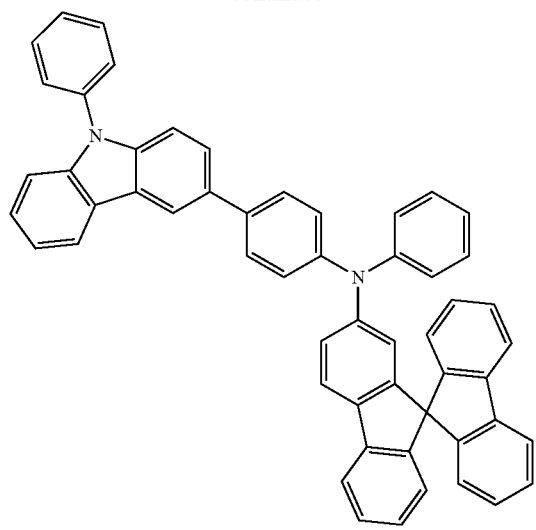

PCBASF

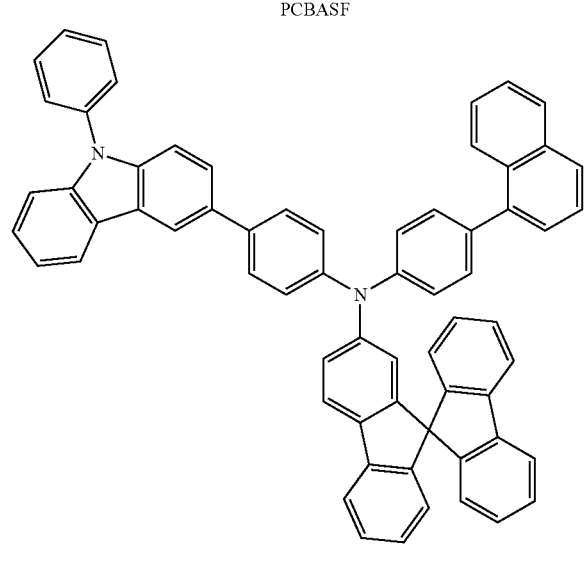

PCBNBSF

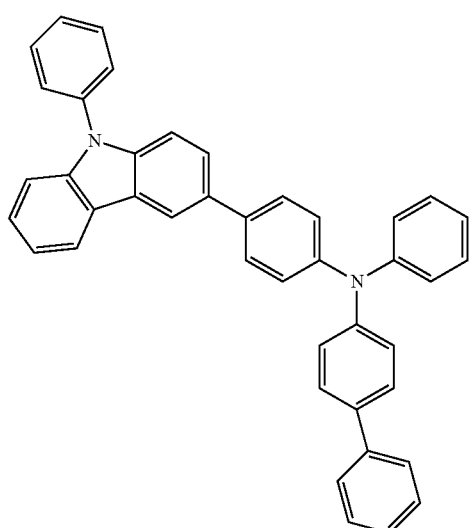

PCBA1BP

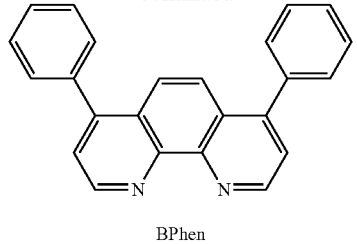

BPhen

Methods of manufacturing a light-emitting element 1, a comparative light-emitting element 2, and a comparative light-emitting element 3 of this example will be described below.

(Light-Emitting Element 1)

First, indium tin oxide containing silicon oxide (ITSO) was deposited over a glass substrate 1100 by a sputtering method, whereby a first electrode 1101 was formed. The thickness was 110 nm and the electrode area was 2 mm×2 mm. Here, the first electrode 1101 functions as an anode of the light-emitting element.

Next, as pretreatment for forming the light-emitting element over the glass substrate 1100, the surface of the substrate was washed with water, baked at 200° C. for one hour, and subjected to UV ozone treatment for 370 seconds.

After that, the glass substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus. Then, the glass substrate 1100 was allowed to cool for about 30 minutes.

Next, the glass substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4,4',4''-(1,3,5-benzenetriyl)tri(dibenzothiophene) (abbreviation: DBT3P-II) and molybdenum (VI) oxide were co-evaporated by an evaporation method using resistance heating to form a hole-injection layer 1111 on the first electrode 1101. The thickness of the hole-injection layer 1111 was set to 40 nm, and the weight ratio of DBT3P-II to molybdenum oxide was adjusted to 4:2 (=DBT3P-II: molybdenum oxide). Note that the co-evaporation method refers to an evaporation method in which evaporation is carried out from a plurality of evaporation sources at the same time in one treatment chamber.

Next, 4-phenyl-4'-(9-phenylfluoren-9-yl)triphenylamine (abbreviation: BPAFLP) was deposited to a thickness of 20 nm over the hole-injection layer 1111, whereby a hole-transport layer 1112 was formed.

A light-emitting layer 1113 was formed over the hole-transport layer 1112 by co-evaporation of 4,6-bis[3-(4-dibenzothienyl)phenyl]pyrimidine (abbreviation: 4,6mDBTP2Pm-II), N-[4-(9-phenyl-9H-carbazol-3-yl)phenyl]-N-[4-(1-naphthyl)phenyl]-9,9'-spirobi[9H-fluoren]-2-amine (abbreviation: PCBNB SF), and (acetylacetonato)bis (6-tert-butyl-4-phenylpyrimidinato)iridium(III) (abbreviation: [Ir(tBuppm)$_2$(acac)]). Here, a 15-nm-thick layer and a 25-nm-thick layer were stacked. The 15-nm-thick layer was formed with the weight ratio of 4,6mDBTP2Pm-II to PCBNBSF to [Ir(tBuppm)$_2$(acac)] adjusted to 0.7:0.3:0.05 (=4,6mDBTP2Pm-II:PCBNBSF:[Ir(tBuppm)$_2$(acac)]). The 25-nm-thick layer was formed with the weight ratio of 4,6mDBTP2Pm-II to PCBNBSF to [Ir(tBuppm)$_2$(acac)] adjusted to 0.8:0.2:0.05 (=4,6mDBTP2Pm-II:PCBNBSF:[Ir(tBuppm)$_2$(acac)]).

Next, over the light-emitting layer 1113, 4,6mDBTP2Pm-II was deposited to a thickness of 10 nm and then bathophenanthroline (abbreviation: BPhen) was deposited to a thickness of 20 nm, so that an electron-transport layer 1114 was formed.

Further, a 1-nm-thick film of lithium fluoride (LiF) was formed over the electron-transport layer 1114 by evaporation, whereby an electron-injection layer 1115 was formed.

Lastly, a 200-nm-thick film of aluminum was formed by evaporation to form a second electrode 1103 functioning as a cathode. Thus, the light-emitting element 1 of this example was manufactured.

Note that, in the above evaporation process, evaporation was all performed by a resistance heating method.

(Comparative Light-Emitting Element 2)

The light-emitting layer 1113 of the comparative light-emitting element 2 was formed by co-evaporation of 4,6mDBTP2Pm-II, 4-phenyl-4'-(9-phenyl-9H-carbazol-3-yl)triphenylamine (abbreviation: PCBA1BP), and [Ir(tBuppm)$_2$(acac)]. Here, a 15-nm-thick layer formed with the weight ratio of 4,6mDBTP2Pm-II to PCBA1BP to [Ir(tBuppm)$_2$(acac)] adjusted to 0.7:0.3:0.05 (=4,6mDBTP2Pm-II:PCBA1BP:[Ir(tBuppm)$_2$(acac)]) and a 25-nm-thick layer formed with the weight ratio of 4,6mDRIP2Pm-II to PCBA1BP to [Ir(tBuppm)$_2$(acac)] adjusted to 0.8:0.2:0.05 (=4,6mDBTP2Pm-II:PCBA1BP:[Ir(tBuppm)$_2$(acac)]) were stacked. The layers other than the light-emitting layer 1113 were formed in the same manner as those in the light-emitting element 1.

(Comparative Light-Emitting Element 3)

The light-emitting layer 1113 of the comparative light-emitting element 3 was formed by co-evaporation of 4,6mDBTP2Pm-II, N-phenyl-N-[4-(9-phenyl-9H-carbazol-3-yl)phenyl]Spiro-9,9'-bifluoren-2-amine (abbreviation: PCBASF), and [Ir(tBuppm)$_2$(acac)]. Here, a 15-nm-thick layer formed with the weight ratio of 4,6mDBTP2Pm-II to PCBASF to [Ir(tBuppm)$_2$(acac)] adjusted to 0.7:0.3:0.05 (=4,6mDBTP2Pm-II:PCBASF:[Ir(tBuppm)$_2$(acac)]) and a 25-nm-thick layer formed with the weight ratio of 4,6mDBTP2Pm-II to PCBASF to [Ir(tBuppm)$_2$(acac)] adjusted to 0.8:0.2:0.05 (=4,6mDBTP2Pm-II:PCBASF:[Ir(tBuppm)$_2$(acac)]) were stacked. The layers other than the light-emitting layer 1113 were formed in the same manner as those in the light-emitting element 1.

Table 1 shows the element structures of the light-emitting elements of this example, which were manufactured in the above manner.

TABLE 1

| | first electrode | hole injection layer | hole-transport layer | light-emitting layer | | electron-transport layer | electron injection layer | second electrode |
|---|---|---|---|---|---|---|---|---|
| light-emitting element 1 | ITSO 110 nm | DBT3P-II: MoOx (=4:2) 40 nm | BPAFLP 20 nm | 4,6 mDBTP2Pm-II:PCBNBSF:[Ir(tBuppm)$_2$(acac)] (=0.7:0.3:0.05) 15 nm | (=0.8:0.2:0.05) 25 nm | 4,6 mDBT P2Pm-II 10 nm | BPhen 20 nm | LiF 1 nm | Al 200 nm |
| comparative light-emitting element 2 | | | | 4,6 mDBTP2Pm-II:PCBA1BP:[Ir(tBuppm)$_2$(acac)] (=0.7:0.3:0.05) 15 nm | (=0.8:0.2:0.05) 25 nm | | | |
| comparative light-emitting element 3 | | | | 4,6 mDBTP2Pm-II:PCBASF:[Ir(tBuppm)$_2$(acac)] (=0.7:0.3:0.05) 15 nm | (=0.8:0.2:0.05) 25 nm | | | |

In a glove box containing a nitrogen atmosphere, each of the light-emitting element 1, the comparative light-emitting element 2, and the comparative light-emitting element 3 was sealed with a glass substrate so as not to be exposed to the air. Then, operation characteristics of these light-emitting elements were measured. Note that the measurement was carried out at room temperature (in an atmosphere kept at 25° C.).

Figure 14:
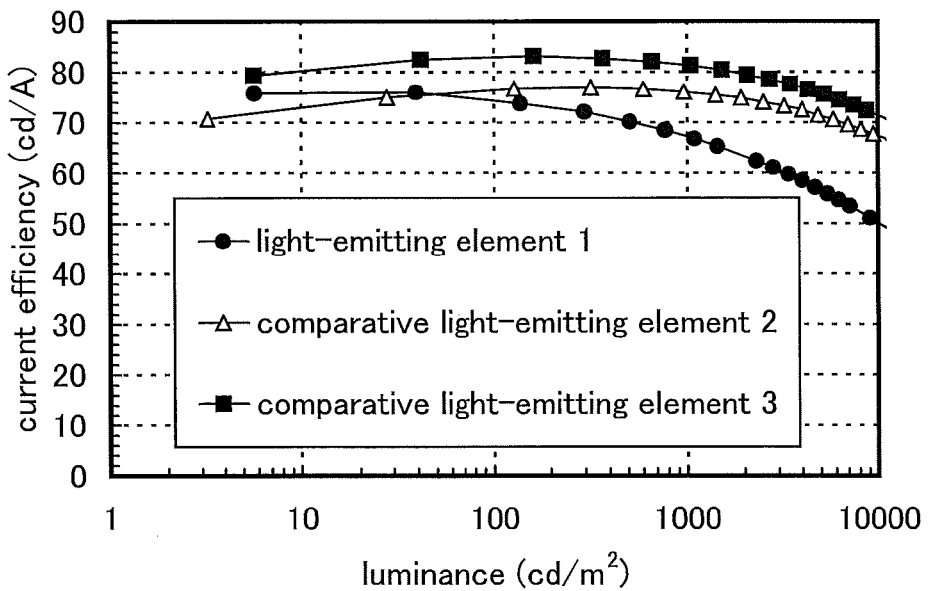
FIG. 14 shows luminance-current efficiency characteristics of light-emitting elements of Example 3.
Figure 15:
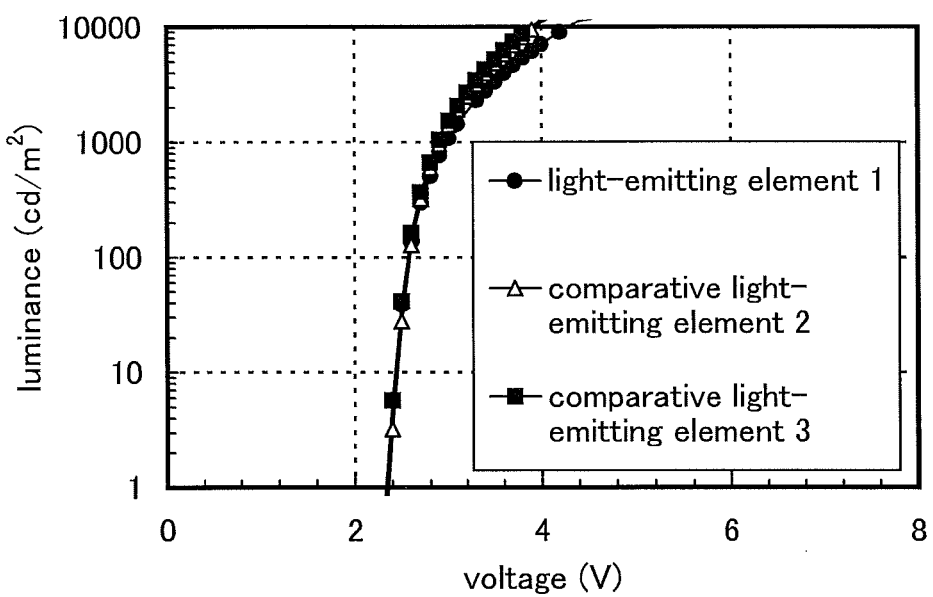
FIG. 15 shows voltage-luminance characteristics of the light-emitting elements of Example 3.
Figure 16:
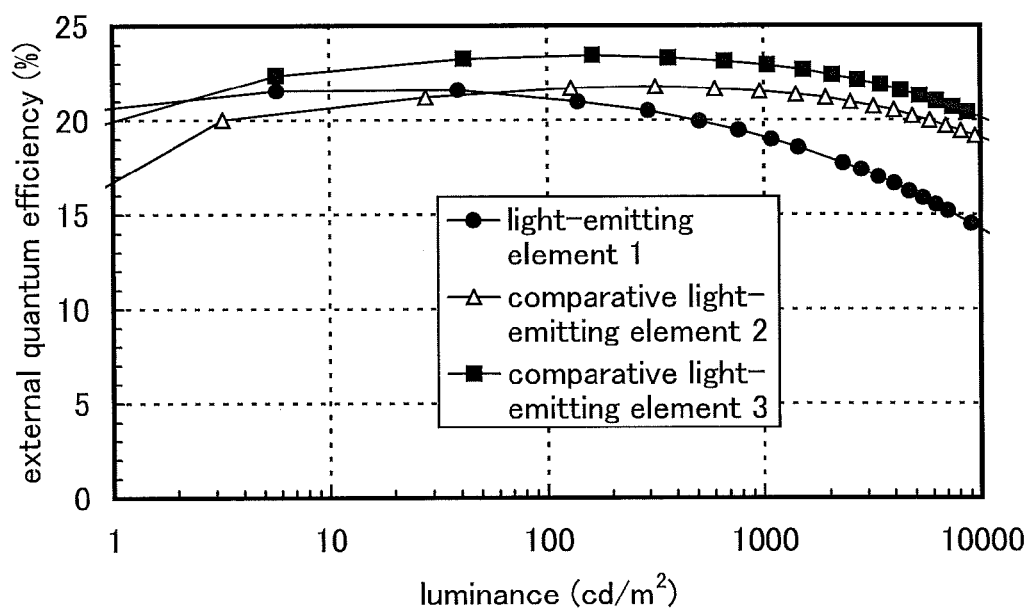
FIG. 16 shows luminance-external quantum efficiency characteristics of the light-emitting elements of Example 3.

FIG. 14 shows luminance-current efficiency characteristics of the light emitting elements of this embodiment. In FIG. 14, the horizontal axis represents luminance (cd/m$^2$) and the vertical axis represents current efficiency (cd/A). FIG. 15 shows voltage-luminance characteristics thereof. In FIG. 15, the horizontal axis represents voltage (V) and the vertical axis represents luminance (cd/m$^2$). FIG. 16 shows luminance-external quantum efficiency characteristics thereof. In FIG. 16, the horizontal axis represents luminance (cd/m$^2$) and the vertical axis represents external quantum efficiency (%). Furthermore, Table 2 shows the voltage (V), current density (mA/cm$^2$), CIE chromaticity coordinates (x, y), current efficiency (cd/A), power efficiency (lm/W), and external quantum efficiency (%) of each light-emitting element at a luminance of around 1000 cd/m$^2$.

TABLE 2

|  | voltage (V) | current density (mA/cm$^2$) | chromaticity | | luminance (cd/m$^2$) | current efficiency (cd/A) | power efficiency (lm/W) | external quantum efficiency (%) |
| --- | --- | --- | --- | --- | --- | --- | --- | --- |
|  |  |  | x | y |  |  |  |  |
| light-emitting element 1 | 3.0 | 1.6 | 0.43 | 0.56 | 1100 | 67 | 70 | 19 |
| comparative light-emitting element 2 | 2.9 | 1.3 | 0.43 | 0.56 | 1000 | 76 | 82 | 22 |
| comparative light-emitting element 3 | 2.9 | 1.3 | 0.43 | 0.56 | 1000 | 81 | 88 | 23 |

As shown in Table 2, as to the light-emitting element 1, the CIE chromaticity coordinates (x, y)=(0.43, 0.56) when the luminance is 1100 cd/m$^2$. As to the comparative light-emitting element 2, the CIE chromaticity coordinates (x, y)=(0.43, 0.56) when the luminance is 1000 cd/m$^2$. As to the comparative light-emitting element 3, the CIE chromaticity coordinates (x, y)=(0.43, 0.56) when the luminance is 1000 cd/m$^2$. These results show that yellow-green light emission originating from [Ir(tBuppm)$_2$(acac)] is obtained from the light-emitting elements of this example.

FIG. 14, FIG. 15, FIG. 16, and Table 2 demonstrate that each of the light-emitting element 1, the comparative light-emitting element 2, and the comparative light-emitting element 3 is driven at a low voltage and has high current efficiency and high external quantum efficiency.

Figure 17:
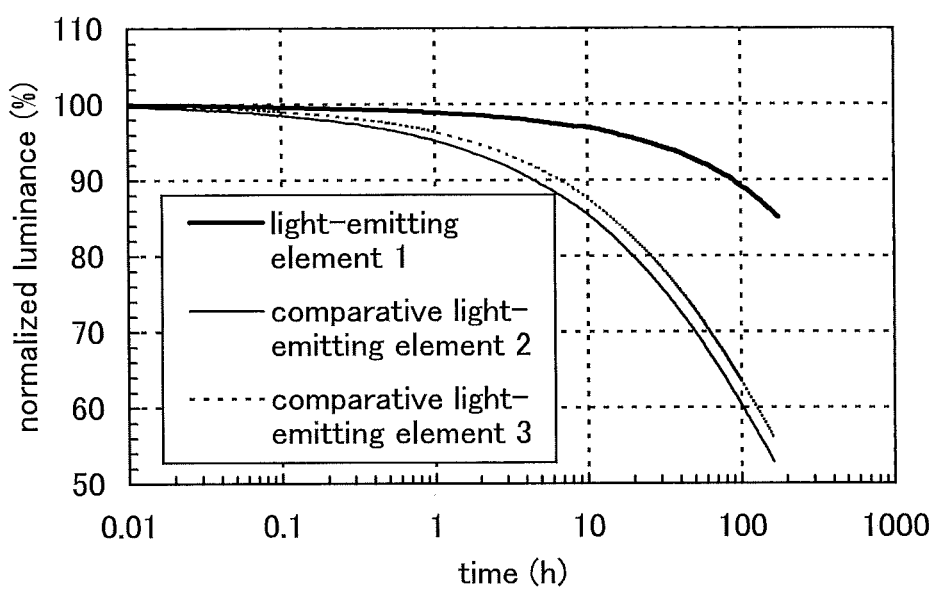
FIG. 17 shows the results of reliability tests of the light-emitting elements of Example 3.

Next, the light-emitting element 1, the comparative light-emitting element 2, and the comparative light-emitting element 3 were subjected to reliability tests. The results of the reliability tests are shown in FIG. 17. In FIG. 17, the vertical axis represents normalized luminance (%) with an initial luminance of 100%, and the horizontal axis represents driving time (h) of the elements. In the reliability tests, the light-emitting elements of this example were driven at room temperature under the conditions that the initial luminance was set to 5000 cd/m$^2$ and the current density was constant. FIG. 17 shows that the light-emitting element 1 keeps its luminance 85% of the initial luminance after the driving for 180 hours. The comparative light-emitting element 2 keeps its luminance 53% of the initial luminance after the driving for 160 hours. The comparative light-emitting element 3 keeps its luminance 56% of the initial luminance after the driving for 160 hours. These results of the reliability tests reveal that the light-emitting element 1 has a longer lifetime than the comparative light-emitting elements 2 and 3.

As described above, PCBNBSF synthesized in Example 2 was used for a light-emitting layer; thus, a light-emitting element with a long lifetime was able to be achieved.

EXAMPLE 4

In this example, a light-emitting element of one embodiment of the present invention will be described with reference to FIG. 13. Chemical formulae of materials used in this example are shown below. Note that the structural formulae of the materials described in Example 3 are omitted.

[Chemical formula 40]

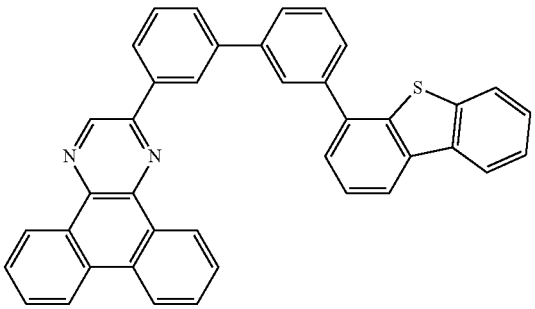

2mDBTBPDBq-II

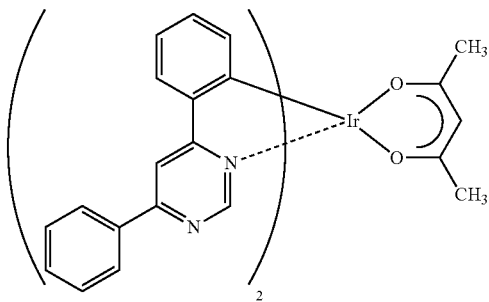

[Ir(dppm)$_2$(acac)]

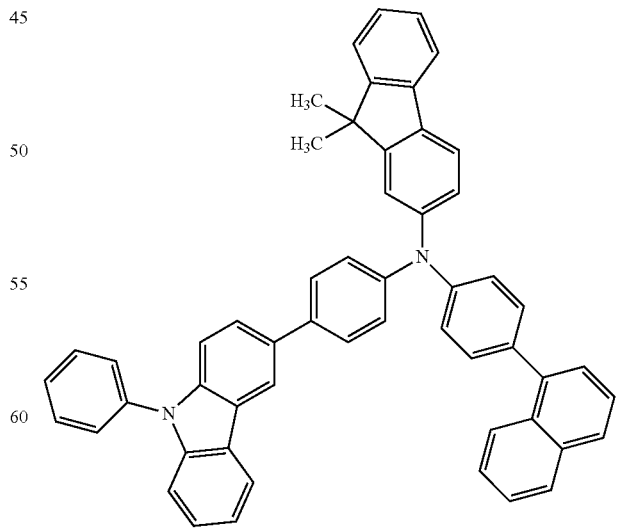

PCBNBF

-continued

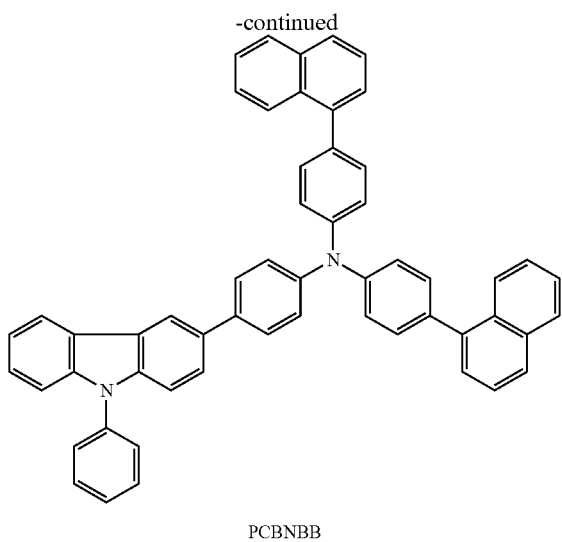

PCBNBB

Lastly, a film of aluminum was formed to a thickness of 200 nm by evaporation, whereby the second electrode 1103 functioning as a cathode was Ruined. Thus, the light-emitting element 4 of this example was manufactured.

Note that, in the above evaporation process, evaporation was all performed by a resistance heating method.

(Comparative Light-Emitting Element 5)

The light-emitting layer 1113 of the comparative light-emitting element 5 was formed by co-evaporation of 2mDBT-BPDBq-II, 4,4'-di(1-naphthyl)-4"-(9-phenyl-9H-carbazol-3-yl)triphenylamine (abbreviation: PCBNBB), and [Ir(dppm)$_2$(acac)]. Here, the weight ratio of 2mDBTBPDBq-II to PCBNBB to [Ir(dppm)$_2$(acac)] was adjusted to 0.8:0.2:0.05 (=2mDBTBPDBq-II: PCBNBB: [Ir(dppm)$_2$(acac)]). The thickness of the light-emitting layer 1113 was set to 40 nm.

The layers other than the light-emitting layer 1113 were formed in the same manner as the light-emitting element 4.

Table 3 shows the element structures of the light-emitting elements of this example, which were manufactured in the above manner.

TABLE 3

| | first electrode | hole injection layer | hole-transport layer | light-emitting layer | electron-transport layer | electron injection layer | second electrode |
|---|---|---|---|---|---|---|---|
| light-emitting element 4 | ITSO 110 nm | DBT3P-II: MoOx (=4:2) 40 nm | BPAFLP 20 nm | 2 mDBTBPDBq-II:PCBNBF: [Ir(dppm)$_2$(acac)] (=0.8:0.2:0.05) 40 nm | 2 mDBT BPDBq-II 15 nm | BPhen 15 nm | LiF 1 nm | Al 200 nm |
| comparative light-emitting element 5 | | | | 2 mDBTBPDBq-II:PCBNBB: [Ir(dppm)$_2$(acac)] (=0.8:0.2:0.05) 40 nm | | | |

Methods of manufacturing a light-emitting element 4 and a comparative light-emitting element 5 of this example will be described below.

(Light-Emitting Element 4)

First, the first electrode 1101, the hole-injection layer 1111, and the hole-transport layer 1112 were formed over the glass substrate 1100 in the same manner as the light-emitting element 1.

Next, the light-emitting layer 1113 was formed over the hole-transport layer 1112 by co-evaporation of 2-[3'-(dibenzothiophen-4-yl)biphenyl-3-yl]dibenzo[f,h]quinoxaline (abbreviation: 2mDBTBPDBq-II), 9,9-dimethyl-N-[4-(1-naphthyl)phenyl]-N-[4-(9-phenyl-9H-carbazol-3-yl)phenyl]-9H-fluoren-2-amine (abbreviation: PCBNBF), and (acetylacetonato)bis(4,6-diphenylpyrimidinato)iridium(III) (abbreviation: [Ir(dppm)$_2$(acac)]). Here, the weight ratio of 2mDBTBPDBq-II to PCBNBF to [Ir(dppm)$_2$(acac)] was adjusted to 0.8:0.2:0.05 (=2mDBTBPDBq-II: PCBNBF: [Ir(dppm)$_2$(acac)]). The light-emitting layer 1113 was formed to have a thickness of 40 nm.

Next, over the light-emitting layer 1113, 2mDBTBPDBq-II was deposited to a thickness of 15 nm and then BPhen was deposited to a thickness of 15 nm, whereby the electron-transport layer 1114 was formed.

Furthermore, LiF was deposited to a thickness of 1 nm over the electron-transport layer 1114 by evaporation, whereby the electron-injection layer 1115 was formed.

In a glove box containing a nitrogen atmosphere, each of the light-emitting element 4 and the comparative light-emitting element 5 was sealed with a glass substrate so as not to be exposed to the air. Then, operation characteristics of these light-emitting elements were measured. Note that the measurement was carried out at room temperature (in an atmosphere kept at 25° C.).

Figure 18:
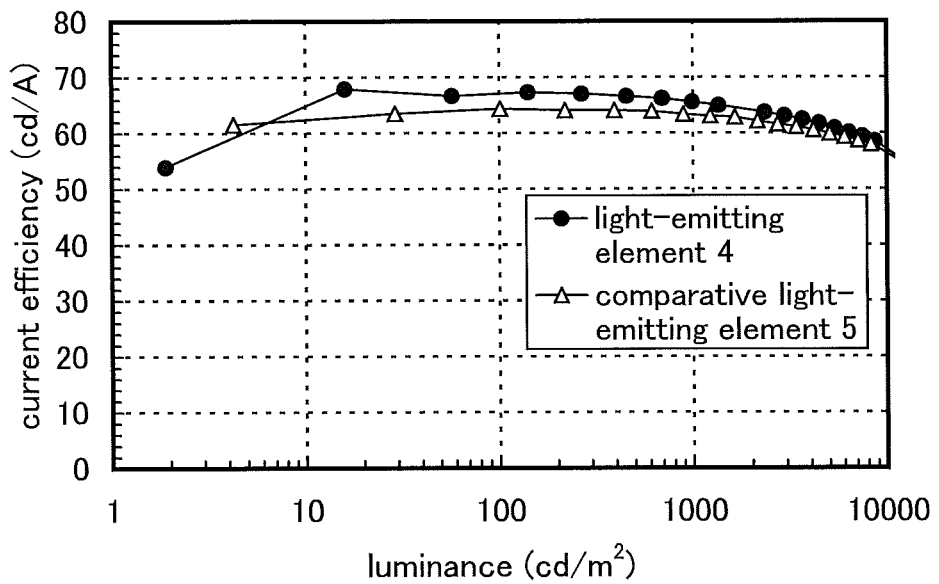
FIG. 18 shows luminance-current efficiency characteristics of light-emitting elements of Example 4.
Figure 19:
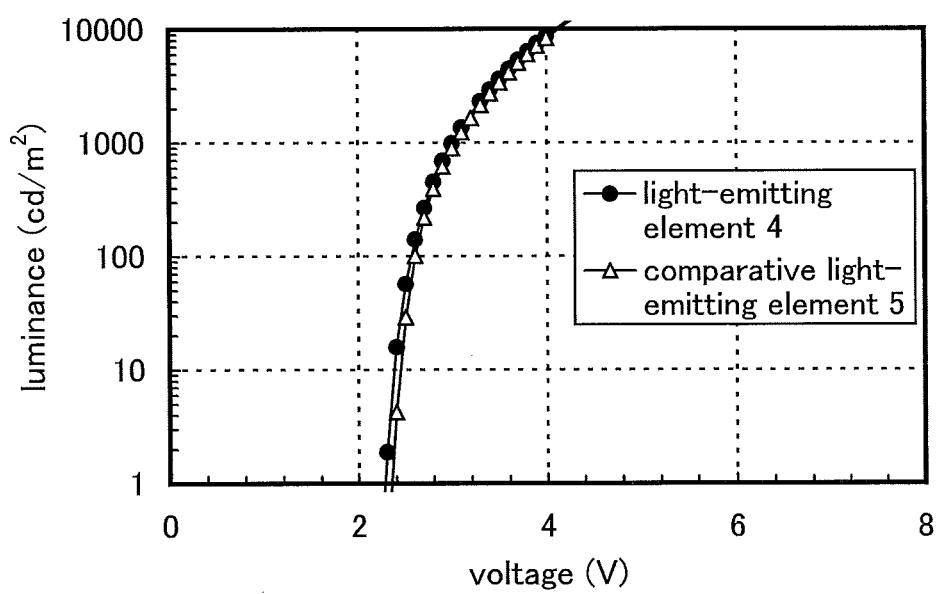
FIG. 19 shows voltage-luminance characteristics of the light-emitting elements of Example 4.
Figure 20:
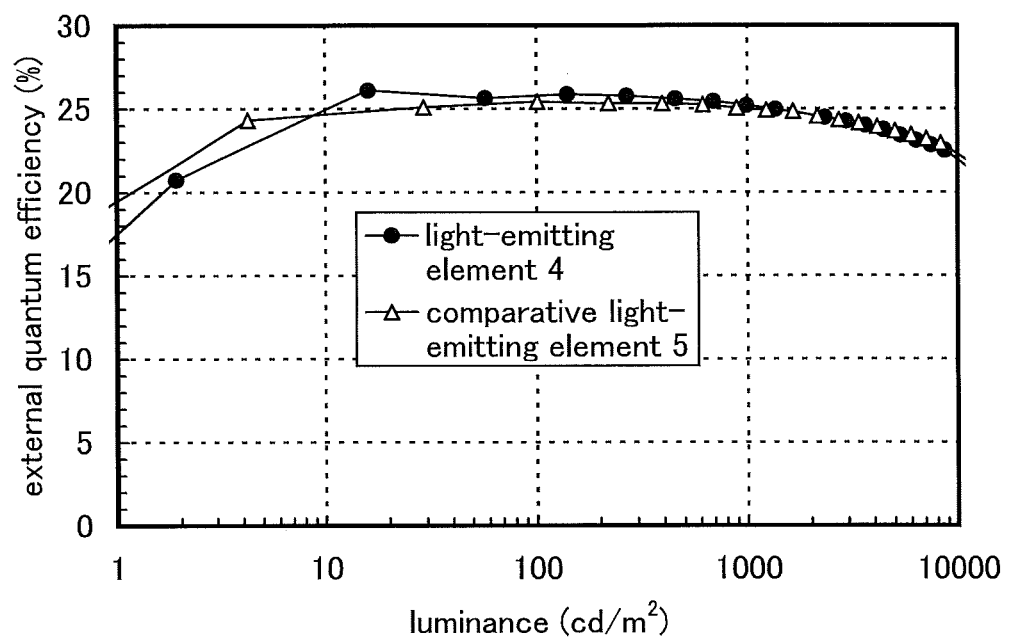
FIG. 20 shows luminance-external quantum efficiency characteristics of the light-emitting elements of Example 4.

FIG. 18 shows luminance-current efficiency characteristics of the light emitting elements of this embodiment. In FIG. 18, the horizontal axis represents luminance (cd/m$^2$) and the vertical axis represents current efficiency (cd/A). FIG. 19 shows voltage-luminance characteristics thereof. In FIG. 19, the horizontal axis represents voltage (V) and the vertical axis represents luminance (cd/m$^2$). FIG. 20 shows luminance-external quantum efficiency characteristics thereof. In FIG. 20, the horizontal axis represents luminance (cd/m$^2$) and the vertical axis represents external quantum efficiency (%). Furthermore, Table 4 shows the voltage (V), current density (mA/cm$^2$), CIE chromaticity coordinates (x, y), current efficiency (cd/A), power efficiency (1 m/W), and external quantum efficiency (%) of each light-emitting element at a luminance of around 1000 cd/m$^2$.

TABLE 4

| | voltage | current density | chromaticity | | luminance | current efficiency | power efficiency | external quantum |
|---|---|---|---|---|---|---|---|---|
| | (V) | (mA/cm$^2$) | x | y | (cd/m$^2$) | (cd/A) | (lm/W) | efficiency (%) |
| light-emitting element 4 | 3.0 | 1.5 | 0.55 | 0.45 | 1000 | 66 | 69 | 25 |
| comparative light-emitting element 5 | 3.0 | 1.4 | 0.55 | 0.44 | 900 | 63 | 66 | 25 |

As shown in Table 4, as to the light-emitting element 4, the CIE chromaticity coordinates (x, y)=(0.55, 0.45) when the luminance is 1000 cd/m$^2$, and as to the comparative light-emitting element 5, the CIE chromaticity coordinates (x, y)= (0.55, 0.44) when the luminance is 900 cd/m$^2$. These results show that orange light emission originating from [Ir(dppm)$_2$(acac)] is obtained from the light-emitting elements of this example.

As can be seen from FIG. 18, FIG. 19, FIG. 20, and Table 4, each of the light-emitting element 4 and the comparative light-emitting element 5 is driven at a low voltage and has high current efficiency and high external quantum efficiency.

Figure 21A:
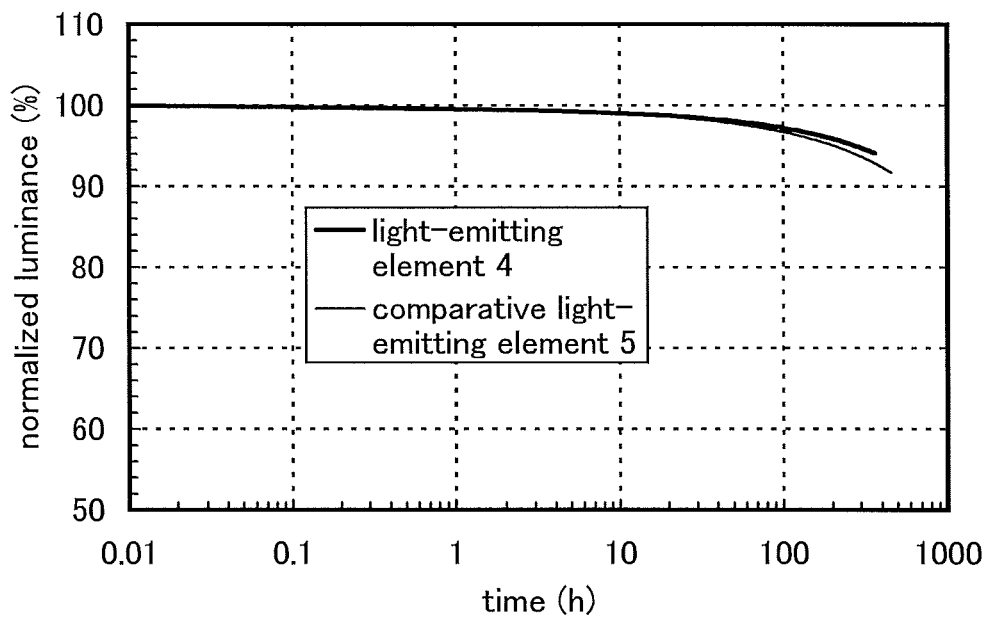
FIGS. 21A and 21B show the results of reliability tests of the light-emitting elements of Example 4.
Figure 21B:
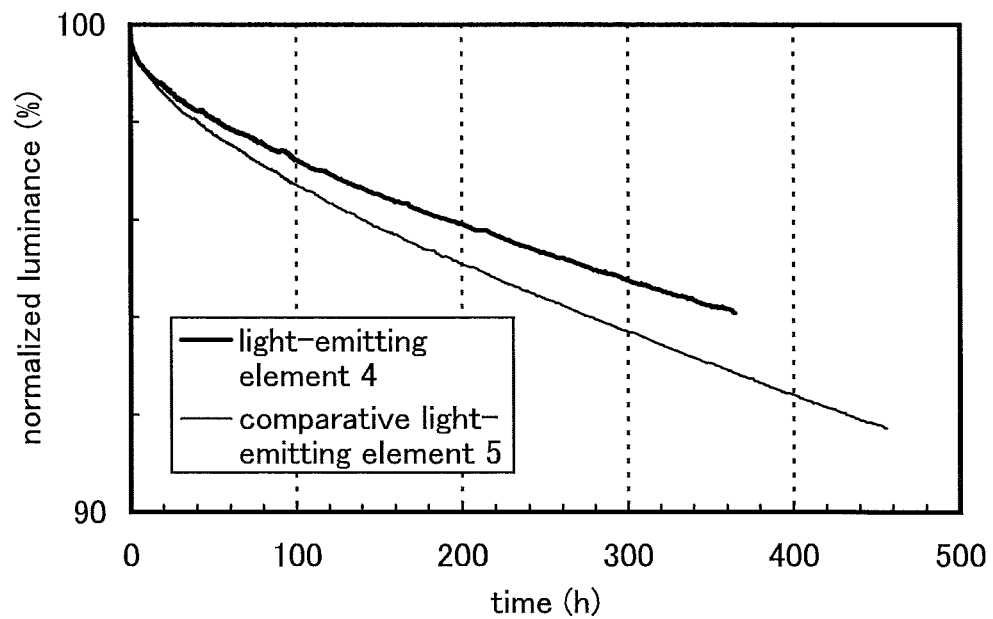

Next, the light-emitting element 4 and the comparative light-emitting element 5 were subjected to reliability tests. The results of the reliability tests are shown in FIGS. 21A and 21B. In FIGS. 21A and 21B, the vertical axis represents normalized luminance (%) with an initial luminance of 100%, and the horizontal axis represents driving time (h) of the elements. In the reliability tests, the light-emitting elements of this example were driven at room temperature under the conditions that the initial luminance was set to 5000 cd/m$^2$ and the current density was constant. FIGS. 21A and 21B show that the light-emitting element 4 keeps its luminance 94% of the initial luminance after the driving for 370 hours, and the comparative light-emitting element 5 keeps its luminance 92% of the initial luminance after the driving for 460 hours. These results of the reliability tests reveal that the light-emitting element 4 has a longer lifetime than the comparative light-emitting element 5.

As described above, PCBNBF synthesized in Example 1 was used for a light-emitting layer; thus, a light-emitting element with a long lifetime was able to be achieved.

Reference Example

A method of synthesizing 4,6-bis[3-(dibenzothiophen-4-yl)phenyl]pyrimidine (abbreviation: 4,6mDBTP2Pm-II) used in Example 4 will be described.

[Chemical formula 41]

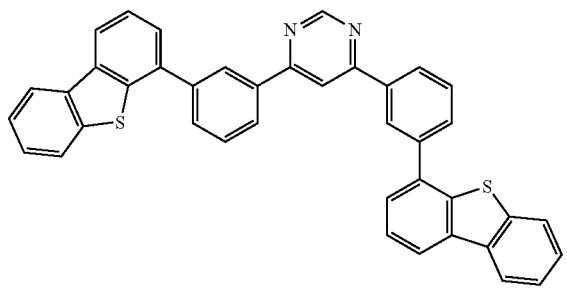

4,6-mDBTP2Pm-II

Synthesis Scheme (x-1) of 4,6mDBTP2Pm-II is shown.

[Chemical formula 42]

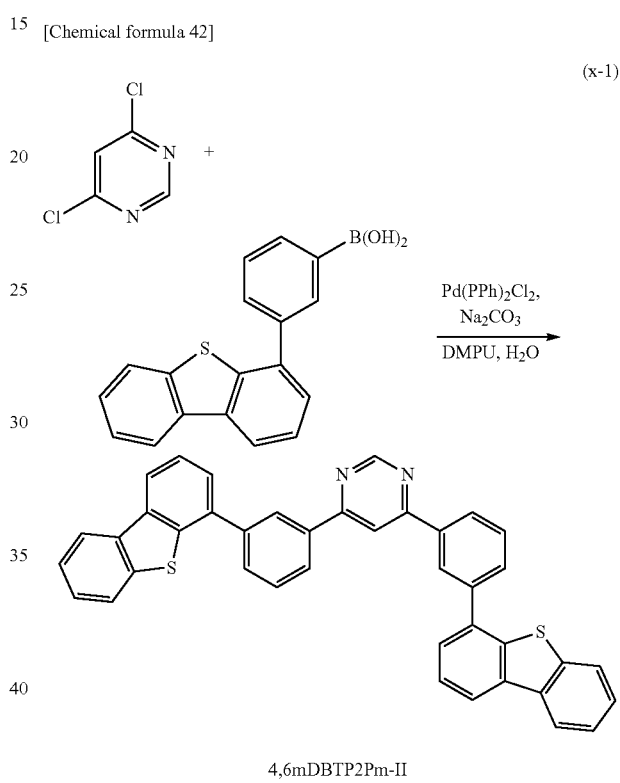

(x-1)

4,6mDBTP2Pm-II

Into a 100-mL recovery flask were put 1.0 g (6.7 mmol) of 4,6-dichloropyrimidine, 5.1 g (17 mmol) of 3-(dibenzothiophen-4-yl)-phenylboronic acid, 3.5 g (34 mmol) of sodium carbonate, 20 mL of 1,3-dimethyl-3,4,5,6-tetrahydro-2(1H)-pyrimidinone (abbreviation: DMPU), and 10 mL of water. This mixture was degassed by being stirred while the pressure was reduced. To this mixture was added 56 mg (81 µmol) of bis(triphenylphosphine)palladium(II) dichloride, and the atmosphere was replaced with argon. The mixture was stirred while the reaction container was heated by irradiation with microwaves (2.45 GHz, 100 W) for 1.5 hours. After the heating, water was added to the mixture, and the mixture was filtered to give a residue. The obtained solid was washed with dichloromethane and ethanol. To the obtained solid was added toluene, and the mixture was subjected to suction filtration through Celite, alumina, and Florisil. The filtrate was concentrated to give a solid. The obtained solid was recrystallized from toluene to give 2.5 g of a white solid in a yield of 63%.

By a train sublimation method, 2.5 g of the obtained solid was purified. The purification by sublimation was performed by heating at 300° C. under a pressure of 3.6 Pa with a flow rate of argon gas of 5 mL/min. After the purification by sublimation, 2.0 g of a white solid was obtained at a collection rate of 79%.

This compound was identified as 4,6-bis[3-(dibenzothiophen-4-yl)phenyl]pyrimidine (abbreviation: 4,6mDBTP2Pm-II), which was an objective substance, by a nuclear magnetic resonance (NMR) method.

$^1$H NMR data of the obtained substance are as follows: $^1$H NMR (CDCl$_3$, 300 MHz): δ=7.41-7.51 (m, 4H), 7.58-7.62 (m, 4H), 7.68-7.79 (m, 4H), 8.73 (dt, J1=8.4 Hz, J2=0.9 Hz, 2H), 8.18-8.27 (m, 7H), 8.54 (t, J1=1.5 Hz, 2H), 9.39 (d, J1=0.9 Hz, 1H).

This application is based on Japanese Patent Application serial no. 2012-172952 filed with Japan Patent Office on Aug. 3, 2012, the entire contents of which are hereby incorporated by reference.

What is claimed is:

1. A light-emitting element comprising a light-emitting layer between a pair of electrodes, the light-emitting layer comprising:
   a light-emitting substance; and
   an organic compound represented by General Formula (G0),

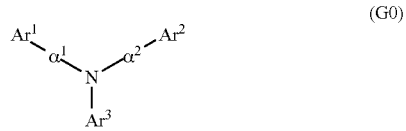

wherein Ar$^1$ represents a naphthyl group,
wherein Ar$^2$ represents a carbazolyl group,
wherein Ar$^3$ represents a fluorenyl group or a spirofluorenyl group,
wherein α$^1$ and α$^2$ each independently represent a phenylene group or a biphenyldiyl group,
wherein the naphthyl group, the carbazolyl group, the fluorenyl group, the spirofluorenyl group, the phenylene group, and the biphenyldiyl group are each independently unsubstituted or substituted with a substituent, and
wherein the substituent is an alkyl group having 1 to 10 carbon atoms or an aryl group having 6 to 25 carbon atoms.

2. The light-emitting element according to claim 1, further comprising a hole-transport layer in contact with the light-emitting layer, the hole-transport layer comprising a second organic compound represented by General Formula (G0),

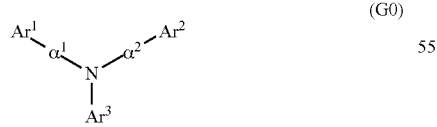

wherein Ar$^1$ represents a naphthyl group,
wherein Ar$^2$ represents a carbazolyl group,
wherein Ar$^3$ represents a fluorenyl group or a spirofluorenyl group,
wherein α$^1$ and α$^2$ each independently represent a phenylene group or a biphenyldiyl group,
wherein the naphthyl group, the carbazolyl group, the fluorenyl group, the spirofluorenyl group, the phenylene group, and the biphenyldiyl group are each independently unsubstituted or substituted with a substituent, and
wherein the substituent is an alkyl group having 1 to 10 carbon atoms or an aryl group having 6 to 25 carbon atoms.

3. The light-emitting element according to claim 1, further comprising a hole-transport layer in contact with the light-emitting layer, the hole-transport layer comprising the organic compound.

4. An electronic device comprising the light-emitting element according to claim 1.

5. A lighting device comprising the light-emitting element according to claim 1.

6. A light-emitting element comprising a light-emitting layer between a pair of electrodes, the light-emitting layer comprising:
   a light-emitting substance; and
   an organic compound represented by General Formula (G1),

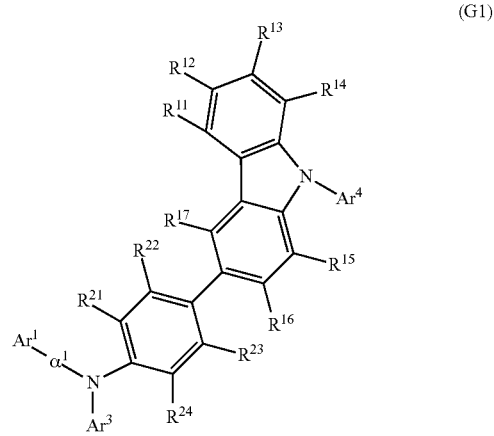

wherein Ar$^1$ represents a naphthyl group,
wherein Ar$^3$ represents a fluorenyl group or a spirofluorenyl group,
wherein Ar$^4$ represents an aryl group having 6 to 25 carbon atoms,
wherein α$^1$ represents a phenylene group or a biphenyldiyl group,
wherein R$^{11}$ to R$^{17}$ and R$^{21}$ to R$^{24}$ each independently represent hydrogen, an alkyl group having 1 to 10 carbon atoms, or an aryl group having 6 to 25 carbon atoms,
wherein the naphthyl group, the fluorenyl group, the spirofluorenyl group, the phenylene group, and the biphenyldiyl group are each independently unsubstituted or substituted with a substituent, and
wherein the substituent is an alkyl group having 1 to 10 carbon atoms or an aryl group having 6 to 25 carbon atoms.

7. The light-emitting element according to claim 6, wherein the organic compound is represented by General Formula (G2)

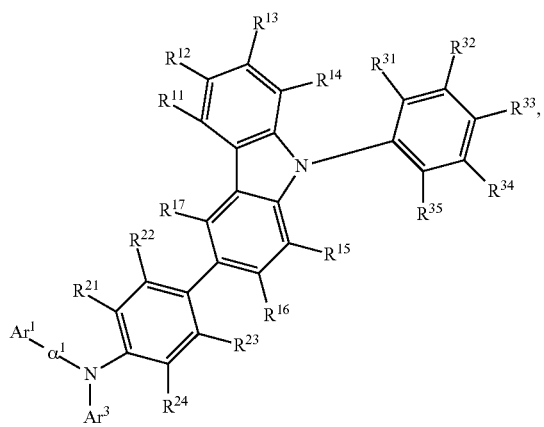

(G2)

and wherein $R^{31}$ to $R^{35}$ each independently represent hydrogen or an alkyl group having 1 to 10 carbon atoms.

8. The light-emitting element according to claim 6, wherein the organic compound is represented by General Formula (G3)

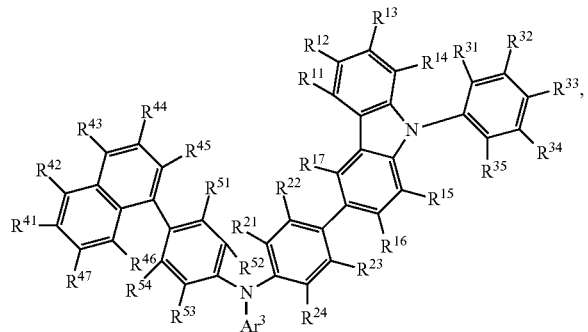

(G3)

wherein $R^{41}$ to $R^{47}$ and $R^{51}$ to $R^{54}$ each independently represent hydrogen, an alkyl group having 1 to 10 carbon atoms, or an aryl group having 6 to 25 carbon atoms, and wherein $R^{31}$ to $R^{35}$ each independently represent hydrogen or an alkyl group having 1 to 10 carbon atoms.

9. The light-emitting element according to claim 6, further comprising a hole-transport layer in contact with the light-emitting layer, the hole-transport layer comprising a second organic compound represented by General Formula (G1),

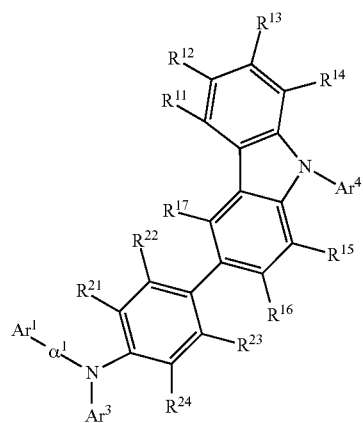

(G1)

wherein $Ar^1$ represents a naphthyl group, wherein $Ar^3$ represents a fluorenyl group or a spirofluorenyl group, wherein $Ar^4$ represents an aryl group having 6 to 25 carbon atoms, wherein $\alpha^1$ represents a phenylene group or a biphenyldiyl group, wherein $R^{11}$ to $R^{17}$ and $R^{21}$ to $R^{24}$ each independently represent hydrogen, an alkyl group having 1 to 10 carbon atoms, or an aryl group having 6 to 25 carbon atoms, wherein the naphthyl group, the fluorenyl group, the spirofluorenyl group, the phenylene group, and the biphenyldiyl group are each independently unsubstituted or substituted with a substituent, and wherein the substituent is an alkyl group having 1 to 10 carbon atoms or an aryl group having 6 to 25 carbon atoms.

10. The light-emitting element according to claim 6, further comprising a hole-transport layer in contact with the light-emitting layer, the hole-transport layer comprising the organic compound.

11. An electronic device comprising the light-emitting element according to claim 6.

12. A lighting device comprising the light-emitting element according to claim 6.

* * * * *